US006982321B2

(12) United States Patent
Winter

(10) Patent No.: US 6,982,321 B2
(45) Date of Patent: *Jan. 3, 2006

(54) ALTERED ANTIBODIES

(75) Inventor: Gregory Paul Winter, Cambridge (GB)

(73) Assignees: Medical Research Council, London (GB); BTG International Limited, London (GB)

( * ) Notice: Subject to any disclaimer, the term of this patent is extended or adjusted under 35 U.S.C. 154(b) by 144 days.

This patent is subject to a terminal disclaimer.

(21) Appl. No.: 10/351,748

(22) Filed: Jan. 24, 2003

(65) Prior Publication Data

Related U.S. Application Data

(63) Continuation of application No. 08/452,462, filed on May 26, 1995, now Pat. No. 6,548,640, which is a continuation of application No. 07/942,140, filed on Sep. 9, 1992, now abandoned, which is a continuation of application No. 07/624,515, filed on Dec. 7, 1990, now abandoned, which is a continuation of application No. 07/189,814, filed on May 3, 1988, now abandoned.

(51) Int. Cl.
*C07K 16/00* (2006.01)
(52) U.S. Cl. .................... 530/387.3; 424/130.1
(58) Field of Classification Search ............ 530/387.1, 530/387.3; 424/130.1
See application file for complete search history.

(56) References Cited

U.S. PATENT DOCUMENTS

| 4,816,567 A | 3/1989 | Cabilly et al. |
| 5,078,998 A | 1/1992 | Bevan et al. |
| 5,091,513 A | 2/1992 | Huston et al. |
| 5,225,539 A | 7/1993 | Winter |
| 5,585,089 A | 12/1996 | Queen et al. |
| 5,693,761 A | 12/1997 | Queen et al. |
| 5,693,762 A | 12/1997 | Queen et al. |
| 5,846,534 A * | 12/1998 | Waldmann et al. |
| 6,180,370 B1 | 1/2001 | Queen et al. |
| 6,548,640 B1 * | 4/2003 | Winter |
| 6,569,430 B1 * | 5/2003 | Waldmann et al. |

FOREIGN PATENT DOCUMENTS

| EP | 0125023 | 11/1984 |
| EP | 0173494 | 3/1986 |
| EP | 0183964 | 6/1986 |
| EP | 0184187 | 6/1986 |
| EP | 0239400 | 9/1987 |
| WO | WO 86/01533 | 3/1986 |
| WO | WO 91/09967 | * 7/1991 |
| WO | WO 91/09966 | 7/1992 |

OTHER PUBLICATIONS

Rudikoff et al (Proc Natl Acad Sci USA 1982 vol. 79 p. 1979.*
Panka et al (Proc Natl Acad Sci USA vol. 85 3080-3084 May 1988.*
Amit et al Science vol. 233 747-753 1986.*
Riechmann et al (Nature 332:323-327, Mar. 24, 1988.*
Cruse et al (Illustrated Dictionary of Immunology, CRC Press, 1995, p. 186.*
Sonnier et al (The New England journal of Medicine 309: 590-594, 1983.*
Kabat et al (Sequences of protein of Immunological interest, US department of health, 1997, pp. 41 and 45.*
Bentley, G.A., "Three-Dimensional Structure of an Idotope-Anti-idotope Complex," *Nature* 348:254-257 (1990).
Bhat, T.N. et al., "Small Rearrangements in Structures of Fv and Fab Fragments of Antibody D1.3 on Antigen Binding," *Nature* 347(6292):483-485 (1990).
Boulianne, et al., "Production of Functional Chimaeric Mouse/Human Antibody," *Nature* 312:643-646 (1984).
Bruggemann, et al., "Immunoglobulin V Region Variants in Hybridoma Cells I. Isolation of a Variant with Altered Idiotypic and Antigen Binding Specificity," *The EMBO Journal* 1(5):629-634 (1982).
Carter, et al., "Improved oligonucleotide site-directed mutagenesis using M13 vectors," *Nucleic Acids Res.* 13: 4431-4443 (1985).
Chen, P., et al., "Possible Involvement of Human D. Minigenes in the First Complementarity-Determining Region of k Light Chains," *Proceedings of the National Academy of Sciences of the U.S.A.* 82:2125-2127 (Apr. 1985).
Chothia et al., "The Predicted Structure of Immunoglobulin D1.3 and its Comparison with the Crystal Structure," *Science* 233:755-758 (1986).
Chothia et al., *J. Mol. Biol.* 196:901-917 (1987).
Chothia, C., et al., "Conformations of Immunoglobulin Hypervariable Regions," *Nature* 342:877-883 (1989).
Colman et al., *Nature* 326:358-363 (1987).
Davies, D.R., et al., "Antibody-Antigen Complexes," *J. Biol. Chem.* 263(22):10541-10544 (1988).
Dildrop et al., "Immunoglobulin V region variants in hybridoma cells. II. Recombination between V genes," *EMBO J.* 1:635-640.

(Continued)

Primary Examiner—Larry R. Helms
(74) Attorney, Agent, or Firm—Palmer & Dodge LLP; Barbara A. Gyure; Kathleen M. Williams

(57) ABSTRACT

An altered antibody is produced by replacing the complementarity determining regions (CDRs) of a variable region of an immunoglobulin (Ig) with the CDRs from an Ig of different specificity, using recombinant DNA techniques. The gene coding sequence for producing the altered antibody may be produced by site-directed mutagenesis using long oligonucleotides or using gene synthesis.

24 Claims, 27 Drawing Sheets

OTHER PUBLICATIONS

Duncan, A.R., et al., "the Binding Site for Clq on IgG," *Nature*, 332(6166):738-740 (1988).

Emery and Adair, "Humanised monoclonal antibodies for therapeutic applications," *Exp. Opin. Invest. Drugs* 3:241-251 (1994).

Epp et al., *Eur. J. Biochem* 45:513-524 (1974).

Fersht, et al., *Nature* 314:235-238 (1985).

Foote and Winter, "Antibody Framework Residues Affecting the Conformation of the Hypervariable Loops," *J. Mol. Biol.* 224:487-499 (1992).

Graziano et al., "Construction and characterization of a humanized anti-γ-immunoglobulin receptor type I (FcγRI) monoclonal antibody," *J. Immunol.* 155:4996-5002 (1995).

Groves, et al., *Hybridoma* 6(1):71-78 (1987).

Güssow and Seemann, "Humanization of monoclonal antibodies," *Methods on Enzymology, Acad. Press* 203(5): 99-121.

Hale, et al., *Laneet* 1394-1399 (1988).

Herron, J.N., et al., "Three-Dimensional Structure of a Fluorescein-Fab Complex . . . ," *Proteins: Structure, Function, and Genetics* 5:271-280 (1989).

Hodgson, "Protein Design: Rules, Empireism, and Nature," *Biotechnology* 8:1245-1247 (1990).

Hudson et al., "Immunoglobulin Chain Recombination Among Antidigoxin Antibodies . . . ," *J Immunol.* 139:2715-2723 (1987).

Jaffers et al., *Transplantation* 41:572-578 (1986).

Jones, P., et al., "Replacing the Complementarity-Determining Regions in a Human Antibody with Those from a Mouse," *Nature* 321:522-525 (May 1986).

Julius, M.A., et al., "The Structural Basis of Antigenic Determinants on Vk21 Light-Chains," *Mol. Immunol.* 18:1-9 (1981).

Kabat, et al., "Advances in Protein Chemistry," *Acadamic Press* 32:2-75 (1978).

Kabat, et al., "Evidence Supporting Somatic Assembly of the DNA Segments (Minigenes), Coding for the Framework, and Complementarity-Determining Segments of Immunoglobulin Variable Regions," *J. Exp. Med.* 149:1299-1313 (1979).

Kabat, et al., "Sequences of Proteins of Immunological Interest," pp. i-xx (1983).

Kettleborough, C.A., et al., "Humanization of a Mouse Monoclonal Antibody by CDR Grafting," *Protein Engineering* 4(7):772-783 (1991).

Lesk and Chothia, "Evolution of proteins formed by β-sheets: II. The core of the Immunoglobulin domains," *J. Mol. Biol.* 160:325-342 (1982).

Marks, J.D., et al., "By-Passing Immunization: Building High Affinity Human Antibodies by Chain Shuffling," *Biotechnology* (in press).

Morrison et al., "Chimeric Human Antibody Molecules: Mouse Antigen-Binding Domains with Human Constant Region Domains," *Natl. Acad. Sci. USA* 81:6851-6855 (1984).

Morrison, S.L., *Science* 229:1202-1207 (1985).

Munro, Alan, "Uses of chimaeric antibodies," *Nature* 312: 597 (1984).

Neuberger et al., *Nature* 314:268-270 (1985).

Neuberger, "Making novel antibodies by expressing transfected immunoglobulin genes," *Trends in Biochem. Sci.* 347-349 (1985).

Neuberger, "Novel antibodies by DNA transfection," *In Advances in Immunopharmacology 3, Proc. of Third Int'l Conf. Immunopharmacology, Florence, Italy* (1985).

Nose, et al., "Biological Significance of Carbohydrate Chains on Monoclonal Antibodies," *Proc. Natl. Acad. Sci. USA* 80:6632-6636 (1983).

Ochi, et al., "Functional Immunoglobulin M Production After Transfection of Cloned Immunoglobulin Heavy and Light Chain Genes Into Lymphoid Cells," *Natl. Acad. Sci. USA* 80:6351-6355 (1983).

Oi, et al., "Immunoglobulin Gene Expression in Transformed Lymphoid Cells," *Proc. Natl. Acad. Sci. USA* 80:825-829 (1983).

Old, R.W., et al., "Principles of Gene Manipulation," *Blackwell Scientific Pub.* 99-101 (1980).

Padlan et al., *Cold Springs Harbor Symp. Quant. Biol.* 41:627-637 (1976).

Padlan et al., *PNAS USA* 86:5938-5942 (1989).

Painter, R.G., et al., "Contribution of Heavy and Light Chains of Rabbit Immunoglobulin G to Antibody Activity," *Biochemistry* 11(8):1327-1337 (1972).

Rechavi, et al., "Organization and Evolution of Immunoglobulin VH Gene Subgroups," *Proc. Natl. Acad. Sci. USA* 82:4405-4409 (1982).

Rees and de la Paz, "Investigating antibody specificity using computer graphics and protein engineering," *Trends in Biochem. Sci.* 11: 144-148 (1986).

Riechman Declaration from Opposition of European Patent No. 451,216B1.

Riechman and Winter, "Recombinant Antibodies Advances in the Applications of Monoclonal Antibodies in the Clinical Oncology," *Abstract for Meeting at Wolfson Institute* (May 1987).

Sahagan, et al., "A Genetically Engineered Murine/Human Chimeric Antibody Retains Specificity for Human Tumor-Associated Antigen," *J. Immunol.* 137(3):1066-1074 (1986).

Sheriff, S., et al., "Three-Dimensional Structure of an Antibody-Antigen Complex," *Proc. Natl. Acad. Sci. USA* 84:8075-8079 (1977).

Sims et al., "A humanized CD18 antibody can block function without cell destruction," *J. Immunol.* 151:2296-2308.

Sofer et al., *Bio Techniques* 1(4):198-203 (1983).

Stanfield, R.L., "Crystal Structures of an Antibody to a Peptide and Its Complex with Peptide Antigen at 2.8 Å," *Science* 248:712-719 (1990).

Suh et al., *Proteins* 1:74-80 (1986).

Taub et al., *J. Bio. Chem.* 264:259-265 (1989).

Tempest et al., "Reshaping a human monoclonal antibody to inhibit human respiratory syncytial virus invection *in vivo*," *Bio/Technology* 9:266-271 (1991).

Tempest et al., "Efficient generation of a reshaped human mAb specific for the α toxin of *Clostridium perfringens*," *Protein Eng.* 7:1501-1507 (1994).

Tempest et al., "A humanized anti-tumor necrosis factor-α monoclonal antibody that acts as a partial, competitive antagonist of the template antibody," *Hybridoma* 13:183-190 (1994).

Tempest et al., "Identification of framework residues required to restore antigen binding during reshaping of a monoclonal antibody against the glycoprotein gB of human cytomegalovirus," *Int. J. Biol. Macromol.* 17:37-42 (1995).

Verhoeyen, et al., "Reshaping Human Antibodies: Grafting an Antilysozyme Activity," *Science* 239:1534-1536 (Mar. 1988).

Verhoeyen, et al., "Re-shaped human anti-PLAP anitbodies," *Monoclonal Anitbodies: Application sin Clinical Oncology*, A.A. Epenetos, Ed., Chapman and Hall, London Ch. 5:37-43.

Ward et al., *Nature* 341:544-546 (1989).

William, W.V., et al., *PNAS* 86:5537-5541 (1989).

Winter and Neuberger, "Protein engineering applied to enzymes and immunoglobulins," *Abstracts of 612 th Meeting of Biochem. Soc., St. George's Hosp. Med. School* (1984).

Winter and Neuberger, "A note on restructuring enzymes and antibodies," *Methodological Surveys in Biochem. Analysis Series A&B* 15:139-140 (1985).

Wu, et al., "Fourteen Nucleotides in the Second Complementarity-Determining Region of a Human Heavy-Chain Variable Region Gene Are Identical with a Sequence in a Human D Minigene," *Proc. Natl. Acad. Sci.* USA 79:5031-5032 (Aug. 1982).

Notice of Opposition to European Patent No. 0239400, filed May 2, 1995, by Celltech Therapeutics, Ltd.

Program of the 24th Harden Conference, "Protein engineering and site-directed mutagenesis," published by The Biochemical Society (1985).

Queen, et al., "A humanized antibody that binds to the interleukin 2 receptor," *PNAS* 86:10029-10033 (Dec. 1989).

Hodgson, "Protein Design: Rules, Empiricism & Nature," *Biotechnology* 8:1245-1247 (1990).

* cited by examiner

```
                                                    CDR1
                                                  31     35
                                                  NDYYT
                                                  SYWMH
                                                    CDR2
                                                  50              65
                                                  YVFYHGTSDDTTPLRS
                                                  RIDPNSGGTKYNEKFKS
                                                    CDR3
                                                  95        102
                                                  NLIAGCIDV
                                                  YDYYGSSYFDY
```

```
              FR1
        1                             30
        XVQLQESGPGLVRPSQTLSLTCTVSGSTFS
NEWM
B1-8    QVQLQQPGAELVKPGASVKLSCKASGYTFT

FR2
        36              49
        WVRQPPGRGLEWIG
NEWM
B1-8    WVKQRPGRGLEWIG

FR3
        66                                    94
        RVTMLVDTSKNQFSLRLRLSSVTAADTAVYYCAR
NEWM
B1-8    KATLTVDKPSSTAYMQLSSLTSEDSAVYYCAR

FR4
        103        113
        WGQGSLVTVSS
NEWM
B1-8    WGQGTTLTVSS
```

FIG. 2

HindIII −48                                                  −23           −7
5' ┊............ATGCAAATCCTCTGAATCTACATGGTAAATATAGGTTTGTCTATAC
    ■→ RNA starts         ■→ RNA starts
CACAAACAGAAAAACATGAGATCACAGTTCTCTCTACAGTTACTGAGCACACAGGACCTC
            NP leader                                Splice
    ┌─────────────────────────────────────────┐
    │ M  G  W  S  C  I  I  L  F  L  V  A  T  A  T │↓
    └─────────────────────────────────────────┘
ACCATGGGATGGAGCTGTATCATCCTCTTCTTGGTAGCAACAGCTACAGGTAAGGGGCTC

ACAGTAGCAGGCTTGAGGTCTGGACATATATATGGGTGACAATGACATCCACTTTGCCTT

Splice|            1                  5 | PstI        10
      ↓G  V  H  S  Q  V  Q  L  Q ↓ E  S  G  P  G  L  V  R
TCTCTCCACAGGTGTCCACTCCCAGGTCCAACTGCA GGAGAGCGGTCCAGGTCTTGTGAG
                                     5'└─────────1─────────
                                     3'┌─────────2──────────┐ ┌
    15            20              25              30         CDR 1
                                                          ┌────────┐
     P  S  Q  T  L  S  L  T  C  T  V  S  G  S  T  F  S  │ S  Y  W │
ACCTAGCCAGACCCTGAGCCTGACCTGCACCGTGTCTGGCAGCACCTTCAGCAGCTACTG
    ┘└─────3─────┘└─────5─────┘└──7──
─────4─────┐┌─────6─────┐┌─────8─────
                                                              CDR2
          35             40              45              50      52R
    ┌──────┐                                                  ┌─────────┐
    │ M  H │ W  V  R  Q  P  P  G  R  G  L  E  W  I  G       │ R  I  D  P │
GATGCACTGGGTGAGACAGCCACCTGGACGAGGTCTTGAGTGGATTGGAAGGATTGATCC
────7────┘└────9a────┘└────9b────┘└──11──
┐┌────10a────┐┌────10b────┐┌────12/14────
     55    CDR2     60              65              70
    │ N  S  G  G  T  K  Y  N  E  K  F  K  S │ R  V  T  M  L  V  D
TAATAGTGGTGGTACTAAGTACAATGAGAAGTTCAAGAGCAGAGTGACAATGCTGGTAGA
───11───┘└───13a───┘└───13b───┘└───15──

FIG.3A

```
        ──────12/14──────────┐ ┌──────16──────
        75              80       82A B  C        85
     T  S  K  N  Q  F  S  L  R  L  S  S  V  T  A  A  D  T  A  V
    CACCAGCAAGAACCAGTTCAGCCTGAGACTCAGCAGCGTGACAGCCGCCGACACCGCGGT
    ──────15──────┘ └──────17──────────┘ └──────19──────
     ──┐ ┌──────18──────────────┐ ┌──────20──────
       90            95   CDR3        100A B  C        105
     Y  Y  C  A  R │Y  D  Y  Y  G  S  S  Y  F  D  Y│ W  G  Q  G
    CTATTATTGTGCAAGATACGATTACTACGGTAGTAGCTACTTTGACTACTGGGGTCAAGG
    ────19────┘ └──────21──────┘ └──────23────┘ └─
     ──┐ ┌──────────22/24──────────────┐ ┌─26a──
         110            │Splice          │BamHI
     S  L  V  T  V  S  S▼              ▼
    CAGCCTCGTCACAGTCTCCTCAGGT.......193bp..... 3'
    ─25────────GACA 3'
    ─┐ ┌─26b─CTGTTCGA 5'
```

FIG.3B

D1.3 CDR1 oligonucleotide
5' CTG,TCT,CAC,CCA,GTT,TAC,ACC,ATA,GCC,GCT,GAA,GGT,GCT

FR2              D1.3 CDR1              FR1

D1.3 CDR2 oligonucleotide
5' CAT,TGT,CAC,TCT,GGA,TTT,GAG,AGC,TGA,ATT,ATA,GTC,TGT,

FR3              D1.3 CDR2
GTT,TCC,ATC,ACC,CCA,AAT,CAT,TCC,AAT,CCA,CTC

D1.3 CDR2             FR2

D1.3 CDR3 oligonucleotide
5' GCC,TTG,ACC,CCA,GTA,GTC,AAG,CCT,ATA,ATC,TCT,CTC,TCT,

FR4                  D1.3 CDR3

TGC,ACA,ATA
   FR3

```
              -15  SIGNAL    -10                    -5
            ┌─────────────────────────────────────────────┐
            │ M  A  V  L  A  L  L  F  C  L  V  T  F  P  S  C  I  L │
TCAGAGCATGGCTGTCCTGGCATTACTCTTCTGCCTGGTAACATTCCCAAGCTGTATCCT
  -1 +1           5                  10                15
┌───┐
│ S │ Q  V  Q  L  K  E  S  G  P  G  L  V  A  P  S  Q  S  L  S
└───┘
TTCCCAGGTGCAGCTGAAGGAGTCAGGACCTGGCCTGGTGGCGCCCTCACAGAGCCTGTC
       [A]
    20              25          *  *  *  CDR1  35
                                       ┌──────────────┐
    I  T  C  T  V  S  G  F  S  L  T  │ G  Y  G  V  N │ W  V  R  Q
                                       └──────────────┘
CATCACATGCACCGTCTCAGGGTTCTCATTAACCGGCTATGGTGTAAACTGGGTTCGCCA
    40              45          50  *  *  *  55      CDR2
                                                     ┌──────────────┐
    P  P  G  K  G  L  E  W  L  G  │ M  I  W  G  D  G  N  T  D  Y │
                                                     └──────────────┘
GCCTCCAGGAAAGGGTCTGGAGTGGCTGGGAATGATTTGGGGTGATGGAAACACAGACTA
    60      CDR2    65              70              75
┌──────────────┐
│ N  S  A  L  K  S │ R  L  S  I  S  K  D  N  S  K  S  Q  V  F
└──────────────┘
TAATTCAGCTCTCAAATCCAGACTGAGCATCAGCAAGGACAACTCCAAGAGCCAAGTTTT
    80      82A  B  C  I    85              90              95  *
                                                                ┌──────┐
    L  K  M  N  S  L  H  T  D  D  T  A  R  Y  Y  C  A  R │ E  R │
                                                                └──────┘
CTTAAAAATGAACAGTCTGCACACTGATGACACAGCCAGGTACTACTGTGCCAGAGAGAG
     *  *  *  CDR3      105              110                  ←
┌──────────────────┐
│ D  Y  R  L  D  Y │ W  G  Q  G  T  T  L  T  V  S  S
└──────────────────┘
AGATTATAGGCTTGACTACTGGGGCCAAGGCACCACTCTCACAGTCTCCTCA
  ─────D────→      ←─────────── JH2 ───────────→
```

FIG. 7

H3=HindIII, P=PstI, B=BamHI, N=NcoI, E=EcoRI, H2=HindII

H3=HindIII, P=PstI, B=BamHI, N=NcoI, E=EcoRI, H2=HindII

H3=HindIII, P=PstI, B=BamHI, N=NcoI, E=EcoRI, H2=HindII

H3=HindIII, P=PstI, B=BamHI, N=NcoI, E=EcoRI, H2=HindII

```
HindIII
5' ....!......ATGCAAATCCTCTGAATCTACATGGTAAATATAGGTTTGTCTATACC
    ■──► RNA starts      ■──► RNA starts
ACAAACAGAAAAACATGAGATCACAGTTCTCTCTACAGTTACTGAGCACACAGGACCTCA +60
             signal                              │Splice
       ⌈M  G  W  S  C  I  I  L  F  L  V  A  T  A  T⌉ ↓
CCATGGGATGGAGCTGTATCATCCTCTTCTTGGTAGCAACAGCTACAGGTAAGGGGCTCA +120
ATGAAGTTGTGGCTGAACTGGATTTTCCTTTTAACACTTTTAAAT
       ⌈M  K  L  W  L  N  W  I  F  L  L  T  L  L  N⌉

CAGTAGCAGGCTTGAGGTCTGGACATATATATGGGTGACAATGACATCCACTTTGCCTTT +180
     Splice│         oligos III, IV, VII
           ↓          1            5           10
          signal
       ⌈G  V  H  S⌉ Q  V  Q  L  Q  E  S  G  P  G  L  V  R
CTCTCCACAGGTGTCCACTCCCAGGTCCAACTGCAGGAGAGCGGTCCAGGTCTTGTGAGA +240
          GGTATCCAGTGTGAGGTGAAACTGTTGGAATCTGGAGGAGGCTTGGTACAG
       ⌈G  I  Q  C⌉ E  V  K  L  L  E  S  G  G  G  L  V  Q
                                        oligo XIII   oligo X
   15              20              25            30    CDR1
    P  S  Q  T  L  S  L  T  C  T  V  S  G  S* T  F  S* │D  F  Y│
CCTAGCCAGACCCTGAGCCTGACCTGCACCGTGTCTGGCAGCACCTTCAGCGATTTCTAC +300
CCGGGGGGGTTCTATGAGACTCTCCTGTGCAGGTTCTGGATTCACCTTCACTGATTTCTAC
    P  G  G  S  M  R  L  S  C  A  G  S  G  F  T  F  T │D  F  Y│
                oligo IX
   35              40              45          50    52 a
  │M  N│W  V  R  Q  P  P  G  R  G  L  E  W  I  G │F  I  R  D│
ATGAACTGGGTGAGACAGCCACCTGGACGAGGTCTTGAGTGGATTGGATTTATTAGAGAC +360
ATGAACTGGATCCGCCAGCCTGCAGGGAAGGCACCTGAGTGGCTGGGTTTTATTAGAGAC
  │M  N│W  I  R  Q  P  A  G  K  A  P  E  W  L  G │F  I  R  D│
       oligo XI
   b  c 53      55   CDR 2      60              65              70
  │K  A  K  G  Y  T  T  E  Y  N  P  S  V  K  G│ R  V  T  M  L
AAAGCTAAAGGTTACACAACAGAGTACAATCCATCTGTGAAGGGGAGAGTGACAATGCTG +420
AAAGCTAAAGGTTACACAACAGAGTACAATCCATCTGTGAAGGGGCGGTTCACCATCTCC
  │K  A  K  G  Y  T  T  E  Y  N  P  S  V  K  G│ R  F  T  I  S
```

FIG.9A-1

```
                    75              80      82 a b c 83      85
           V  D  T  S  K  N  Q  F  S  L  R  L  S  S  V  T  A  A  D  T
           GTAGACACCAGCAAGAACCAGTTCAGCCTGAGACTCAGCAGCGTGACAGCCGCCGACACC  +480
           AGAGATAATACCCAAAACATGCTCTATCTTCAAATGAACACCCTAAGAGCTGAGGACACT
           R  D  N  T  Q  N  M  L  Y  L  Q  M  N  T  L  R  A  E  D  T
                                              oligo XII
              90             95    CDR 3   100  a   b101            105
           A  V  Y  Y  C  A  R │E  G  H  T  A  A  P  F  D  Y│ W  G  Q
           GCGGTCTATTATTGTGCAAGAGAGGGCCACACTGCTGCTCCTTTTGATTACTGGGGTCAA  +540
           GCCACTTACTACTGTGCAAGAGAGGGCCACACTGCTGCTCCTTTTGATTACTGGGGCCAA
           A  T  Y  Y  C  A  R │E  G  H  T  A  A  P  F  D  Y│ W  G  Q
               oligos V, VI, VII
                                │Splice
                  110      113  │
           G  S  L  V  T  V  S  S ↓                                 │BamHI
           GGCAGCCTCGTCACAGTCTCCTCAGGT......................↓.....3'  +600
           GGAGTCATGGTCACAGTCTCCTCA
           G  V  M  V  T  V  S  S
```

Oligonucleotides: I:5'-GGC CAG TGG ATA GAC-3', III:5'-CAG TTT CAT CTA GAA CTG GAT A-3', IV:5'-GCA GTT GGG TCT AGA AGT GGA CAC C-3', V:5'-TCA GCT GAG TCG ACT GTG AC-3', VI:5'-TCA CCT GAG TCG ACT GTG AC-3', VII:5'-AGT TTC ACC TCG AGT GGA CAC CT-3', VIII:5'-TCA CCT GAG GAG ACT GTG AC-3', IX:5'-GGC TGG CGA ATC CAG TT-3', X:5'-CTG TCT CAC CCA GTT CAT GTA GAA ATC GCT GAA GGT GCT-3', XI:5'-CAT TGT CAC TCT CCC CTT CAC AGA TGG ATT GTA CTC TGT TGT GTA ACC TTT AGC TTT GTC TCT AAT AAA TCC AAT CCA CTC-3', XII:5'-GCC TTG ACC CCA GTA ATC AAA AGG AGC AGC AGT GTG GCC CTC TCT TGA ACA ATA-3', XIII:5'-AGA AAT CGG/C TGA AGG TGA AGC AGA CA-3'.

FIG.9A-2

```
HindIII
5'....!.......ATGCAAATCCTCTGAATCTACATGGTAAATATAGGTTTGTCTATACC
   ■──►RNA starts       ■──►RNA starts
ACAAACAGAAAAACATGAGATCACAGTTCTCTCTACAGTTACTGAGCACACAGGACCTCA +60
                                                         ATGA
                                                          Ⓜ
         signal                               Splice
    Ⓜ  G  W  S  C  I  I  L  F  L  V  A  T  A  T ↓
CCATGGGATGGAGCTGTATCATCCTCTTCTTGGTAGCAACAGCTACAGGTAAGGGGCTCA +120
TGGCTGCACTTCAACTCTTAGGGGTAGCTGCTAGCTCTGGCTCCCAG
    M  A  A  L  Q  L  L  G  V  A  A  S  S  G  S  Q

CAGTAGCAGGCTTGAGGTCTGGACATATATATGGGTGACAATGACATCCACTTTGCCTTT +180

Splice↓
  signal        1              5             10
    G  V  H  S  D  I  Q  M  T  Q  S  P  S  S  L  S  A
CTCTCCACAGGTGTCCACTCCGACATCCAGATGACCCAGAGCCCAAGCAGCCTGAGCGCC +240
         GCCATGAGATGTGACATCAAGATGACCCAGTCTCCCTCATTCCTGTCTGCA
    A  M  R  C  D  I  K  M  T  Q  S  P  S  F  L  S  A
                                          oligo XIV
     15              20             25           30      CDR 1
  S  V  G  D  R  V  T  I  T  C | K  A  S  Q  N  I  D  K  Y  L |
AGCGTGGGTGACAGAGTGACCATCACCTGTAAAGCAAGTCAGAATATTGACAAATACTTA +300
TCTGTGGGAGACAGAGTCACTCTCAACTGCAAAGCAAGTCAGAATATTGACAAATACTTA
  S  V  G  D  R  V  T  L  N  C | K  A  S  Q  N  I  D  K  Y  L |
                                                oligo XV
     35              40             45           50    CDR 2
| N | W  Y  Q  Q  K  P  G  K  A  P  K  L  L  I  Y | N  T  N |
AACTGGTACCAGCAGAAGCCAGGTAAGGCTCCAAAGCTGCTGATCTACAATACAAACAAT +360
AACTGGTATCAGCAAAAGCTTGGAGAATCTCCCAACTCCTGATATATAATACAAAACAAT
| N | W  Y  Q  Q  K  L  G  E  S  P  K  L  L  I  Y | N  T  N  N |
```

FIG.9B-1

```
       55              60              65            70
  ┌─────────┐
  │ L  Q  T │ G  V  P  S  R  F  S  G  S  G  T  D  F  T  F
  └─────────┘
TTGCAAACGGGTGTGCCAAGCAGATTCAGAGGTAGCGGTAGCGGTACCGACTTCACCTTC  +420
TTGCAAACGGGCATCCCATCAAGGTTCAGTGGCAGTGGATCTGGTACTGATTTCACACTC
  ┌─────────┐
  │ L  Q  T │ G  I  P  S  R  F  S  G  S  G  T  D  F  T  L
  └─────────┘
                                                   oligo XVI
       75              80              85           90   CDR 3
                                                      ┌────────────┐
   T  I  S  S  L  Q  P  E  D  I  A  T  Y  Y  C        │ L  Q  H  I  S │
                                                      └────────────┘
ACCATCAGCAGCCTCCAGCCAGAGGACATCGCCACCTACTACTGCTTGCAGCATATAAGT  +480
ACCATCAGCAGCCTGCAGCCTGAAGATGTTGCCACATATTTCTGCTTGCAGCATATAAGT
                                                      ┌────────────┐
   T  I  S  S  L  Q  P  E  D  I  A  T  Y  F  C        │ L  Q  H  I  S │
                                                      └────────────┘

95             100             105      108
  ┌─────────┐
  │ R  P  R  T │ F  G  Q  G  T  K  V  E  I  K  R
  └─────────┘
AGGCCGCGCACGTTCGGCCAAGGGACCAAGGTGGAAATCAAACGTGAGTAGAATTTAAAC  +540
AGGCCGCGCACGTTTGGAACTGGGACCAAGCTGGAGCTGAAACGG
  ┌─────────┐
  │ R  P  R  T │ F  G  T  G  T  K  L  E  L  K  R
  └─────────┘
              BamHI
              ─────
TTTGCTTCCTCAGTTGGATCC-3'
```

Oligonucleotides: II:5'-TGC AGC ATC AGC C-3', XIV:5'-CTG CTG GTA CCA GTT TAA GTA TTT GTC AAT ATT CTG ACT TGC TTT ACA GGT GAT GGT-3', XV:5'-GCT TGG CAC ACC CGT TTG CAA ATT GTT TGT ATT GTA GAT CAG CAG-3', XVI:5'-CCC TTG GCC GAA CGT GCG CGG CCT ACT TAT ATG CTG CAA GCA GTA GTA GGT-3'.

FIG.9B-2

Sequence of the synthetic gene HUVLLYSO

```
       D  I  Q  M  T  Q  S  P  S  S  L  S  A  S  V  G  D  R  V
CTGCA GACATCCAGATGACCCAGAGCCCAAGCAGCCTGAGCGCCAGCGTGGGTGACAGAG
GACGT CTGTAGGTCTACTGGGTCTCGGGTTCGTCGGACTCGCGGTCGCACCCACTGTCTC
         10        20        30        40        50        60

T  I  T  C  R  A  S  G  N  I  H  N  Y  L  A  W  Y  Q  Q  K
TGACCATCACCTGTAGAGCCAGCGGTAACATCCACAACTACCTGGCTTGGTACCAGCAGA
ACTGGTAGTGGACATCTCGGTCGCCATTGTAGGTGTTGATGGACCGAACCATGGTCGTCT
         70        80        90       100       110       120

P  G  K  A  P  K  L  L  I  Y  Y  T  T  T  L  A  D  G  V  P
AGCCAGGTAAGGCTCCAAAGCTGCTGATCTACTACACCACCACCCTGGCTGACGGTGTGC
TCGGTCCATTCCGAGGTTTCGACGACTAGATGATGTGGTGGTGGGACCGACTGCCACACG
         130       140       150       160       170       180

S  R  F  S  G  S  G  S  G  T  D  F  T  F  T  I  S  S  L  Q
CAAGCAGATTCAGCGGTAGCGGTAGCGGTACCGACTTCACCTTCACCATCAGCAGCCTCC
GTTCGTCTAAGTCGCCATCGCCATCGCCATGGCTGAAGTGGAAGTGGTAGTCGTCGGAGG
         190       200       210       220       230       240

P  E  D  I  A  T  Y  Y  C  Q  H  F  W  S  T  P  R  T  F  G
AGCCAGAGGACATCGCCACCTACTACTGCCAGCACTTCTGGAGCACCCCAAGGACGTTCG
TCGGTCTCCTGTAGCGGTGGATGATGACGGTCGTGAAGACCTCGTGGGGTTCCTGCAAGC
         250       260       270       280       290       300

Q  G  T  K  V  E  I  K  R
GCCAAGGGACCAAGGTGGAAATCAAACGTGAGTAGAATTTAAACTTTGCTTCCTCAGTTG
CGGTTCCCTGGTTCCACCTTTAGTTTGCACTCATCTTAAATTTGAAACGAAGGAGTCAAC
         310       320       330       340       350       360

GATCCTAGAATTC
CTAGGATCTTAAG
    370
```

FIG.10

```
                                                        ATGCAAATCCTCTGAAT
CTACATGGTAAATATAGGTTTGTCTATACCACAAACAGAAAAACATGAGATCACAGTTCT

M  G  W  S  C  I  I  L  F
CTCTACAGTTACTGAGCACACAGGGACCTCACCATGGGATGGAGCTGTATCATCCTCTTCT

L  V  A  T  A  T
TGGTAGCAACAGCTACAGGTAAGGGGCTCACAGTAGCAGGCTTGAGGTCTGGACATATAT

1
                                           G  V  H  S  D  I  Q
ATGGGTGACAATGACATCCACTTTGCCTTTCTCTCCACAGGTGTCCACTCCGACATCCA 5           10           15           20
 M  T  Q  S  P  S  S  L  S  A  S  V  G  D  R  V  T  I  T  C
ATGACCCAGAGCCCAAGCAGCCTGAGCGCCAGCGTGGGTGACAGAGTGACCATCACCTGT

***************************
     25           30           35           40
 R  A  S  G  N  I  H  N  Y  L  A  W  Y  Q  Q  K  P  G  K  A
AGAGCCAGCGGTAACATCCACAACTACCTGGCTTGGTACCAGCAGAAGCCAGGTAAGGCT

******************
     45           50           55           60
 P  K  L  L  I  Y  Y  T  T  T  L  A  D  G  V  P  S  R  F  S
CCAAAGCTGCTGATCTACTACACCACCACCCTGGCTGACGGTGTGCCAAGCAGATTCAGA 65           70           75           80
 G  S  G  S  G  T  D  F  T  F  T  I  S  S  L  Q  P  E  D  I
GGTAGCGGTAGCGGTACCGACTTCACCTTCACCATCAGCAGCCTCCAGCCAGAGGACATC

**********************
     85           90           95          100
 A  T  Y  Y  C  Q  H  F  W  S  T  P  R  T  F  G  Q  G  T  K
GCCACCTACTACTGCCAGCACTTCTGGAGCACCCCAAGGACGTTCGGCCAAGGGACCAAG 105      108
 V  E  I  K  R
GTGGAAATCAAACGTGAGTAGAATTTAAACTTTGCTTCCTCAGTTGGATCCTAGAATTC
```

FIG.11

ALTERED ANTIBODIES

This is a continuation of application No. 08/452,462 filed on May 26, 1995, now U.S. Pat. No. 6,548,640, which is a continuation of application Ser. No. 07/942,340 filed Sep. 9, 1992, now abandoned, which is a continuation of application Ser. No. 07/624,515 filed Dec. 7, 1990, now abandoned, which is a continuation of application Ser. No. 07/189,814 filed May 3, 1988, now abandoned, which are incorporated by reference herein in their entireties.

BACKGROUND OF THE INVENTION

1. Field of the Invention

The present invention relates to altered antibodies in which at least part of the complementarity determining regions (CDRs) in the light or heavy chain variable domains of the antibody have been replaced by analogous parts of CDRs from an antibody of different specificity. The present invention also relates to methods for the production of such altered antibodies. The term "altered antibody" is used herein to mean an antibody in which at least one residue of the amino acid sequence has been varied as compared with the sequence of a naturally occuring antibody.

2. Descripton of the Prior Art

Natural antibodies, or immunoglobulins, comprise two heavy chains linked together by disulphide bonds and two light chains, each light chain being linked to a respective heavy chain by disulphide bonds. The general structure of an antibody of class IgG (ie an immunoglobulin (Ig) of class gamma (G)) is shown schematically in FIG. 1 of the accompanying drawings.

Each heavy chain has at one end a variable domain followed by a number of constant domains. Each light chain has a variable domain at one end and a constant domain at its other end, the light chain variable domain being aligned with the variable domain of the heavy chain and the light chain constant domain being aligned with the first constant domain of the heavy chain. The constant domains in the light and heavy chains are not involved directly in binding the antibody to the antigen.

Each pair of light and heavy chains variable domains forms an antigen binding site. The variable domains of the light and heavy chains have the same general structure and each domain comprises four framework regions, whose sequences are relatively conserved, connected by three hypervariable or complementarity determining regions (CDRs) (see Kabat, E. A., Wu, T. T., Bilofsky, H., Reid-Miller, M. and Perry, H., in "Sequences of Proteins of Immunological Interest", U.S. Dept. Health and Human Services, 1983 and 1987). The four framework regions largely adopt a beta-sheet conformation and the CDRs form loops connecting, and in some cases forming part of, the beta-sheet structure. The CDRs are held in close proximity by the framework regions and, with the CDRs from the other variable domain, contribute to the formation of the antigen binding site.

For a more detailed account of the structure of variable domains, reference may be made to: Poljak, R. J., Amzel, L. M., Avey, H. P., Chen, B. L., Phizackerly, R. P. and Saul, F., PNAS USA, 70, 3305–3310, 1973; Segal, D. M., Padlan. E. A., Cohen, G. H., Rudikoff, S., Potter, M. and Davies, D. R., PNAS USA, 71, 4298–4302, 1974; and Marquart, M., Deisenhofer, J., Huber, R. and Palm, W., J. Mol. Biol., 141, 369–391, 1980.

In recent years advances in molecular biology based on recombinant DNA techniques have provided processes for the production of a wide range of heterologous polypeptides by transformation of host cells with heterologous DNA sequences which code for the production of the desired products.

EP-A-0 088 994 (Schering Corporation) proposes the construction of recombinant DNA vectors comprising a ds DNA sequence which codes for a variable domain of a light or a heavy chain of an Ig specific for a predetermined ligand. The ds DNA sequence is provided with initiation and termination codons at its 5'- and 3'-termini respectively, but lacks any nucleotides coding for amino acids superfluous to the variable domain. The ds DNA sequence is used to transform bacterial cells. The application does not contemplate variations in the sequence of the variable domain.

EP-A-1 102 634 (Takeda Chemical Industries Limited) describes the cloning and expression in bacterial host organisms of genes coding for the whole or a part of human IgE heavy chain polypeptide, but does not contemplate variations in the sequence of the polypeptide.

EP-A-0 125 023 (Genentech Inc.) proposes the use of recombinant DNA techniques in bacterial cells to produce Igs which are analogous to those normally found in vertebrate systems and to take advantage of the gene modification techniques proposed therein to construct chimeric Igs, having amino acid sequence portions homologous to sequences from different Ig sources, or other modified forms of Ig.

The proposals set out in the above Genentech application did not lead to secretion of chimeric Igs, but these were produced as inclusion bodies and were assembled in vitro with a low yield of recovery of antigen binding activity.

The production of monoclonal antibodies was first disclosed by Kohler and Milstein (Kohler, G. and Milstein, C., Nature, 256, 495–497, 1975). Such monoclonal antibodies have found widespread use not only as diagnostic reagents (see, for example, 'Immunology for the 80s', Eds. Voller, A., Bartlett, A., and Bidwell, D., MTP Press, Lancaster, 1981) but also in therapy (see, for example, Ritz, J. and Schlossman, S. F., Blood, 59, 1–11, 1982).

The recent emergence of techniques allowing the stable introduction of Ig gene DNA into myeloma cells (see, for example, Oi, V. T., Morrison, S. L., Herzenberg, L. A. and Berg, P., PNAS USA, 80, 825–829, 1983; Neuberger, M. S., EMBO J., 2, 1373–1378, 1983; and Ochi, T., Hawley, R. G., Hawley, T., Schulman, M. J., Traunecker, A., Kohler, G. and Hozumi, N., PNAS USA, 80, 6351–6355, 1983), has opened up the possibility of using in vitro mutagenesis and DNA transfection to construct recombinant Igs possessing novel properties.

However, it is known that the function of an Ig molecule is dependent on its three dimensional structure, which in turn is dependent on its primary amino acid sequence. Thus, changing the amino acid sequence of an Ig may adversely affect its activity. Moreover, a change in the DNA sequence coding for the Ig may affect the ability of the cell containing the DNA sequence to express, secrete or assemble the Ig.

It is therefore not at all clear that it will be possible to produce functional altered antibodies by recombinant DNA techniques.

However, colleagues of the present Inventor have devised a process whereby chimeric antibodies in which both parts of the protein are functional can be secreted. The process, which is disclosed in International Patent Application No. PCT/GB85/00392 (WO86/01533) (Neuberger et al. and Celltech Limited), comprises:

a) preparing a replicable expression vector including a suitable promoter operably linked to a DNA sequence comprising a first part which encodes at least the variable domain of the heavy or light chain of an Ig molecule and a second part which encodes at least part of a second protein;

b) if necessary, preparing a replicable expression vector including a suitable promoter operably linked to a DNA sequence which encodes at least the variable domain of a complementary light or heavy chain respectively of an Ig molecule;

c) transforming an immortalised mammalian cell line with the or both prepared vectors; and d) culturing said transformed cell line to produce a chimeric antibody.

The second part of the DNA sequence may encode:

i) at least part, for instance the constant domain of a heavy chain, of an Ig molecule of different species, class or subclass;

ii) at least the active portion or all of an enzyme;

iii) a protein having a known binding specificity;

iv) a protein expressed by a known gene but whose sequence, function or antigenicity is not known; or v) a protein toxin, such a ricin.

The above Neuberger application only shows the production of chimeric antibodies in which complete variable domains are coded for by the first part of the DNA sequence. It does not show any chimeric antibodies in which the sequence of the variable domain has been altered.

EP-A-0 173 494 (The Board of Trustees of the Leland Stanford Junior University) also concerns the production of chimeric antibodies having variable domains from one mammalian source and constant domains from another mammalian source. However, there is no disclosure or suggestion of production of a chimeric antibody in which the sequence of a variable domain has been altered: indeed, hitherto variable domains have been regarded as indivisible units.

SUMMARY OF THE INVENTION

The present invention, in a first aspect, provides an altered antibody in which at least part of a CDR in a light or heavy chain variable domain has been replaced by analogous part(s) of a CDR from an antibody of different specificity.

The determination as to what constitutes a CDR and what constitutes a framework region is made on the basis of the amino-acid sequences of a number of Igs. However, from the three dimensional structure of a number of Igs it is apparent that the antigen binding site of an Ig variable domain comprises three looped regions supported on sheet-like structures. The loop regions do not correspond exactly to the CDRs, although in general there is considerable overlap.

Moreover, not all of the amino-acid residues in the loop regions are solvent accessible and in at least one case it is known that an amino-acid residue in the framework region is involved in antigen binding. (Amit, A. G., Mariuzza, R. A., Phillips, S. E. V. and Poljak, R. J., Science, 233, 747–753, 1986).

It is also known that the variable regions of the two parts of an antigen binding site are held in the correct orientation by inter-chain non-covalent interactions. These may involve amino-acid residues within the CDRs.

Further, the three dimensional structure of CDRs, and therefore the ability to bid antigen, depends on the interaction with the framework regions: thus in some cases transplanting CDRs to a different framework might destroy antigen binding.

In order to transfer the antigen binding capacity of one variable domain to another, it may not be necessary in all cases to replace all of the CDRs with the complete CDRs from the donor variable region. It may, eg, be necessary to transfer only those residues which are accessible from the antigen binding site. In addition, in some cases it may also be necessary to alter one or more residues in the framework regions to retain antigen binding capacity: this is found to be the case with reshaped antibody to Campath 1, which is discussed below.

It may also be necessary to ensure that residues essential for inter-chain interactions are preserved in the acceptor variable domain.

Within a domain, the packing together and orientation of the two disulphide bonded beta-sheets (and therefore the ends of the CDR loops) are relatively conserved. However, small shifts in packing and orientation of these beta-sheets do occur (Lesk, A. M. and Chothia, C., J. Mol. Biol., 160, 325–342, 1982). However, the packing together and orientation of heavy and light chain variable domains is relatively conserved (Chothia, C., Novotny, J., Bruccoleri, R. and Karplus, M., J. Mol. Biol., 186, 651–653, 1985). These points will need to be borne in mind when constructing a new antigen binding site so as to ensure that packing and orientation are not altered to the deteriment of antigen binding capacity.

It is thus clear that merely by replacing at least part of one or more CDRs with complementary CDRs may not always result in a functional altered antibody. However, given the explanations set out above, it will be well within the competence of the man skilled in the art, either by carrying out routine experimentation or by trial and error testing to obtain a functional altered antibody.

Preferably, the variable domains in both the heavy and light chains have been altered by at least partial CDR replacement and, if necessary, by partial framework region replacement and sequence changing. Although the CDRs may be derived from an antibody of the same species class or even subclass as the antibody from which the framework regions are derived, it is envisaged that the CDRs will generally preferably be derived from an antibody of different species and/or from an antibody of different class or subclass.

Thus, it is envisaged, for instance, that the CDRs from a mouse antibody could be grafted onto the framework regions of a human antibody. This arrangement will be of particular use in the therapeutic use of monoclonal antibodies.

At present, if a mouse monoclonal antibody is injected into a human, the human body's immune system recognises the antibody as foreign and produces an immune response thereto. Thus, on subsequent injections of the mouse antibody into the human, its effectiveness is considerably reduced by the action of the body's immune system against the foreign antibody. In the altered antibody of the present invention, only the CDRs of the antibody will be foreign to the body, and this should minimise side effects if used for human therapy. Although, for example, human and mouse framework regions have characteristic sequences, to a first approximation there seem to be no characteristic features which distinguish human from mouse CDRs. Thus, an antibody comprised of mouse CDRs in a human framework may well be no more foreign to the body than a genuine human antibody.

Even with the altered antibodies of the present invention, there is likely to be an anti-idiotypic response by the recipient of the altered antibody. This response is directed to the antibody binding region of the altered antibody. It is believed that at least some anti-idiotype antibodies are directed at sites bridging the CDRs and the framework regions. It would therefore be possible to provide a panel of antibodies having the same partial or complete CDR replacements but on a series of different framework regions. Thus, once a first altered antibody became therapeutically ineffective, due to an anti-idiotype response, a second altered antibody from the series could be used, and so on, to overcome the effect of the anti-idiotype response. Thus, the useful life of the antigen-binding capacity of the altered antibodies could be extended.

Preferably, the altered antibody has the structure of a natural antibody or a fragment thereof. Thus, the altered antibody may comprise a complete antibody, an $(Fab')_2$ fragment, an Fab fragment, a light chain dimer or an Fv fragment. Alternatively, the altered antibody may be a chimeric antibody of the type described in the Neuberger application referred to above. The production of such an altered chimeric antibody can be carried out using the methods described below used in conjunction with the methods described in the Neuberger application.

The present invention, in a second aspect, comprises a method for producing an altered antibody comprising:

a) preparing a first replicable expression vector including a suitable promoter operably linked to a DNA sequence which encodes at least a variable domain of an Ig framework regions consisting at least parts of framework regions from a first antibody and CDRs comprising at least part of the CDRs from a second antibody of different specificity;

b) if necessary, preparing a second replicable expression vector including a suitable promoter operably linked to a DNA sequence which encodes at least the variable domain of a complementary Ig light or heavy chain respectively;

c) transforming a cell line with the first or both prepared vectors; and d) culturing said transformed cell line to produce said altered antibody.

Preferably, the cell line which is transformed to produce the altered antibody is an immortalised mammalian cell line, which is advantageously of lymphoid origin, such as a myeloma, hybridoma, trioma or quadroma cell line. The cell line may also comrpise a normal lymphoid cell, such as a B-cell, which has been immortalised by transformation with a virus, such as the Epstein-Barr virus. Most preferably, the immortalised cell line is a myeloma cell line or a derivative thereof.

Although the cell line used to produce the altered antibody is preferably a mammalian cell line, any other suitable cell line, such as a bacterial cell line or a yeast cell line, may alternatively be used. In particular, it is envisaged that $E. Coli$ derived bacterial strains could be used.

It is known that some immortalised lymphoid cell lines, such as myeloma cell lines, in their normal state secrete isolated Ig light or heavy chains. If such a cell line is transformed with the vector prepared in step a) of the process of the invention, it will not be necessary to carry out step b) of the process, provided that the normally secreted chain is complementary to the variable domain of the Ig chain encoded by the vector prepared in step a).

In general the immortalised cell line will not secrete a complementary chain, and it will be necessary to carry out step b). This step may be carried out by further manipulating the vector produced in step a) so that this vector encodes not only the variable domain of an altered antibody light or heavy chain, but also the complementary variable domain. Alternatively, step b) is carried out by preparing a second vector which is used to transform the immortalised cell line.

The techniques by which such vectors can be produced and used to transform the immortalised cell lines are well known in the art, and do not form any part of the invention.

In the case where the immortalised cell line secretes a complementary light or heavy chain, the transformed cell line may be produced for example by transforming a suitable bacterial cell with the vector and then fusing the bacterial cell with the immortalised cell line by spheroplast fusion. Alternatively, the DNA may be directly introduced into the immortalised cell line by electroporation. The DNA sequence encoding the altered variable domain may be prepared by oligonucleotide synthesis. This requires that at least the framework region sequence of the acceptor antibody and at least the CDRs sequences of the donor antibody are known or can be readily determined. Although determining these sequences, the synthesis of the DNA from oligonucleotides and the preparation of suitable vectors is to some extent laborious, it involves the use of known techniques which can readily be carried out by a person skilled in the art in light of the teaching given here.

If it was desired to repeat this strategy to insert a different antigen binding site, it would only require the synthesis of oligonucleotides encoding the CDRs, as the framework oligonucleotides can be re-used.

A convenient variant of this technique would involve making a symthetic gene lacking the CDRs in which the four framework regions are fused together with suitable restriction sites at the junctions. Double stranded synthetic CDR cassettes with sticky ends could then be ligated at the junctions of the framework regions. A protocol for achieving this variant is shown diagrammatically in FIG. 6 of the accompanying drawings.

Alternatively, the DNA sequence encoding the altered variable domain may be prepared by primer directed oligonucleotide site-directed mutagenesis. This technique in essence involves hybridising an oligonucleotide coding for a desired mutation with a single strand of DNA containing the region to be mutated and using the signle strand as a template for extension of the oligonucleotide to produce a strand containing the mutation. This technique, in various forms, is described by: Zoller, M. J. and Smith, M., Nuc. Acids Res., 10, 6487–6500, 1982; Norris, K., Norris, F., Christainsen, L. and Fiil, N., Nuc. Acids Res., 11, 5103–5112, 1983; Zoller, M. J. and Smith, M., DNA, 3, 479–488 (1984); Kramer, W., Schughart, K. and Fritz, W.-J., Nuc. Acids Res., 10, 6475–6485, 1982.

For various reasons, this technique in its simplest form does not always produce a high frequency of mutation. An improved technique for introducing both single and multiple mutations in an M13 based vector, has been described by Carter et al. (Carter, P., Bedouelle H. and Winter, G., Nuc. Acids Res., 13, 4431–4443, 1985).

Using a long oligonucleotide, it has proved possible to introduce many changes simultaneously (as in Carter et al., loc. cit.) and thus single oligonucleotides, each encoding a CDR, can be used to introduce the three CDRs from a second antibody into the framework regions of a first antibody. Not only is this technique less laborious than total gene synthesis, but is represents a particularly convenient way of expressing a variable domain of required specificity, as it can be simpler than tailoring an entire $V_H$ domain for insertion into an expression plasmid.

The oligonucleotides used for site-directed mutagenesis may be prepared by oligonucleotide synthesis or may be isolated from DNA coding for the variable domain of the second antibody by use of suitable restriction enzymes. Such long oligonucleotides will generally be at least 30 bases long and may be up to or over 80 bases in length.

The techniques set out above may also be used, where necessary, to produce the vector of part (b) of the process.

The method of the present invention is envisaged as being of particular use in reshaping human monoclonal antibodies by introducing CDRs of desired specificity. Thus, for instance, a mouse monoclonal antibody against a particular human cancer cell may be produced by techniques well known in the art. The CDRs from the mouse monoclonal antibody may then be partially or totally grated into the framework regions of a human monoclonal antibody, which is then produced in quantity by a suitable cell line. The product is thus a specifically targeted, essentially human antibody which will recognise the cancer cells, but will not itself be recognised to any significant degree, by a human's immune system, until the anti-idiotype response eventually becomes apparent. Thus, the method and product of the present invention will be of particular use in the clinical environment.

The present invention is now described, by way of example only, with reference to the accompanying drawings.

BRIEF DESCRIPTION OF THE DRAWINGS

In the drawings:

FIG. 2 shows the amino acid sequence of the $V_H$ domain of NEWM in comparison with the $V_H$ domain of the BI-8 antibody;

FIG. 3 shows the amino acid and nucleotide sequence of the $HuV_{NP}$ gene.

FIG. 7 shows the sequence of the variable domain of antibody D1.3 and the gene coding therefor;

FIG. 9 illustrates nucleic acid and amino acid sequences of the variable domains of antibodies to Campath-1, with FIG. 9a representing the heavy chain and FIG. 9b representing the light chain;

FIG. 10 illustrates the sequence of the HuVLLYS° gene and derived amino acid sequence;

FIG. 11 illustrates the sequences of the HuVLLYS gene and derived amino acid sequence, with asterisks marking the CDRs;

DETAILED DESCRIPTION OF EMBODIMENTS

Example 1

Figure 1:
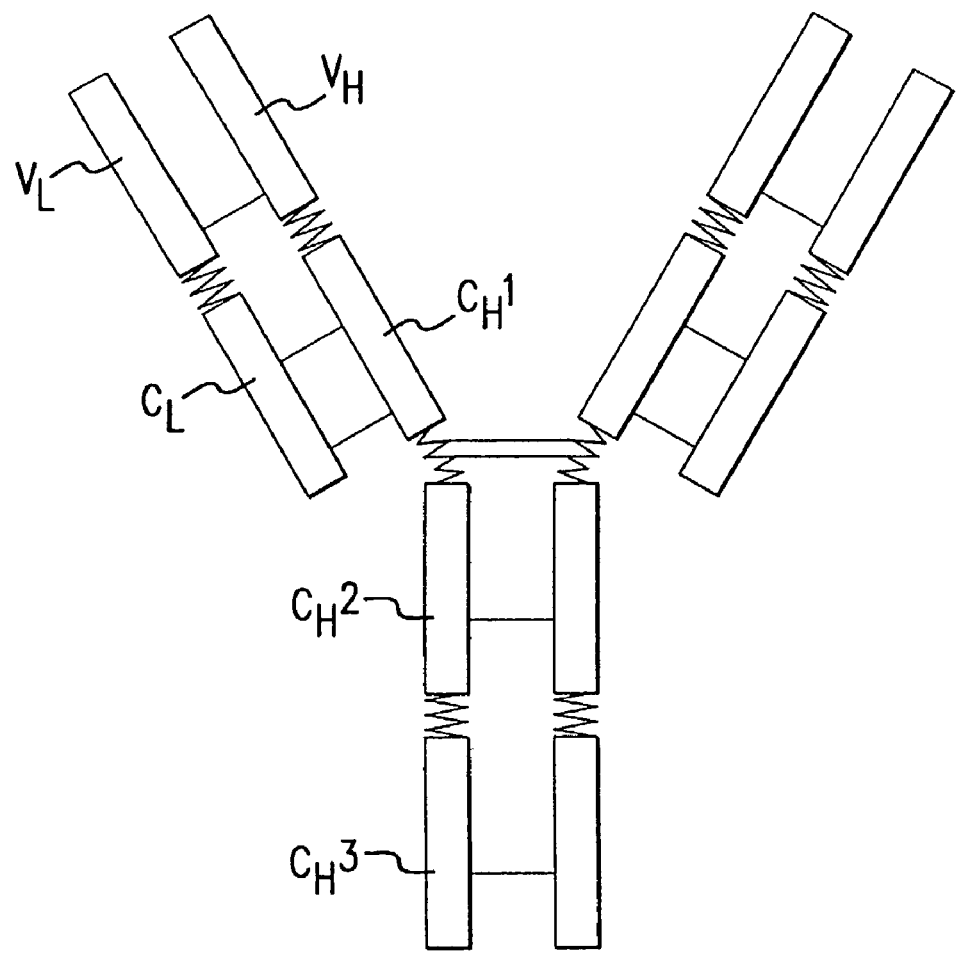
FIG. 1 is a schematic diagram showing the structure of an IgG molecule.

This example shows the production of an altered antibody in which the variable domain of the heavy chains comprises the framework regions of a human heavy chain and the CDRs from a mouse heavy chain.

The framework regions were derived from the human myeloma heavy chain NEWM, the crystallographic structure of which is known (see Poljak et al., loc. cit. and Bruggemann, M., Radbruch, A., and Rajewsky, K., EMBO J., 1, 629–634, 1982.)

The CDRs were derived from the mouse monoclonal antibody B1-0.8 (see Reth et al., loc. cit.), which binds the hapten NP-cap (4-hydroxy-3-nitrophenyl acetyl-caproic acid: $K_{NP\text{-}CAP}$ =1.2 uM).

A gene encoding a variable domain $HuV_{NP}$, comprising the B1-8 CDRs and the NEWM framework regions, was constructed by gene synthesis as follows.

The amino acid sequence of the $V_H$ domain of NEWM is shown in FIG. 2, wherein it is compared to the amino acid sequence of the $V_H$ domain of the B1-8 antibody. The sequence is divided into framework regions and CDRs according to Kabat et al. (loc. cit.). Conserved residues are marked with a line.

The amino acid and nucleotide sequence of the $HuV_{NP}$ gene, in which the CDRs from the B1-8 antibody alternate with the framework regions of the NEWM antibody, is shown in FIG. 3. The $HuV_{NP}$ gene was derived by replacing sections of the $MOV_{NP}$ gene in the vector pSV-$V_{NP}$ (see Neuberger, M. S., Williams, G. T., Mitchell, E. B., Jouhal, S., Flanagan, J. G. and Rabbitts, T. H., Nature, 314, 268–270, 1985) by a synthetic fragment encoding the $HuV_{NP}$ domain. Thus the 5' and 3' non-encoding sequences, the leader sequence, the L-V intron, five N-terminal and four C-terminal amino acids are from the $MoV_{NP}$ gene and the rest of the coding sequence is from the synthetic $HuV_{NP}$ fragment.

The oligonucleotides from which the $HuV_{NP}$ fragment was assembled are aligned below the corresponding portion of the $HuV_{NP}$ gene. For convenience in cloning, the ends of oligonucleotides 25 and 26b form a Hind II site followed by a Hind III site, and the sequences of the 25/26b oligonucleotides therefore differ from the $HuV_{NP}$ gene.

The $HuV_{NP}$ synthetic fragment was built as a PstI-Hind III fragment. The nucleotide sequence was derived from the protein sequence using the computer programme ANALYSEQ (Staden, R., Nuc. Acids. Res., 12, 521–538, 1984) with optimal codon usage taken from the sequences of mouse constant domain genes. The oligonucleotides (1 to 26b, 28 in total) vary in size from 14 to 59 residues and were made on a Biosearch SAM or an Applied Biosystems machine, and purified on 8M-urea polyacrylamide gels (see Sanger, F. and Coulson, A., FEBS Lett., 107–110, 1978).

The oligonucleotides were assembled in eight single stranded blocks (A–D) containing oligonucleotides

[1,3,5,7] (Block A), [2,4,6,8] (block A'), [9,11,13a,13b] (Block B), [10a, 10b,12/14] (block B'), [15,17] (block C), [16,18] (block C'), [19, 21, 23, 25] (block D) and [20, 22/24, 26a, 26b] (block D').

In a typical assembly, for example of block A, 50 pmole of oligonucleotides 1,3,5 and 7 were phosphorylated at the 5' end with T4 polynucleotide kinase and mixed together with 5 pmole of the terminal oligonucleotide [1] which had been phosphorylated with 5 uCi [gamma-$^{32}$-P] ATP (Amersham 3000 Ci/mmole). These oligonucleotides were annealed by heating to 80° C. and cooling over 30 minutes to room temperature, with unkinased oligonucleotides 2, 4 and 6 as splints, in 150 ul of 50 mM Tris.Cl, ph 7.5, 10 mM $MgCl_2$. For the ligation, ATP (1 mM) and DTT (10 mM) were added with 50 U T4 DNA ligase (Anglian Biotechnology Ltd.) and incubated for 30 minutes at room temperature. EDTA was added to 10 mM, the sample was extracted with phenol, precipitated from ethanol, dissolved in 20 ul water and boiled for 1 minute with an equal volume of formamide dyes. The sample was loaded onto and-run on a 0.3 mm 8M-urea 10% polyacrylamide gel. A band of the expected size was detected by autoradiography and eluted by soaking.

Two full length single strands were assembled from blocks A to D and A' to D' using splint oligonucleotides. Thus blocks A to D were annealed and ligated in 30 ul as set out in the previous paragraph using 100 pmole of olignucleotides 10a, 16 and 20 as splints. Blocks A' to D' were ligated using oligonucleotides 7, 13b and 17 as splints.

After phenol/ether extraction, block A-D was annealed with block A'-D', small amounts were cloned in the vector M13mp18 (Yanish-Perron, C., Vieria, J. and Messing, J., Gene, 33, 103–119, 1985) cut with PstI and Hind III, and the gene sequenced by the dideoxy technique (Sanger, F., Nicklen, S. and Coulson, A. R., PNAS USA, 74, 5463–5467, 1977).

The $MoV_{NP}$ gene was transferred as a Hind III-BamHI fragment from the vector pSV-$V_{NP}$ (Neuberger et al., loc. cit.) to the vector M13mp8 (Messing, J. and Vieria, J., Gene, 19, 269–276, 1982). To facilitate the replacement of $MoV_{NP}$ coding sequences by the synthetic $HuV_{NP}$ fragment, three Hind II sites were removed from the 5' non-coding sequence by site directed mutagenesis, and a new Hind II site was subsequently introduced near the end of the fourth framework region (FR4 in FIG. 2). By cutting the vector with PstI and Hind II, most of the $V_{NP}$ fragment can be inserted as a PstI-Hind II fragment. The sequence at the Hind II site was corrected to NEWM FR4 by site directed mutagenesis.

The Hind III-Bam HI fragment, now carrying the $HuV_{NP}$ gene, was excised from M13 and cloned back into pSV-$V_{NP}$ to replace the $MoV_{NP}$ gene and produce a vector pSV-$HuV_{NP}$. Finally, the genes for the heavy chain constant domains of human Ig E (Flanagan, J. G. and Rabbitts, T. H., EMBO J., 1, 655–660, 1982) were introduced as a Bam HI fragment to give the vector pSV-$HuV_{NP}$.HE. This was transfected into the mouse myeloma line J558 L by spheroplast fusion.

The sequence of the $HuV_{NP}$ gene in pSV-$HuV_{NP}$.HE was checked by recloning the Hind III-Bam HI fragment back into M13mp8 (Messing et al., loc. cit.). J558L myeloma cells secrete lambda 1 light chains which have been shown to associate with heavy chains containing the $MoV_{NP}$ variable domain to create a binding site for NP-cap or the related hapten NIP-Cap (3-iodo-4-hydroxy-5-nitrophenylacetyl-caproic acid) (Reth, M., Hammerling, G. J. and Rajewsky, K., Eur. J. Immunol., 8, 393–400, 1978).

As the plasmid pSV-$HuV_{NP}$.HE contains the gpt marker, stably transfected myeloma cells could be selected in medium containing mycophenolic acid. Transfectants secreted an antibody ($Huv_{NP}$-IgE) with heavy chains comprising a $HuV_{NP}$ variable domain (ie a "humanised" mouse variable region) and human epsilon constant domains, and lambda 1 light chains from the J558L myeloma cells.

The culture supernatants of several gpt$^+$ clones were assayed by radioimmunoassay and found to contain NIP-cap binding antibody. The antibody secreted by one such clone was purified from culture supernatant by affinity chromatography on NIP-cap Sepharose (Sepharose is a registered trade mark). A polyacrylamide-SDS gel indicated that the protein was indistinguishable from the chimeric antibody $MoV_{NP}$-IgE (Neuberger et al., loc. cit.).

The $HuV_{NP}$-IgE antibody competes effectively with the $MoV_{NP}$-IgE for binding to both anti-human-IgE and to NIP-cap coupled to bovine serum albumin.

Various concentrations of $HuV_{NP}$-IgE and $MoV_{NP}$-IgE were used to compete with the binding of radiolabelled $MoV_{NP}$-IgE to polyvinyl microtitre plates coated with (a) Sheep anti-human-IgE antiserum (Seward Laboratories); (b) NIP-cap-bovine serum albumin; (c) Ac38 anti-idiotypic antibody; (d) Ac 146 anti-idiotypic antibody; and (e) rabbit anti-$MoV_{NP}$ antiserum. Binding was also carried out in the presence of $MoV_{NP}$-IgM antibody (Neuberger, M. S., Williams, G. T. and Fox, R. O., Nature, 312, 604–608, 1984) or of JW5/1/2 which is an IgM antibody differing from the $MoV_{NP}$-IgM antibody at 13 residues mainly located in the $V_H$ CDR2 region.

The results of the binding assays are shown in FIG. 4, wherein black circles represent $HuV_{NP}$, white circles $MoV_{NP}$, black squares $MoV_{NP}$-IgM and white squares JW5/1/2. Binding is given relative to the binding in the absence of the inhibitor.

The affinities of $HuV_{NP}$-IgE for NP-cap and NIP-cap were then measured directly using the fluorescence quench technique and compared to those for MoVNP-IgE, using excitation at 295 nm and observing emission at 340 nm (Eisen, H. N., Methods Med. Res., 10, 115–121, 1964).

Antibody solutions were diluted to 100 nM in phosphate buffered saline, filtered (0.45 um pore cellulose acetate) and titrated with NP-cap in the range 0.2 to 20 uM. As a control, mouse DI-3 antibody (Mariuzza, R. A., Jankovic, D. L., Bulot, G., Amit, A. G., Saludjian, P., Le Guern, A., Mazie, J. C. and Poljak, R. J., J. Mol. Biol., 170, 1055–1058, 1983), which does not bind hapten, was titrated in parallel.

Decrease in the ratio of the fluorescence of $HuV_{NP}$-IgE or $Huv_{NP}$-IgE to the fluorescence of the D1-3 antibody was taken to be proportional to NP-cap occupancy of the antigen binding sites. The maximum quench was about 40% for both antibodies, and hapten dissociation constants were determined from least-squares fits of triplicate data sets to a hyperbola.

For NIP-cap, hapten concentration varied from 10 to 300 nM, and about 50% quenching of fluorescence was observed at saturation. Since the antibody concentrations were comparable to the value of the dissociation constants, data were fitted by least squares to an equation describing tight binding inhibition (Segal, I. H., in "Enzyme Kinetics", 73–74, Wiley, New York, 1975).

The binding constants obtained from these data for these antibodies are shown in Table 1 below.

TABLE 1

|  | $K_{NP}$-cap | $K_{NIP}$-cap |
|---|---|---|
| $MoV_{NP}$-IgE | 1.2 uM | 0.02 uM |
| $HuV_{NP}$-IgE | 1.9 uM | 0.07 uM |

These results show that the affinities of these antibodies are similar and that the change in affinity is less than would be expected for the loss of a hydrogen bond or a van der Waals contact point at the active site of an enzyme.

Thus, it has been shown that it is possible to produce an antibody specific for an artificial small hapten, comprising a variable domain having human framework regions and mouse CDRs, without any significant loss of antigen binding capacity.

Figure 4A:
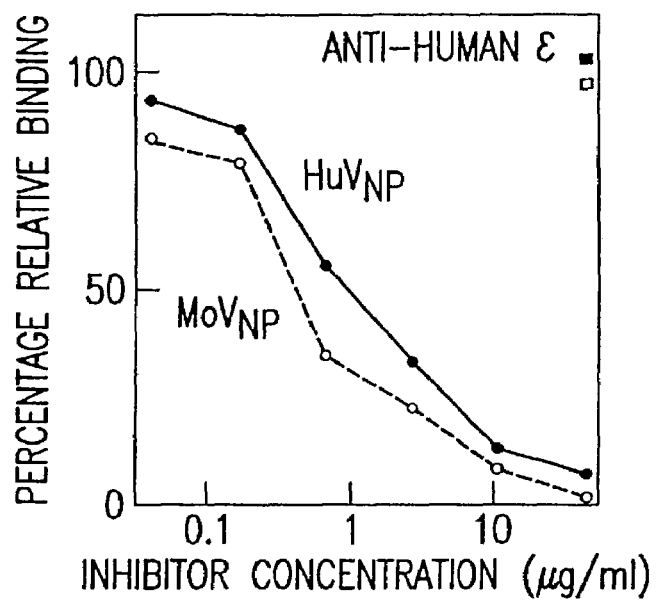
FIG. 4 shows a comparison of the results for $HuV_{NP}$-IgE and $MoV_{NP}$-IgE in binding inhibition assays.
Figure 4B:
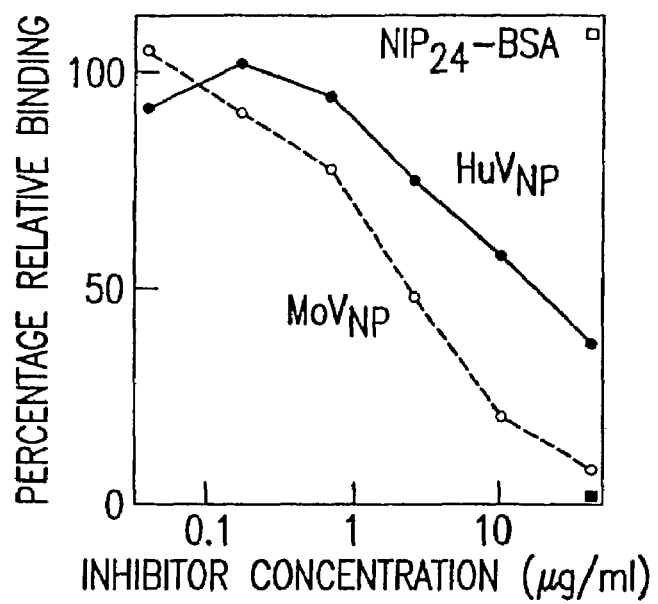
Figure 4C:
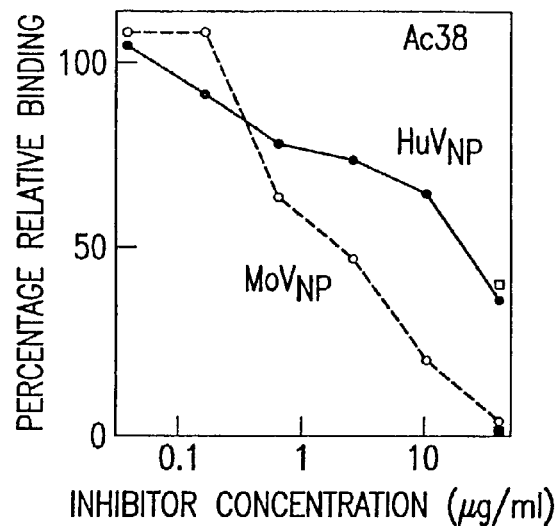
Figure 4D:
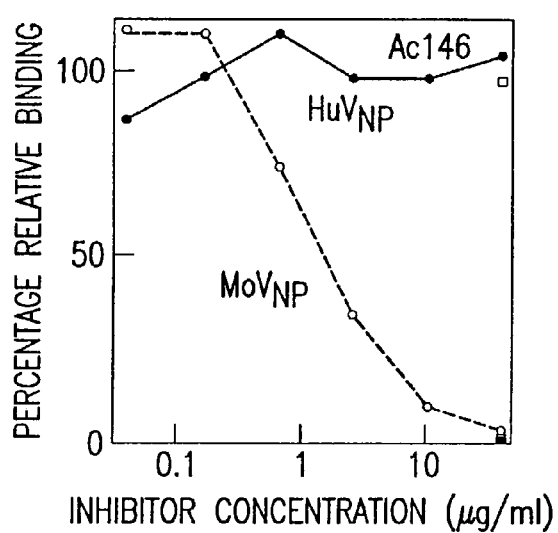

As shown in FIG. 4(d), the $HuV_{NP}$-IgE antibody has lost the $MoV_{NP}$ idiotypic determinant recognised by the antibody Ac146. Furthermore, $HuV_{NP}$-IgE also binds the Ac38 antibody less well (FIG. 4(c)), and it is therefore not surprising that $HuV_{NP}$-IgE has lost many of the determinants recognised by the polyclonal rabbit anti-idiotypic antiserum (FIG. 4(e)).

It can thus be seen that, although the $HuV_{NP}$-IgE antibody has acquired substantially all the antigen binding capacity of the mouse CDRs, it has not acquired any substantial proportion of the mouse antibody's antigenicity.

Figure 4E:
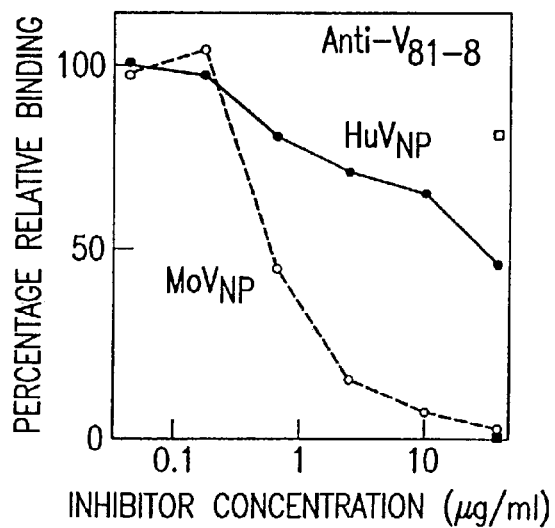

The results of FIGS. 4(d) and 4(e) carry a further practical implication. The mouse (or human) CDRs could be transferred from one set of human frameworks (antibody 1) to another (antibody 2). In therapy, anti-idiotypic antibodies generated in response to antibody 1 might well bind poorly to antibody 2. Thus, as the anti-idiotyic response starts to neutralise antibody 1 treatment could be continued with antibody 2, and the CDRs of a desired specificity used more than once.

For instance, the oligonucleotides encoding the CDRs may be used again, but with a set of oligonucleotides encoding a different set of framework regions.

The above work has shown that antigen binding characteristics can be transferred from one framework to another without loss of activity, so long as the original antibody is specific for a small hapten.

It is known that small haptens generally fit into an antigen binding cleft. However, this may not be true for natural antigens, for instance antigens comprising an epitopic site on a protein or polysaccharide. For such antigens, the antibody may lack a cleft (it may only have a shallow concavity), and surface amino acid residues may play a significant role in antigen binding. It is therefore not readily apparent that the work on artificial antigens shows conclusively that CDR replacement could be used to transfer natural antigen binding properties.

Therefore work was carried out to see if CDR replacement could be used for this purpose. This work also involved using primer-directed, oligonucleotide site-directed mutagenesis using three synthetic oligonculeotides coding for each of the mouse CDRs and the flanking parts of framwork regions to produce a variable domain gene similar to the $HuV_{NP}$ gene.

Example 2

The three dimensional structure of a complex of lysozyme and the antilysozyme antibody D1.3 (Amit et al., loc. cit.) was solved by X-ray crystallography. There is a large surface of interaction between the antibody and antigen. The antibody has two heavy chains of the mouse IgG1 class (H) and two Kappa light chains (K), and is denoted below as $H_2K_2$.

The DNA sequence of the heavy chain variable region was determined by making cDNA from the mRNA of the D1.3 hybridoma cells, and cloning into plasmid and M13 vectors. The sequence is shown in FIG. 7, in which the boxed residues comprise the three CDRs and the asterisks mark residues which contact lysozyme.

Figure 5:
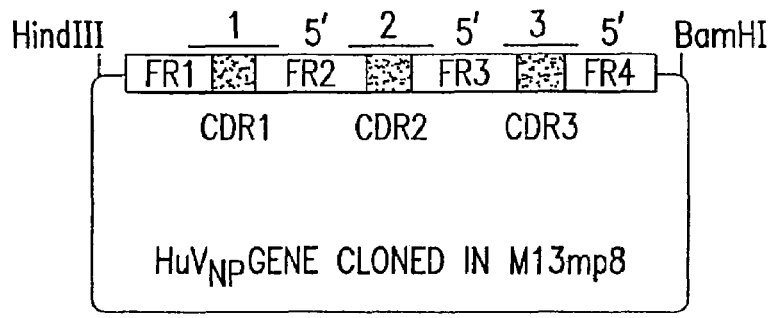
FIG. 5 shows the structure of three oligonucleotides used for site directed mutagenesis.
Figure 6:
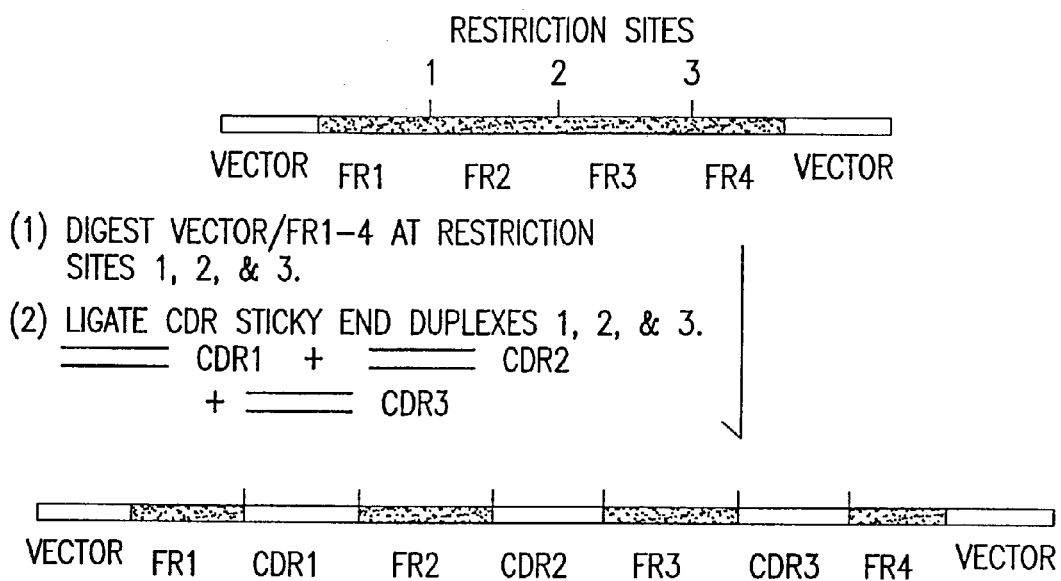
FIG. 6 shows a protocol for the construction of CDR replacements by insertion of CDR cassettes into a vector containing four framework regions fused together.
Figure 8A:
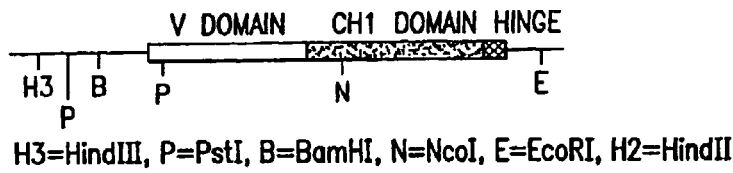
FIG. 8 shows a protocol for the cloning of the D1.3 variable domain gene.
Figure 8B:
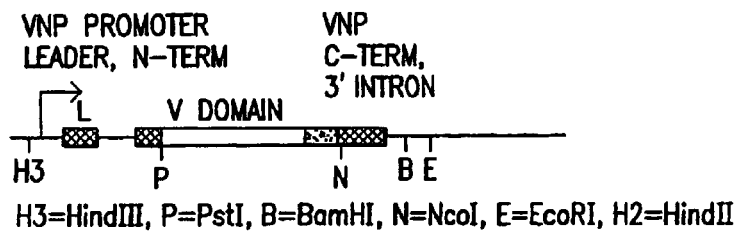
Figure 8C:
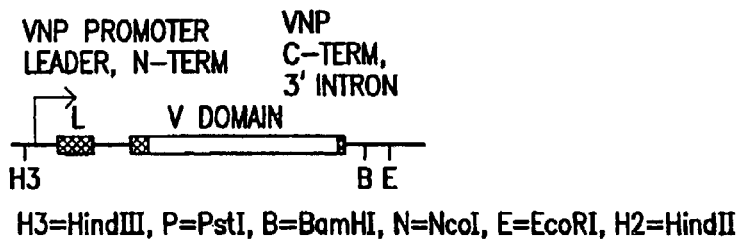
Figure 8D:
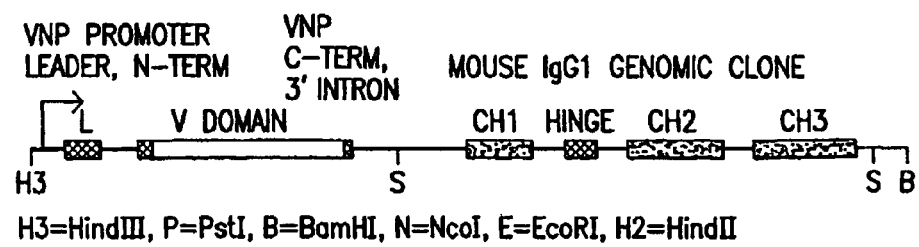

Three synthetic oligonucleotides were then designed to introduce the D1.3 $V_H$CDRs in place of the $V_H$CDRs of the $HUV_{NP}$ gene. The $Hu_{NP}$ gene has been cloned into M13mp8 as a BamHI-Hind III fragment, as described above. Each oligonucleotide has 12 nucleotides at the 5' end and 12 nucleotides at the 3' end which are complementary to the appropriate $HuV_{NP}$ framework regions. The central portion of each oligonucleotide encodes either CDR1, CDR3, or CDR3 of the D1.3 antibody, as shown in FIG. 5, to which reference is now made. It can be seen from this Figure that these oligonucleotides are 39, 72 and 48 nucleotides long respectively.

10 pmole of D1.3 CDR1 primer phosphorylated at the 5' end and annealed to lug of the M13-$HuV_{NP}$ template and extended with the Klenow fragment of DNA polymerase in the presence of T4 DNA ligase. After an oligonucleotide extension at 15° C., the sample was used to transfect *E. Coli* strain BHM71/18 mutL and plaques gridded and grown up as infected colonies.

After transfer to nitrocellulose filters, the colonies were probed at room temperature with 10 pmole of D1.3 CDR1 primer labelled at the 5' end with 30 uCi $^{32}$P-ATP. After a 3" wash at 60° C., autoradiography revealed about 20% of the colonies had hybrdidised well to the probe. All these techniques are fully described in "Oligonucleotide site-directed mutagenesis in M13" an experimental manual by P. Carter, H. Bedouelle, M. M. Y. Waye and G. Winter 1985 and published by Anglian Biotechnology Limited, Hawkins Road, Colchester, Essex CO2 8JX. Several clones were sequenced, and the replacement of $HuV_{NP}$ CDR1 by D 1.3 CDR1 was confirmed. This M13 template was used in a second round of mutagenesis with D1.3 CDR2 primer; finally template with both CDRs 1&2 replaced was used in a third round of mutagenesis with D1.3 CDR3 primer. In this case, three rounds of mutganesis were used.

The variable domain containing the D1.3 CDRs was then attached to sequences encoding the heavy chain constant regions of human IgG2 so as to produce a vector encoding a heavy chain Hu*. The vector was transfected into J558L cells as above. The antibody Hu*$_2$L$_2$ is secreted.

For comparative purposes, the variable region gene for the D1.3 antibody was inserted into a suitable vector and attached to a gene encoding the constant regions of mouse IgG1 to produce a gene encoding a heavy chain H* with the same sequence as H. The protocol for achieving this is shown in FIG. 8.

As shown in FIG. 8, the gene encoding the D1.3 heavy chain V and $C_H1$ domains and part of the hinge region are cloned into the M13mp9 vector.

The vector (vector A) is then cut with NcoI, blunted with Klenow polymerase and cut with PstI. The PStI-NcoI fragment is purified and cloned into PstI-HindII cut $MV_{NP}$ to replace most of the $MV_{NP}$ coding sequences. The $M_{VNP}$ vector comprises the mouse variable domain gene with its promoter, 5' leader, and 5' and 3' introns cloned into M13mp9. This product is shown as vector B in FIG. 8.

Using site directed mutagenesis on the single stranded template of vector B with two primers, the sequence encoding the N-terminal portion of the $C_H1$ domain and the PstI site near the N-terminus of the V domain are removed. Thus the V domain of D1.3 now replaces that of $V_{NP}$ to produce vector C of FIG. 8.

Vector C is then cut with HindIII and BamHI and the fragment formed thereby is inserted into HindIII/BamHI cut M13mp9. The product is cut with Hind III and SacI and the fragment is inserted into PSV-$V_{NP}$ cut with Hind III/SacI so as to replace the $V_{NP}$ variable domain with the D1.3 variable domain. Mouse IgG1 constant domains are cloned into the vector as a SacI fragment to produce vector D of FIG. 8.

Vector D of FIG. 8 is transfected into J558L cells and the heavy chain H* is secreted in association with the lambda light chain L as an antibody $H*_2L_2$.

Separated K or L light chains can be produced by treating an appropriate antibody (for instance D1.3 antibody to produce K light chains) with 2-mercaptoethanol in guanidine hydrochloride, blocking the free interchain sulphydryls with iodoacetamide and separating the dissociated heavy and light chains by HPLC in guanidine hydrochloride.

Different heavy and light chains can be reassociated to produce functional antibodies by mixing the separated heavy and light chains, and dialysing into a non-denaturing buffer to promote re-association and refolding. Properly reassociated and folded antibody molecules can be purified on protein A-sepharose columns. Using appropriate combinations of the above procedures, the following antibodies were prepared.

| | |
|---|---|
| $H_2K_2$ | (D1.3 antibody) |
| $H*_2L_2$ | (D1.3 heavy chain, lambda light chain) |
| $H*_2K_2$ | (recombinant equivalent of D1.3) |
| $Hu*_2L_2$ | ("humanised" D1.3 heavy chain, lambda light chain) |
| $Hu*_2K_2$ | ("humanised" D1.3) |

The antibodies containing the lambda light chains were not tested for antigen binding capacity. The other antibodies were, and the results are shown in Table 2.

TABLE 2

| Antibody | Dissociation constant for lysozyme (nM) |
|---|---|
| D1.3 ($H_2K_2$) | 14.4 |
| D1.3 ($H_2K_2$) (reassociated) | 15.9, 11.4 |
| recombinant D1.3 ($H*_2K_2$) (reassociated) | 9.2 |
| "humanised" D1.3 ($Hu*_2K_2$) (reassociated) | 3.5, 3.7 |

The affinity of the antibodies for lysozyme was determined by fluoresecent quenching, with excitation at 290 nm and emission observed at 340 nm. Antibody solutions were diluted to 15–30 ug/mg in phosphate buffered saline, filtered (0.45 um-cellulose acetate) and titrated with hen eggwhite lysozyme. There is quenching of fluoresence on adding the lysozyme to the antibody (greater than 100% quench) and data were fitted by least squares to an equation describing tight binding inhibition (I. H. Segal in Enzyme Kinetics, p 73–74, Wiley, New York 1975). This data suggests that the binding of the "humanised" antibody to lysozyme is tighter than in the original D1.3 antibody. Subsequent results suggest that the affinities of the "humanised" and mouse antibodies are both less than 5 nM with 2 mol of lysozyme molecules binding 1 mol of antibody: see Verhoeyen, M., Milstein, C. and Winter, G., Science, 239, 1534–1536 (1988). Although the work described in Verhoeyen et al. suggests that the reshaped antibody may have a weaker affinity for lysozyme than the original mouse antibody it is clear that the "humanised" antibody binds lysozyme effectively and with a comparable affinity to D1.3. (within a factor of 10).

Further work on fully "humanised" antibody to lysozyme is discussed below, in Example 4.

Example 3

Further work has been carried out with an antibody to the antigen Campath-1, which is potentially of great therapeutic use, in which both light and heavy chain variable domains were reshaped. In this case, transfer of the CDRs only resulted in production of a reshaped antibody which bound poorly to the antigen as compared with the original antibody. A single mutation in the framework produced greatly enhanced binding affinity.

The Campath-1 antigen is strongly expressed on virtually all human lymphocytes and monocytes, but is absent from other blood cells including the hemopoietic stem cells (Hale, G., Bright, S., Chumbley, G., Hoang, T., Metcalf, D., Munro, A. J. & Waldmann, H. Blood 62, 873–882 (1983)). A series of antibodies to Campath-1 have been produced, including rat monoclonal antibodies of IgM, IgG2a, and IgG2c isotypes (Hale, G., Hoang, T., Prospero, T., Watts, S. M. '& Waldmann, H. Mol. Biol. Med. 1, 305–319 (1983)) and more recently IgG1 and IgG2b isotypes have been isolated as class switch variants from the IgG2a secreting cell line YTH 34.5HL (Hale, G., Cobbold, S. P., Waldmann, H., Easter, G., Matejtschuk, P. '& Coombs, R. R. A. J. Immunol. Meth. 103, 59–67 (1987)). All of these antibodies with the exception of the rat IgG2c isotype are able to lyse efficiently human lymphocytes with human complement.

In addition, the IgG2b antibody YTH 34.5HL-G2b, but not the other isotypes, is effective in antibody dependent cell mediated cytotoxicity (ADCC) with human effector cells (Hale et al, 1987, loc. cit.). These rat monoclonal antibodies have found important application in the context of immunosuppression, for control of graft-versus-host disease in bone marrow transplantation (Hale et al, 1983, loc. cit.); the management of organ rejection (Hale, G., Waldmann, H., Friend, P. '& Calne, R. Transportation 42, 308–311 (1986)); the prevention of marrow rejection and in the treatment of various lymphoid malignancies (Hale, G., Swirsky, D. M., Hayhoe, F. G. J. & Waldmann, H. Mol. Biol. Med. 1, 321–334 (1983)). For in-vivo use, the IgG2b antibody YTH 34.5HL-G2b seems to be the most effective at depleting lymphocytes, but the use of any of the antibodies in this group is limited by the antiglobulin response which can occur within two weeks of the initiation of treatment (Hale, Swirsky et al, 1983, loc. cit.).

The sequences of the heavy and light chain variable domains of rat IgG2a Campath-1 antibody YTH 34.5HL were determined by cloning the cDNA (FIG. 9), and the hypervariable regions were identified according to Kabat et al, loc. cit. Sequence information is given in the lower lines of FIG. 9, with the CDRs identified in boxes.

In the heavy chain variable domain there is an unusual feature in the framework region. In most known heavy chain sequences Pro(41) and Leu(45) are highly conserved: Pro (41) helps turn a loop distant from the antigen binding site and Leu(45) is in the beta bulge which forms part of the conserved packing between heavy and light chain variable domains (Chothia, C., Novotny, J., Bruccoleri, R. '& Karplus, M. J. Mol. Biol. 186, 651–663 (1985)). In YTH 34.5HL these residues are replaced by Ala(41) and Pro(45), and presumably this could have some effect on the packing of the heavy and light chain variable domains.

Working at the level of the gene and using three large mutagenic oligonucleotides for each variable domain, in a single step the hypervariable regions of YTH 34.5HL were mounted on human heavy or light chain framework regions taken from the crystallographically solved proteins NEW for the heavy chain (Saul, F. A., Amzel, M. '& Poljak, R. J. J. Biol. Chem. 253, 585–597 (1978)) and from a protein based closely on the human myeloma protein REI for the light chain (Epp, O., Colman, P., Fehlhammer, H., Bode, W., Schiffer, M. '& Huber, R. Eur. J. Biochem. 45, 513–524 (1974)). The NEW light chain was not used because there is a deletion at the beginning of the third framework region of the NEW light chain. The resulting reshaped heavy chain variable domain HuVHCAMP is based on the HuVHNP gene (Kabat et al, loc. cit. and Jones, P. T., Dear, P. H., Foote, J., Neuberger, M. S. '& Winter, G. Nature 321, 522–525 (1986)) with the framework regions of human NEW alternating with the hypervariable regions of rat YTH 34.5HL. The reshaped light chain variable domain HuVLCAMP is a similar construct, except with essentially the framework regions of the human myeloma protein REI, with the C-terminal and the 3' non-coding sequence taken from a human $J_k$-region sequence (Hieter, P. A., Max, E. E., Seidmann, J. G., Maizel, J. V. Jr '& Leder, P. Cell 22, 197–207 (1980)). Sequence information for the variable domain of the reshaped antibody is given in the upper lines in FIG. 9. The sequences of oligonucleotide primers are given and their locations on the genes are also marked in FIG. 9.

Considering the above in further detail, mRNA was purified (Kaartinen, M., Griffiths, G. M., Hamlyn, P. H., Markham, A. F., Karjalainen, K., Pelkonen J. L. T., Makela, O. '& Milstein, C. J. Immunol. 130, 320–324 (1983)) from the hybridoma clone YTH 34.5HL (gamma 2a, $k^b$), and first strand cDNA made by priming with oligonucleotides complementary to the 5' end of the CH1 (oligonucleotide I) and the Ck exons (oligonucleotide II). cDNA was cloned and sequenced as described in Gubler, U. '& Hoffman, B. J. Gene 25, 263–269 (1983) and Sanger, F., Nicklen, S. A. '& Coulson, A. R. Proc. natl. Acad. Sci USA 74, 5463–5467 (1977).

For expression of the rat heavy chain variable domain RaVHCAMP, two restriction sites (XbaI and SalI) were introduced at each end of the cDNA clone in M13 using mutagenic oligonucleotides III and V respectively, and the XbaI-SalI fragment excised. Simultaneously, the corresponding sites were introduced into the M13-HuVHNP gene using oligonucleotides IV and VI, and the region between the sites exchanged. The sequence at the junctions was corrected with oligonucleotides VII and VIII, and an internal BamHI site removed using the oligonucleotide IX, to create the M13-RaVHCAMP gene. The encoded sequence of the mature domain is thus identical to that of YTH 34.5HL.

The reshaped heavy chain variable domain (HuVHCAMP) was constructed in an M13 vector by priming with three long oligonucleotides simultaneously on the single strand containing the M13-HuVHNP gene (see Kabat et al, loc. cit and Jones et al, loc. cit).). The mutagenesis techniques used were similar to those described in Carter et al loc. cit, using the host 71-18 mutL and without imposing strand selection. Each oligonucleotide (X, XI and XII) was designed to replace each of the hypervariable regions with the corresponding region from the heavy chain of the YTH 34.5HL antibody.

Colony blots were probed initially with the oligonucleotide X and hybridisation positives were sequenced: the overall yield of the triple mutant was 5%. Ser27 to Phe and Ser27 to Phe, Ser30 to Thr mutants (to be described below) of M13mpB-HuVHCAMP were made with the mixed oligonucleotide XIII.

The reshaped light chain variable domain (HuVLCAMP) was constructed in an M13 vector from a gene with framework regions based on human REI. As above, three long oligonucleotides (XIV, XV, and XVI) were used to introduce the hypervariable regions of the YTH 34.5HL light chain.

Construction of the humanised light chain variable domain is described in greater detail in the following seven paragraphs.

(1) The "humanised" light chain variable domain (HuVLCAMP) was constructed in three stages, utilising a "humanised" light chain variable domain (HuVLLYS) which had been constructed for other purposes.

(a) The first stage involved the gene synthesis of a "humanised" light chain variable domain gene (HuVLLYS°). The HuVLLYS° gene incorporates human framework regions identical to the most common residue in each position in the Kabat alignment of the human kappa subgroup I, except for residues 97–108, which were identical to those in the human J1 fragment described in Heiter, P., Maizel, J '& Leder, P. J. Biol. Chem. 257, 1516–1522 (1982). The sequences of the framework regions are very similar to the crystallographically solved light chain structure REI. The CDRs in HuVLLYS° were identical to those in the mouse antilysozyme antibody (D1.3) light chain (unpublished). A 30 bp sequence, identical to the sequence following the genomic JI segment, was introduced to the 3' side of residue 108. BamH1 and EcoRI restriction sites were introduced at the 3' end of the synthetic gene, and a PstI site at th 5' end. The gene synthesis of HuVLLYS° is described in paragraphs (2) to (5) below, and the sequence of the gene and the derived amino acid sequence is given in FIG. 10.

(b) The second stage involved the introduction of the HuVLLYS° gene in place of the heavy chain variable domain in the vector M13-MOVHNP and this is described in paragraphs 6 and 7 below. Thus the light chain variable domain utilises the promoter and signal sequence of a heavy chain variable domain: at the 3' end of the gene the sequence is derived from the human light chain J1 segment as described in paragraph (1a). The sequence of the HuVLLYS gene and the derived amino acid sequence is given in FIG. 11.

(c) The third stage involved the conversion of HuVLLYS to a "humanised" light chain variable domain with the CDRs of Campath-1 specifity.

2. For the synthesis of the HuVLLYS° gene, three blocks of oligonucleotides (PK1-5, KK1-5 and KE1-8 in the table in paragraph 3 below were cloned separately into M13 vectors, and sequenced. Each cloned block was excised and ligated together into M13mp19 to create the HuVLLYS° gene.

3. Oligonucleotides listed below were produced on an Applied Biosystems 380B synthesizer. Each oligonucleotide was size-purified, 10 nmol being subjected to electrophoresis on a 20×40 cm 12% polyacrylamide, 7M urea gel, eluted from the gel by dialysis against water, and lyophilized. For gene synthesis or mutagenesis, a 50 pmol aliquot of each purified oligonucleotide was phosphorylated in a 20 ul reaction mixture with 50 mM Tris-Cl (pH 8.0), 10 mM MgCl$_2$, 5 mM dithiothreitol, 1 mM ATP, and 5 units of polynucleotide kinase, incubated at 37° for 30 minutes. When used as hybridization probes, gel-purified oligonucleotides were phosphorylated in a similar fashion, except on a 15 pmol scale with an excess of $^{32}$P labeled ATP.

| name | sequence (5'-3') | SEQ ID NO. |
|---|---|---|
| PK1 | GACATCCAGATGACCCAGAGCCCAAGCAGCCTGAGCG CCAGCGTGGGT | 1 |
| PK2 | GACAGAGTGACCATCACCTGTAGAGCCAGCGGTAACA TCCACAACTACCTGGCTTGGTAC | 2 |
| PK3 | CAAGCCAGGTAGTTGTGGATGTTACCGCTGGCTCTACA GGTGAT | 3 |
| PK4 | GGTCACTCTGTCACCCACGCTGGCGCTCAGGCT | 4 |
| PK5 | GCTTGGGCTCTGGGTCATCTGGATGTCTGCA | 5 |
| KK1 | CAGCAGAAGCCAGGTAAGGCTCCAAAGCTGCTGATCT ACTACACCACCA | 6 |
| KK2 | CCCTGGCTGACGGTGTGCCAAGCAGATTCAGCGGTAGC GGTAGCGGTAC | 7 |
| KK3 | CGCTACCGCTACCGCTGAATCTGCT | 8 |
| KK4 | TGGCACACCGTCAGCCAGGGTGGTGGTGTAGTAGATC AGC | 9 |
| KK5 | AGCTTTGGAGCCTTACCTGGCTTCTGCTGGTAC | 10 |
| KE1 | CGACTTCACCTTCACCATCAGCAGCCTCCAGCCAGAGG ACATCGCCACCTACTACTGCC | 11 |
| KE2 | AGCACTTCTGGAGCACCCCAAGGACGTTCGGCCAAGG GACCAAGGTGGA | 12 |
| KE3 | AATCAAACGTGAGTAGAATTTAAACTTTGCTTCCTCAG TTGGATCCTAG | 13 |
| KE4 | AATTCTAGGATCCAACTGAGGAAGCAAAGTTTAAA | 14 |
| KE5 | TTCTACTCACGTTTGATTTCCACCTTGGTCCCTT | 15 |
| KE6 | GGCCGAACGTCCTTGGGGTGCTCCAGAAGTGCTGGCA GTAGTAG | 16 |
| KE7 | GTGGCGATGTCCTCTGGCTGGAGGCT | 17 |
| KE8 | GCTGATGGTGAAGGTGAAGTCGGTAC | 18 |
| PK0 | TCATCTGGATGTCGGAGTGGACACCT | 19 |

4. The construction of individual blocks is described for the PK1-5 block, but KK1-5 and KE1-8 blocks were cloned as KpnI-KpnI and KpnI-EcoRI fragments respectively in a similar way. 4 ul portions of each oligonucleotide PK1, PK2, PK3, PK4 and PK5, kinased as in paragraph 3, were combined and annealed at 80° C. for 5 minutes, 67° C. for 30 minutes, and allowed to cool to room temperature over the span of 30 minutes, 0.1 ul of this annealing mix was ligated with 20 ng of PstI/KpnI digested M13-mp19, in 10 ul 50 mM Tris-Cl (pH7.5), 10 mM MgCl$_2$, 10 mM dithiothreitol, 1 mM ATP, 120 units T4 DNA ligase (Biolabs), and incubated 12 hours at 15° C. The ligation mix was used to transfect competent *E. coli* strain BMH 71-18, plated with BCIG and IPTG, and a clone containing the complete PstI-KpnI insert was identified.

5. The three cloned blocks were excised from 10 ug double-stranded replicative form of the thee M13 vectors, by digestion with PstI/KpnI (block PK1-5), KpnI (block KKI-5) and KpnI/EcoRI (block KE1-8). The inserts were separated from the vector by electrophoresis on a 20×20 cm 12% polyacrylamide gel, eluted from the gel slices with 0.5 M NH$_4$OAc, 10 mM Mg (OAc)$_2$, 0.1 mM EDTA, 0.1% SDS, and purified by phenol extraction and ethanol precipitation. All three fragments were ligated to PstI/EcoRI cut M13-mp19. 200 white plaques were transferred by toothpick to a fresh 2xTY plate, and grown as a grid of infected colonies. The plate was blotted with nitrocellulose filters, which were then treated with 0.5 M NaOH, followed by 1M Tris-Cl (pH7.5), and baked 1 hr at 80° C. under vacuum. The filters were washed at 67° C. in 3× Denhardt's solution, 2×SSC, 0.07% SDS, followed by 6×SSC at room temperature. Filters were then probed with the radiolabeled oligonucleotides KK3 or KK4 in 3 ml of 6×SSC at 37°. Following hybridization with both olignucleotides, positive colonies were picked for DNA sequencing. A phage clone containing correctly assembled blocks was designated M13-HuVLLYS°.

6. To introduce the-HuVLLYS° gene in place of the heavy chain variable domain in the vector M13-MOVHNP (described in Jones et al, loc. cit) as MV$_{NP}$ with HindII site at the 3' end of the reading frame), double-stranded replicative form DNA of phages M13-HuVLLYS° and M13-MOVHNP were prepared and digested with PstI and BamHI. The insert of M13-HuVLLYS was isolated on a polyacrylamide gel, and the vector portion of M13-MOVHNP was isolated on an agarose gel. The purified fragments were ligated and transfected into *E. coli* strain BMH71-18, and the resulting plaques probed with oligonucleotide KK3 to identify the insert. The clone was designated M13-HuVLLYS*.

7. In the M13-HuVLLYS* gene, to join the signal sequence of MOVHNP correctly to the 5' end of the HuV-LLYS° gene (at the PstI site), single stranded DNA was prepared and altered by oligonucleotide directed mutagenesis with the primer PKO—see paragraph (3) for sequence. The mutant clone was designated M13-HuVLLYS.

Figure 12:
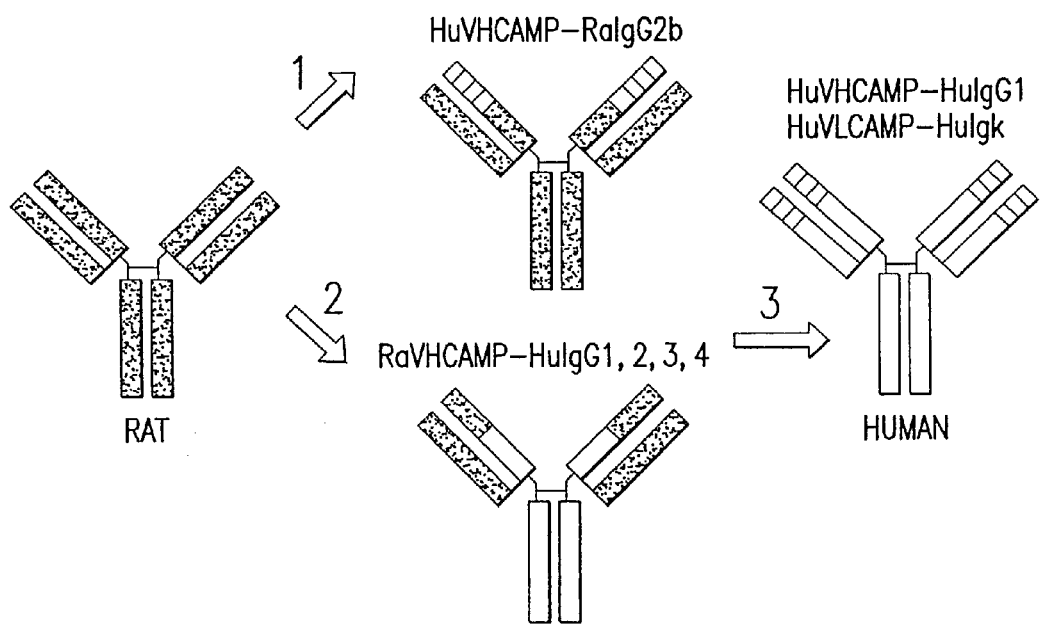
FIG. 12 illustrates a strategy for producing a reshaped human antibody having rat CDRs.

As previously mentioned the Campath-1 light chain variable domain was derived from the HuVLLYS domain, and the reshaped human heavy (HuVHCAMP) and light (HuV-LCAMP) chain variable domains were then assembled with constant domains in three stages as illustrated in FIG. 12. In FIG. 12 sequences of rat origin are marked in black, and those of human origin in white. The recombinant heavy and light chains are also marked using a systematic nomenclature.

The illustrated procedure permits a step-wise check on the reshaping of the heavy chain variable domain (stage 1), the selection of the human isotype (stage 2), and the reshaping of the light chain variable domain and assembly of human antibody (stage 3). The vector constructions were genomic, with the variable domains excised from the M13 vectors and cloned as HindIII-BamHI fragments and the constant domains as BamHI-BamHI fragments in either pSVgpt (heavy chain) (Mulligan, R. C. '& Berg, P. Proc. natl. Acad. Sci USA 78, 2072–2076 (1981)) or pSVneo (light chain) (Southern, P. J. '& Berg, P. J. Mol. Appl. Genetics 1, 327–341 (1981)) vectors. The heavy chain enhancer was included to the 5' side of the variable domain, and expression of both light and heavy chains was driven from heavy chain promoter and the heavy chain signal sequence.

The human gamma 1 (Takahashi, N., Ueda, N. S., Obata, M., Nikaido, T. & Honjo, T. Cell 29, 671–679 (1982)), gamma 2 (Flanagan, J. G. & Rabbits, T. H. Nature 300, 709–713 (1982)), gamma 3 (Huck, S., Fort, P., Crawford, D. H., Lefranc, M.-P. & Lefranc, G. Nucl. Acid Res. 14, 1779–1789 (1986), gamma 4 (Clark, M. & Waldmann, H. J.N.C.I. (in press) and K (Heiter et al, loc. cit) constant domains, and the rat gamma 2b (Bruggemann, M., Free, J., Diamond, A., Howard, J., Cobbold, S. & Waldmann, H. Proc. natl. Acad. Sci. USA 83, 6075–6079 (1986)) constant domains were introduced as BamHI-BamHI fragments. The following plasmids were constructed and transfected into lymphoid cell lines by electroporation (Potter, H., Weir, L. & Leder, P. Proc. natl. Acad. Sci. USA 81, 7161–7163 (1984)). In stage 1, the pSVgpt vectors HuVHCAMP-RaIgG2B, and also two mutants for reasons to be explained below, HuVHCAMP(Ser27 to Phe)-RaIgG2B, HuVHCAMP(Ser27 to Phe, Ser30 to Thr)-RaIgG2B) were introduced into the heavy chain loss variant of YTH34.5HL. In stage 2, the pSVgpt vectors RaVHCAMP-RaIgG2B, RaVHCAMP-HuIgG1, RaVHCAMP-HuIgG2, RaVHCAMP-HuIgG3, RaVHCAMP-HuIgG4 were transfected as described above. In stage 3, the pSV-gpt vector Hu(Ser27-Phe, Ser30-Thr)VHCAMP-HuIgG1 was cotransfected with the pSV-neo vector HuVLCAMP-HuIgK into the rat myeloma cell line Y0 (Y B2/3.0 Ag 20) (Galfre, G. & Milstein, C. Meth. Enzymol. 73, 1–46 (1981)). In each of the three stages, clones resistant to mycophenolic acid were selected and screened for antibody production by ELISA assays. Clones secreting antibody were subcloned by limiting dilution (for Y0) or the soft agar method (for the loss variant) and assayed again before 1 liter growth in roller bottles.

Heavy Chain Variable Domain

In stage 1, the reshaped heavy chain variable domain (HuVHCAMP) was attached to constant domains of the rat isotype IgG2b and transfected into a heavy chain loss variant of the YTH34.5 hybridoma. The loss variant carries two light chains, one derived from the Y3 fusion partner (Galfre et al., loc. cit). The cloned rat heavy chain variable domain (RaVHCAMP) was also expressed as above.

Antibodies were harvested at stationary phase and concentrated by precipitation with ammonium sulphate, followed by ion exchange chromatography on a Pharmacia MonoQ column. The yields of antibody were measured by an ELISA assay directed against the rat IgG2b isotype, and each adjusted to the same concentration (Clark and Waldmann loc. cit).

The HuVHCAMP and RaVHCAMP antibodies—all of the rat IgG2b isotype—were compared in a direct binding assay to the Campath-1 antigen (obtained from a glycolipid extract from human spleen), and also in complement lysis of human lymphocytes. For measuring the binding to antigen, the partially purified Campath-1 antigen was coated onto microtitre wells. Bound antibody was detected via a biotin labelled anti-rat IgG2b monoclonal antibody (Clark & Waldmann loc. cit), developed with a streptavidin-peroxidase conjugate (Amersham plc). Complement lysis of human lymphocytes with human serum as the complement source was as described in Hale, Hoang et al (1983) loc. cit. For both binding and complement assays, the titres for the antibodies were determined by fitting the data to a sigmoid curve by a least squares iterative procedure (Hale, Hoang et al (1983) loc. cit), and the concentration of antibody giving 50% maximal binding or lysis was noted.

The results are given in Table 3.

TABLE 3

Reshaping the heavy chain variable domain

| heavy chain variable domain | Concentration of antibody in ug/ml at 50% binding or lysis | |
| --- | --- | --- |
| | antigen binding | complement lysis |
| RaVHCAMP | 0.7 | 2.1 |
| HuVHCAMP | 27.3 | (*) |
| HuVHCAMP (Ser27 to Phe) | 1.8 | 16.3 |
| HuVHCAMP (Ser27 to Phe, Ser30 to Thr) | 2.0 | 17.6 |

(*) Complement lysis with the HuVHCAMP variable domain was too weak for the estimation of lysis titre.

Compared with the original rat antibody, or the engineered equivalent, the antibody with the reshaped heavy chain domain HuVHCAMP bound poorly to the Campath-1 antigen and was weakly lytic. This suggested an error in the design of the reshaped domain.

There are several assumptions underlying the transfer of hypervariable loops from one antibody to another, and in particular that the antigen binds mainly to the hypervariable regions. These are defined as regions of sequence (Kabat et al, loc. cit) or structural (Chothia, C. & Lesk, A. J. Mol. Biol. 196, 901–917 (1987)) hypervariability, and the locations of hypervariable regions are similar by either criterion, except for the first hypervariable loop of the heavy chain. By sequence the first hypervariable loop extends from residues 31 to 35 (Kabat et al, loc. cit) and by structure from residues 26 to 32 (Chothia et al, (1987) loc. cit). Residues 29 and 30 form part of the surface loop, and residue 27 which is phenylalanine or tyrosine in most sequences including YTH34.5HL, helps pack against residues 32 and 34.

Figure 13:
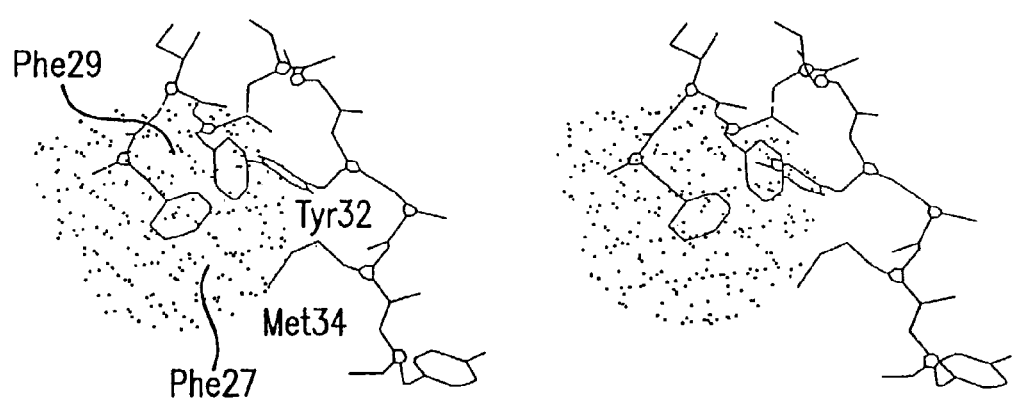
FIG. 13 illustrates loop Phe 27 to Tyr 35 in the heavy chain variable domain of the human myeloma protein KOL.

By way of illustration, see FIG. 13 which illustrates loop Phe27 to Tyr35 in the heavy chain variable domain of the human myeloma protein KOL which is crystallographically solved (Marquardt, M., Deisenhofer, J., Huber, R. & Palm, W. J. Mol. Biol. 141, 368–391 (1980)). The backbone of the hypervariable region according to Kabat et al, (loc. cit.) is highlighted, and a 200% van der Waal surface is thrown around Phe27 to show the interactions with Tyr32 and Met34 of the Kabat hypervariable region. In the rat YTH34.5HL heavy chain, these three side chains are conserved, but in HuVHCAMP, Phe27 is replaced by Ser: this is because, unlike most human heavy chains, in NEW the phenylalanine is replaced by serine, which would be unable to pack in the same way as phenylalanine. To restore the packing of the loop, a Ser(27) to Phe mutation was made in HuVHCAMP, and also a double mutation Ser(27) to Phe, Ser(30) to Thr (as mentioned above).

The two mutants showed a significant increase in binding to CAMPATH-1 antigen and lysed human lymphocytes with human complement. See the results given in Table 3. Thus the affinity of the reshaped antibody could be restored by altering the packing between the hypervariable regions and the framework by a single Ser(27) to Phe mutation. This suggests that alterations in the "Kabat" framework region can enhance the affinity of the affinity of the antibody, and extends previous work in which an engineered change in the hypervariable region yielded an antibody with increased affinity (Roberts, S., Cheetham, J. C. & Rees, A. R. Nature 328, 731–734 (1987)).

Heavy Chain Constant Domains

In stage 2 (FIG. 12), the rat heavy chain variable domain was attached to constant domains of the human isotypes IgG1, 2, 3, and 4, and transfected into the heavy chain loss variant of the YTH34.5 hybridoma.

Antibody was harvested from cells in stationary phase, concentrated by precipitation with ammonium sulphate and desalted into phosphate buffered saline (PBS). Antibodies bound to the Campath-1 antigen coated on microtitre plates, were assayed in ELISA directed against the rat k light chain (Clark & Waldmann loc cit), and adjusted to the same concentration. The antibodies were assayed in complement lysis (as described above) and ADCC with activated human peripheral blood mononuclear cells (Clark & Waldmann loc. cit and Hale, G. Clark, M. & Waldmann, H. J. Immunol. 134, 3056–3061 (1985)). Briefly, $5 \times 10^4$ human peripheral blood cells were labelled with $^{51}Cr$ and incubated for 30 minutes at room temperature with different concentrations of antibody. Excess antibody was removed and a 20 fold excess of activated cells added as effectors. After 4 hours at 37° C. death was estimated by $^{51}$Cr release.

Figure 14A:
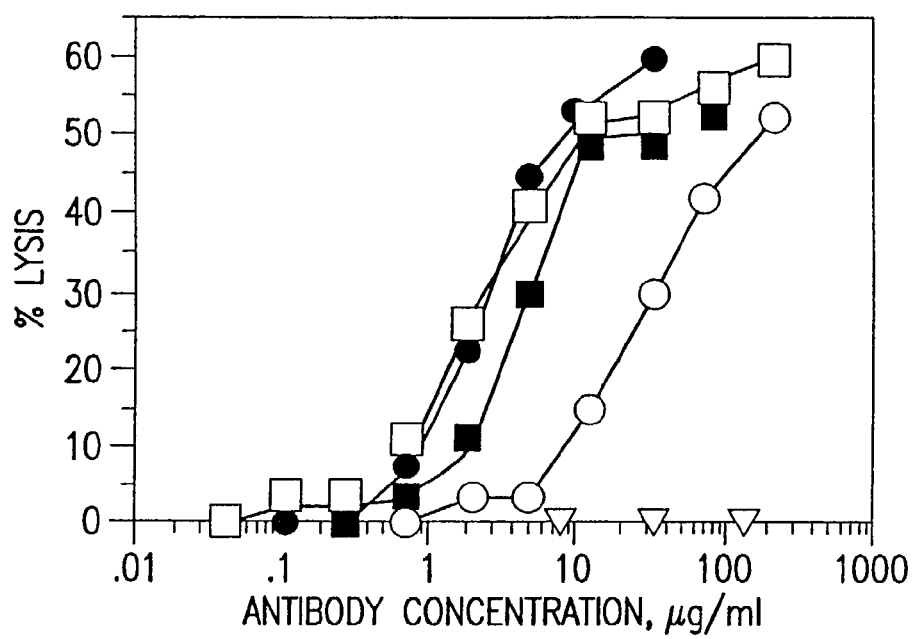
FIG. 14 illustrates the results of complement lysis and ADCC for various antibodies.
Figure 14B:
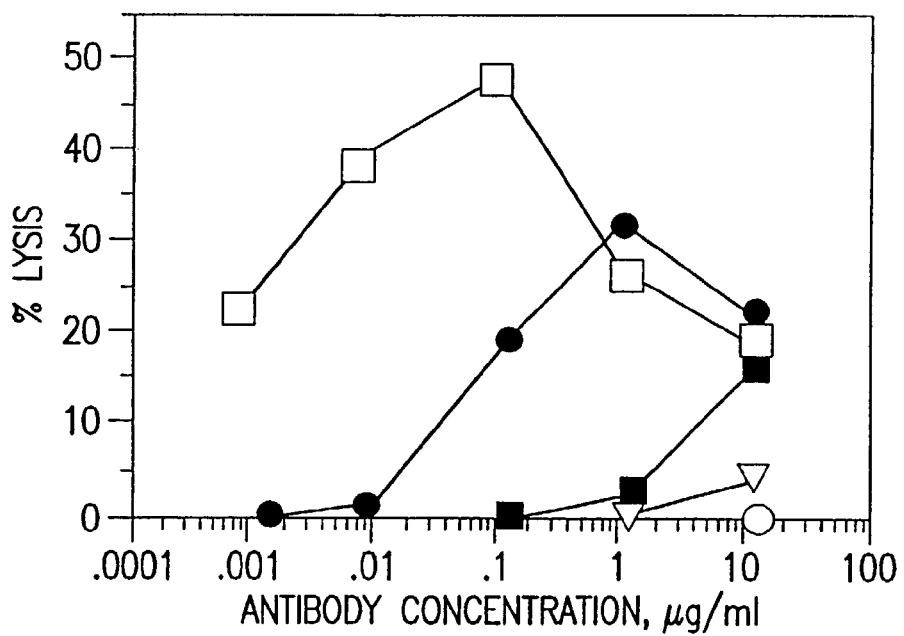

The results are shown in FIG. 14, in which the results for rat heavy chain variable domain attached to different human isotypes are represented as follows:

| | |
|---|---|
| IgG1 | empty squares |
| IgG2 | empty circles |
| IgG3 | solid squares |
| IgG4 | empty triangles |

Results of lysis with the antibody YTH34.5HL are represented by solid circles.

In complement lysis (FIG. 14*a*), the human IgG1 isotype proved similar to the YTH34.5HL-G2b, with the human IgG3 isotype less effective. The human IgG2 isotype was only weakly lytic and the IgG4 isotype non-lytic. In ADCC (FIG. 14*b*) the human IgG1 was more lytic than the YTH34.5HL-G2b antibody. The decrease in lysis at higher concentration of the rat IgG2b and the human IgG1 antibody is due to an excess of antibody, which causes the lysis of effector cells. The human IgG3 antibody was weakly lytic, and the IgG2 and IgG4 isotypes were non-lytic.

The human IgG1 isotype was therefore suitable for a reshaped antibody for therapeutic use. Other recent work also suggests the IgG1 isotype as favoured for therapeutic application. When the effector functions of human isotypes were compared using a set of chimaeric antibodies with an anti-hapten variable domain, the IgG1 isotype appeared superior to the IgG3 in both complement and cell mediated lysis (Bruggemann, M., Williams, G. T., Bindon, C., Clark, M. R., Walker, M. R., Jefferis, R., Waldmann, H. & Neuberger, M. S. J. Exp. Med. (in press). Furthermore, of two mouse chimaeric antibodies directed against cell surface antigens as tumour cell markers, with human IgG1 or IgG3 isotypes, only the IgG1 isotype mediated complement lysis (Liu, A. Y., Robinson, R. R., Hellstrom, K. E., Murray, E. D. Jr., Cheng, C. P. & Hellstrom, I. Proc. natl. Acad. Sci. USA 84, 3439–3443 (1987) and Shaw, D. R., Khasaeli, M. B, Sun, L. K., Ghraeyeb, J., Daddona, P. E., McKinney, S. & Lopuglio, A. F. J, Immunol. 138, 4534–4538 (1987)).

Light Chain

In stage 3 (FIG. 12), the reshaped heavy chain was completed, by attaching the reshaped HuVHCAMP (Ser27 to Phe, Ser30 to Thr) domain to the human IgG1 isotype. The reshaped light chain domain HuVHCAMP was attached to the human Ck domain. The two vectors were cotransfected into the non-secreting rat Y0 myeloma line.

Antibody HuVHCAMP (Ser27 to Phe, Thr30 to Ser)-HuIGG1, HuVLCAMP-HuIGK was purified from supernatants of cells in stationary phase by affinity chromatography on protein A Sepharose. The antibody was at least 95% (by wt) pure. The yield (about 10 mg/l) was measured spectrophotometrically. Complement and ADCC assays were performed as described in connection with FIG. 14.

The results are shown in FIG. 15, in which the results for reshaped human antibodies are represented by squares and those for rat YTH34.5HL antibodies are represented by solid circles.

Figure 15A:
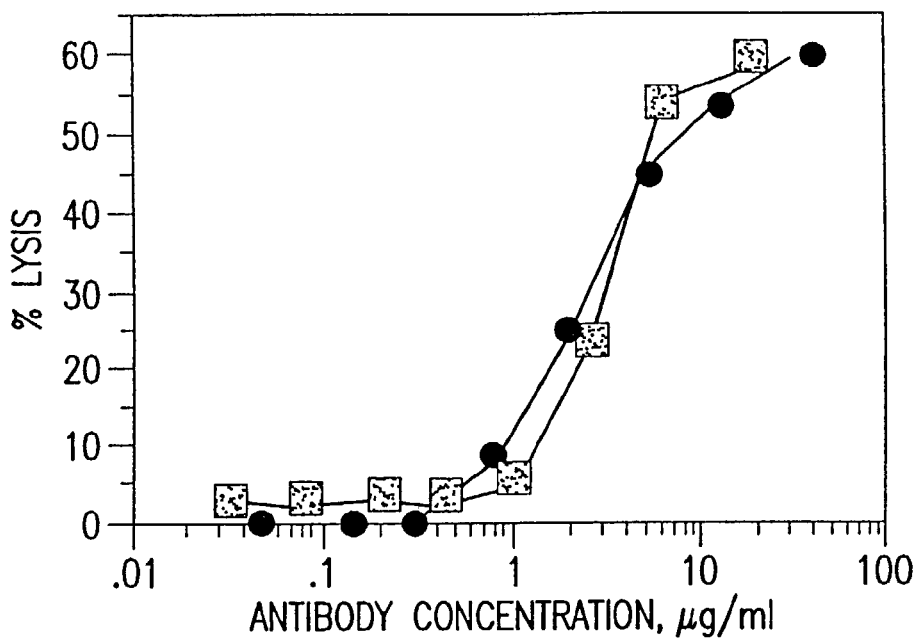
FIG. 15 illustrates the results of complement lysis and ADCC of various further antibodies.
Figure 15B:
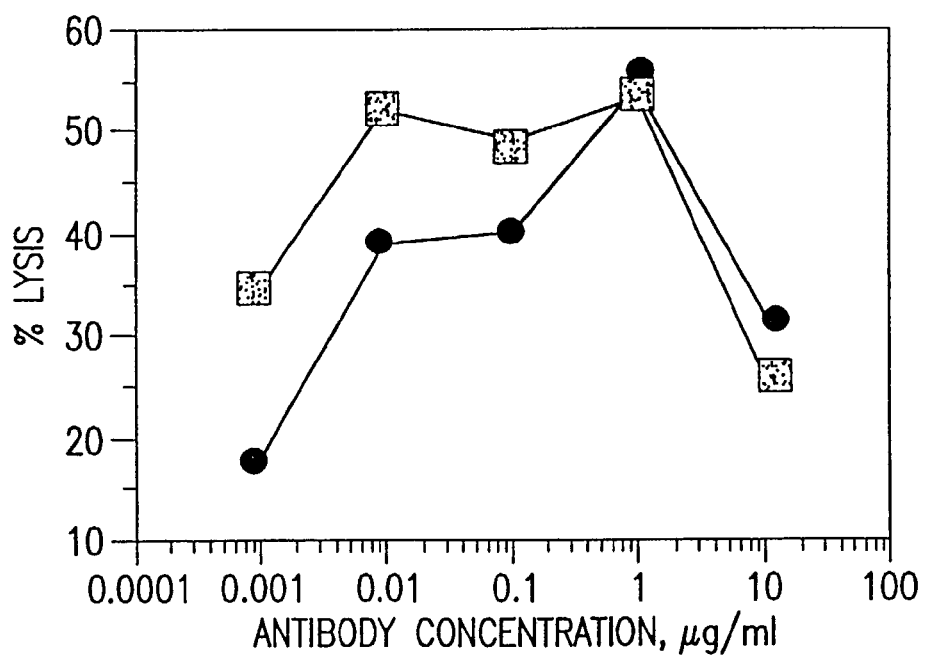
Figure 16A:
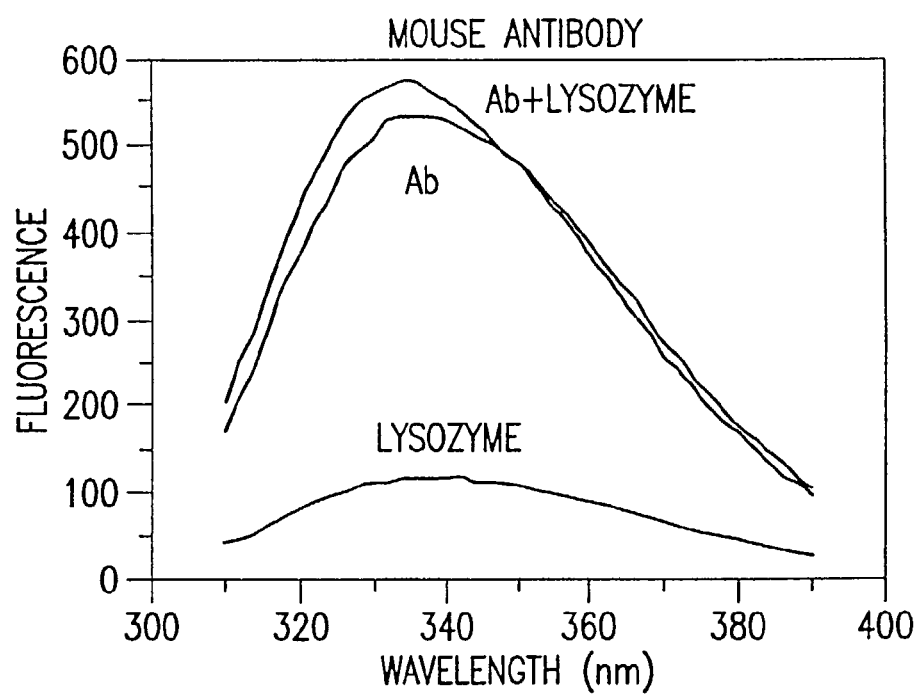
FIG. 16A to D are 4 graphs of fluorescence emission spectra of mouse and humanised anti-lysozyme antibody in the presence of two equivalents of lysozyme.
Figure 16B:
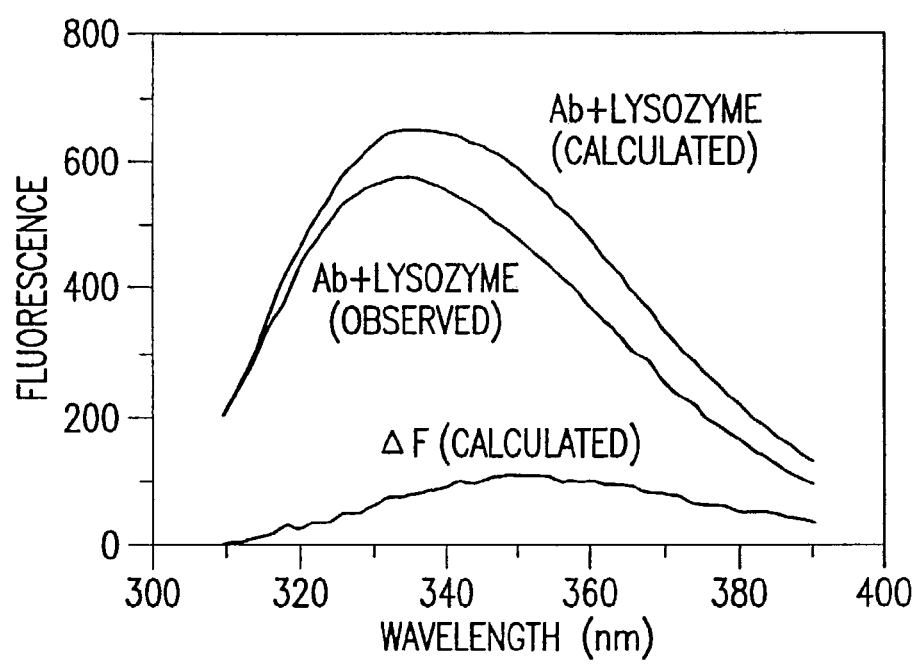
Figure 16C:
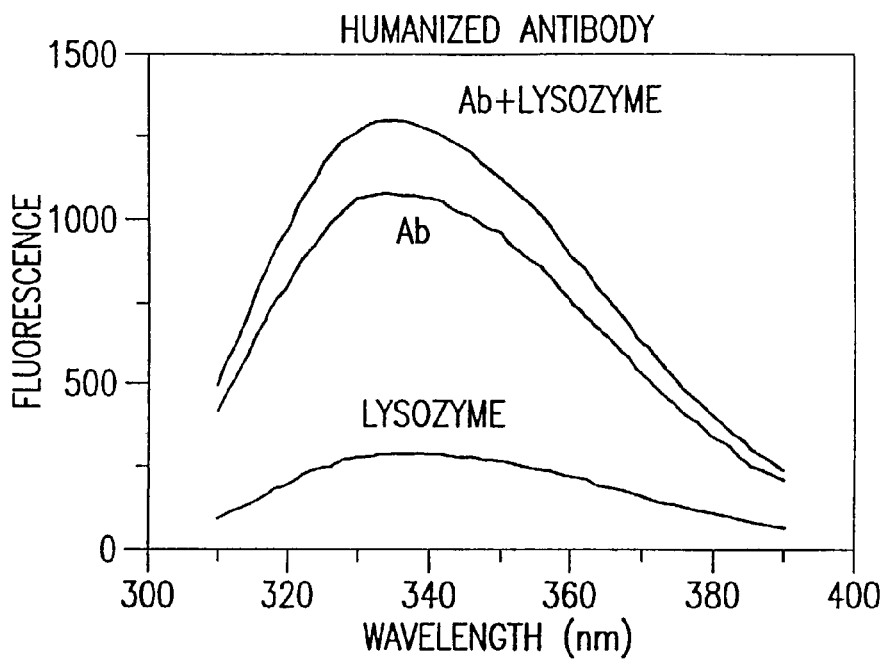
Figure 16D:
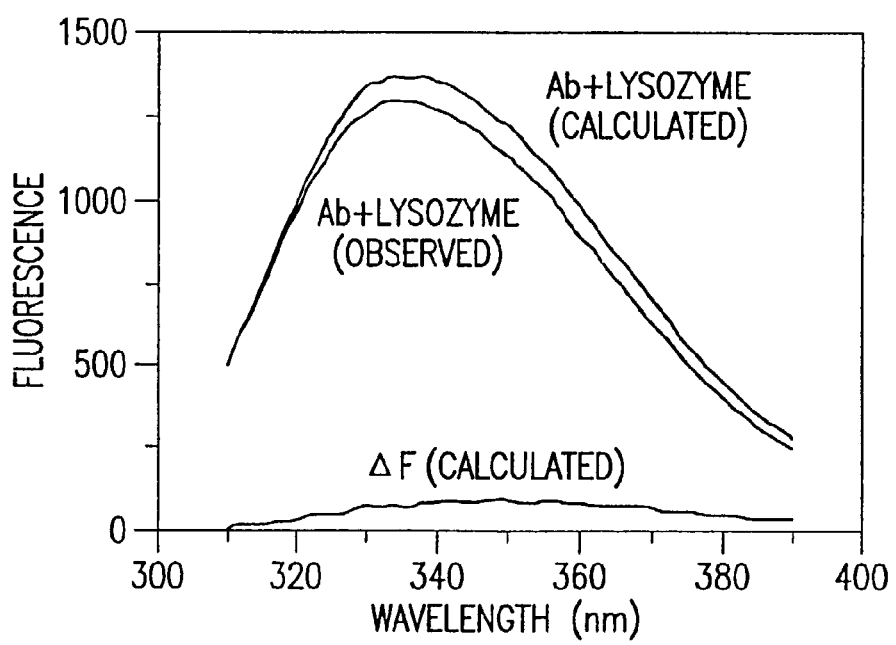

The purified antibody proved almost identical to the YTH34.5HL-G2b antibody in complement lysis (FIG. 15*a*). In cell mediated lysis the reshaped human antibody was more reactive than the rat antibody (FIG. 15*b*). Similar results to the ones in FIG. 15*b* were obtained with three different donors of target and effector cells (data not shown). Furthermore the antibody was as effective as YTH34.5HL-G2b in killing leukaemic cells from three patients with B Cell lymphocytic leukaemia by complement mediated lysis with human serum.

The rat antibody and fully humanised antibody were compared in a direct binding assay to Campath-1 antigen. Antibody concentrations were determined as described in FIGS. 14 and 15. The amount of rat antibody bound to partially purified Campath-1 antigen was determined as described in connection with Table 3. The amount of human antibody bound was determined by an ELISA assay using a biotinylated sheep anti-human IgG antibody (Amersham).

TABLE 4

Reshaping the heavy and light chain variable domains simultaneously

| antibody | Concentration of antibody in ug/ml at 50% binding antigen binding |
|---|---|
| RaVHCAMP Ra1GG2B | |
| RaVHCAMP RaKappa | 1.01 |
| HuVHCAMP (Ser 27 to Phe, Ser30 to Thr) Hu1GG1 | |
| HuVLCAMP HuKappa | 1.11 |

Thus by transplanting the hypervariable regions from a rodent to a human antibody of the IgG1 subtype, the antibody can be reshaped for therapeutic application.

The strategy illustrated in FIG. 12 is stepwise assembly to allow any problems to be detected at each stage (reshaping of heavy chain variable domain, selection of constant domain and reshaping of light chain variable domain). It is quite possible to build the reshaped antibody in a single step assembly, i.e. constructing the two reshaped variable domains, attaching to appropriate constant domains and cotransfecting into e.g. YO.

Example 4

Following the work described in Example 2, a fully "humanised" anti-lysozyme antibody with reshaped heavy and light chain variable domains was constructed.

The heavy chain variable region was constructed as described in Example 2 above, and the light chain variable region was constructed as described in Example 3 above.

Heavy and light chain constructs were prepared from 1 L of bacterial culture by CsCl density gradient ultracentrifugation. 20 ug of each plasmid was digested with Pvu1 and co-transfected into $10^7$ NSO cells by electroporation. Transformants were selected by growth in medium containing mycophenolic acid, in a 24-well tissue culture plate. After two weeks growth, aliquots of cells were removed from each well, incubated overnight with $^{35}$S-methionine, an the supernatant medium affinity adsorbed with Protein A-Sepharose beads (Pharmacia). Absorbed proteins were subjected to sodium dodecyl sulfate-polyacrylamide gel electrophoresis (SDS-PAGE), followed by autoflurography. Clones were isolated by limiting dilution from the wells which had yielded both heavy and light chain bands on the autofluorogram. The radioincorporation screening method was again employed to identify those clones secreting a complete antibody. Of these, one cell line was chosen and propagated for storage and further analysis.

A 2L culture of the cell line was grown to saturation in Dulbecco's modifed Eagle medium supplemented with 10% fetal calf serum. Antibody was concetrated from the culture medium by ammonium sulfate precipitation. The precipitate was redissolved in phosphate-buffered saline, pH 7.4(PBS), dialyzed, and chromatographed on a column of lysozyme-Sepharose (prepared by reaction of 20 mg lysozyme per ml of CNBr-activated Sepharose CL-4B). The column was washed with 0.5 M NaCl, 0.1 M Tris chloride, pH 8.5, and subsequently with 50 mM Et²NH. Immunoglobulin-containing fractions eluting with the latter wash were identified by SDS-PAGE followed by Coomassie Blue staining; these were pooled and dialyzed against PBS. The dialyzed material was applied to a column of protein A-Sepharose. The column was washed with PBS, followed by 0.1 M citrate buffers in the order pH 6, 5, 4, 3. A peak eluting at pH 4 (the pH expected for elution of a human immunoglobulin of the gamma 2 isotype) was identified as homogeneous immunoglobulin by SDS-PAGE. This was dialyzed vs PBS for storage. Its concentration was determined spectrophotometrically using an extinction coefficient at 280 nm of 1.4 $cm^{-1}$ $(mg/ml)^{-1}$.

The fluorescence emission spectra of mouse and "humanised" antilysozyme in the presence of two equivalents of lysozyme show a loss of intensity and a hypsochromic shift relative to the calculated sum of the spectra of free antibody and free lysozyme. This quenching effect is indicative of an interaction between lysozyme and each antibody. Sets of spectra are shown in FIGS. 16A-D. Solution conditions prevailing during the measurement of these spectra were 200 nM immunoglobulin and 400 nM lysozyme (separately or in combination), in PBS at a temperature of 20° C. Spectroscopic conditions employed consisted of an excitation wavelength of 280 nm with a 5 nm bandwidth, and an emission bandwidth of 2.5 nm. Data acquisition was with a Perkin-Elmer LS-5B spectrofluorimeter interfaced to a Macintosh microcomputer, which in turn was used for data manipulation and display.

Figure 17:
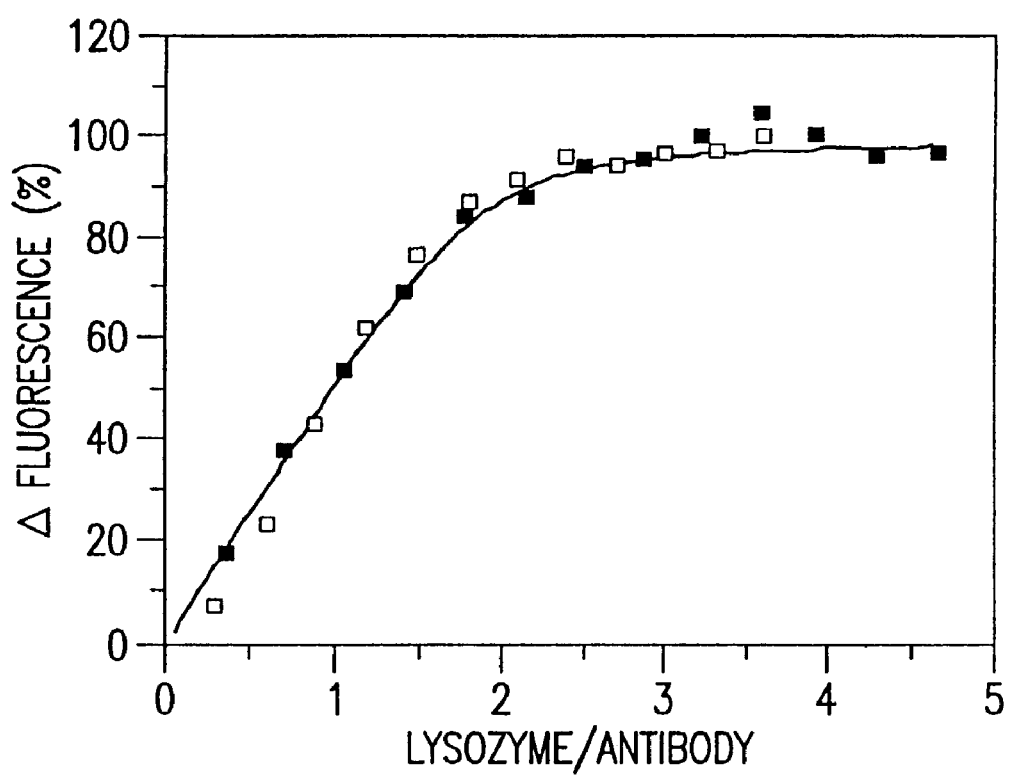
FIG. 17 is a graph illustrating spectral change at fixed wavelength as a function of lysozyme concentration on titration of antibody samples.

The spectral change at fixed wavelength was measured as a function of lysozyme concentration. Antibody samples were titrated in the spectroflurimeter with small aliquots of a concentrated lysozyme solution, in parallel with a control antibody, which did not interact with lysozyme, at an identical concentration. The fluorescence was determined after each addition. Titration data are shown in FIG. 17 (filled squares, humanized; open squares, mouse). The spectral change is expressed as a percent of the maximum change observed at saturation, and titrant amounts are put on a ratio scale to facilitate comparison of the two sets of data. Actual conditions for the measurements were for the humanized antibody: 200 nM, 10°, 290 nm excitation, 390 nm emission; for the mouse antibody: 50 nM, 25° 280 excitation, 340 emission. The titration showed an equivalence point of 1.9 binding sites per mole for the humanized antibody, and 1.8 for the mouse, extremely close to the 2 antigen binding sites expected for an immunoglobulin G. The data do not allow deduction on exact binding constant for the interaction of lysozyme and "humanized" antibody. However it appears to be in the range 5–50 nM.

Example 5

Reshaped Fv fragments of the anti-lysozyme antibody D1.3 (Verhoeyen et al, loc. cit) were constructed. The heavy chain variable region was reshaped by combining human framework (FR) sequences from the myeloma protein NEW (Saul F. A., Amzel, M., Poljak R. J., J. Biol. Chem. 253.585 (1978)) with the mouse D1.3 CDRs which provide the antigen specifically (Verhoeyen et al, loc. cit). The reshaped light chain contains human FRs from human kappa consensus sequence (Kabat et al, loc. cit) similar to the sequence of the Bence Jones protein REI (Epp, O., et al, Eur. J. Biochem. 45, 513 (1974)) combined with the D1.3 light chain CDRs.

Figure 18:
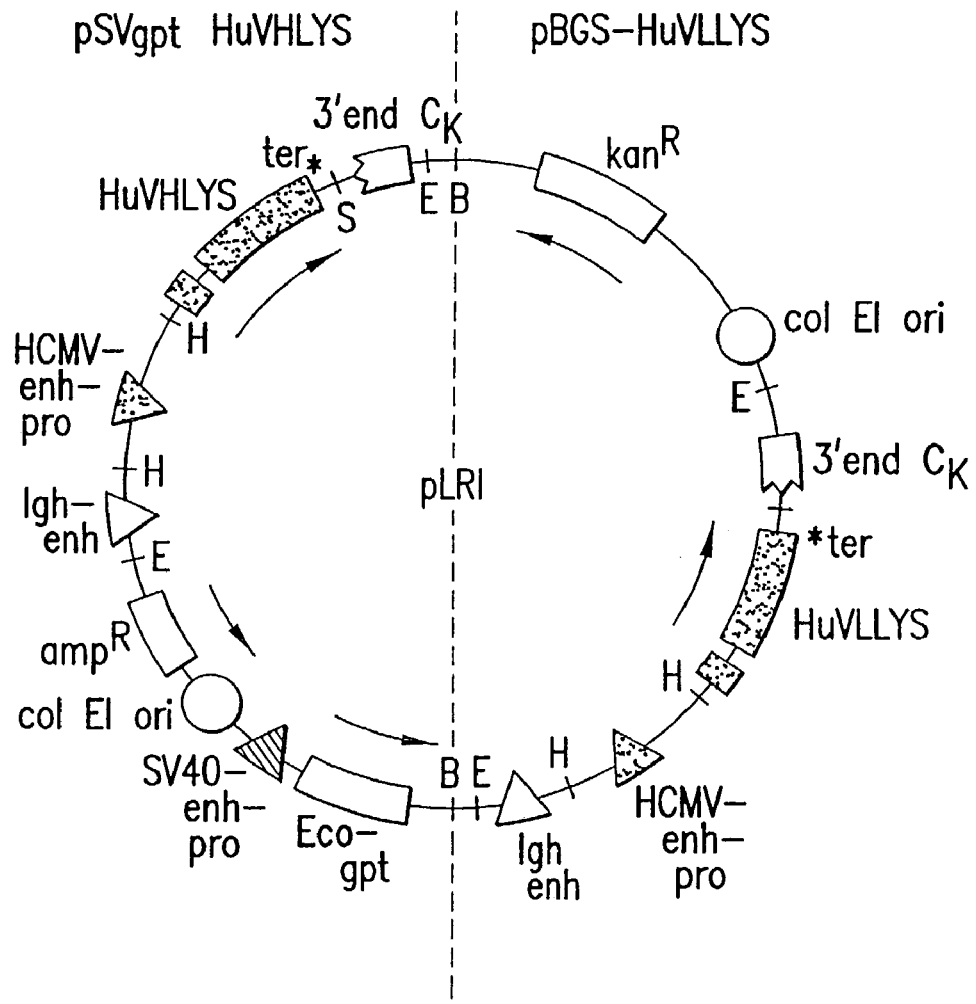
FIG. 18 illustrates the plasmid for expression of the Fv fragment of a reshaped anti-lysozyme antibody.

FIG. 18 illustrates the plasmid for the expression of the Fv-fragment of the reshaped version of the antilysozyme antibody D1.3. The plasmid was transfected by electroporation (Potter, H., Weir, L., Leder, P. Proc. Natl. Acad. Sci. USA 81, 7161 (1984)) into the non-producer myeloma cell line NSO (Galfre, G., Milstein, C., Meth. Enzymol 73, 1 (1981)). Transfectants were selected with mycophenolic acid (Mulligan, R. C., Berg, P., Proc. Natl. Acad. Sci. USA 78, 2072–2076).

The genes (HuVHLYS and HuVLLYS) for the VH and VL domains were produced as HindIII-BamHI fragments in M13 for the expression of the whole antibody (see M. Verhoeyen et al. Science loc. cit. for sequence of VH, see Riechmann, I., Clark, M., Waldmann, H., Winter, G., Nature in press for VL-framework sequences and see Verhoeyen, M., Berek, C., Winter, G., Nucleic Acid. Res. submitted for the VL CDRs). At the 3'end of their coding sequence two stops codons followed by a SacI-site were introduced by priming with oligonucleotides I and II on the corresponding single strands. Between the RNA start site and the translation start of the leader sequence in both genes a HindIII site was introduced using oligonucleotide III. The resulting HindIII-BamHI fragments were cloned into a pSVgpt vector (Riechmann et al, Nature loc cit). The vector contains a EcoR-HindIII fragment of an Ig-heavy chain enhancer (IgH enh) as a linker. The 3' SacI-BamHI fragment of both genes was then exchanged with a SacI-BamHI fragment of the human kappa constant region (3'end $C_k$) (Hieter, P. A. et al. Cell 22, 197 (1980)) to provide a polyadenylation signal. Into the HindIII site of both vectors a HindIII-HindIII fragment of the HCMV immediate-early gene (Stenberg, R. M. et al. J. Virol 49, 190(1984), Boshart, M. et al., Cell 41, 521 (1985)) containing its enhancer, promotor and the first non-translated exon (HCMV enh-pro) were cloned. The complete VL-gene (containing Ig-enhancer, HCMV-promoter, VL-coding region and polyadenylation signal) was then subcloned as an EcoRI-fragment into pBGS18 (Spratt, B., et al., Gene 41, 337 (1986)) and the resulting vector pBGS-HuVLLYS was cloned into the pSVgpt-HuVHLYS vector as a BamHI fragment as shown in FIG. 18.

The final plasmid pLRI further contained the resistance genes for the drugs ampicillin ($amp^R$), kanamycin ($kan^R$) and mycophenolic acid (Eco gpt) two col EI origins of replication (col EI on) and the SV40 enhancer (SV40 enh pro). The BamHI (B), HindIII (H), EcoRI (E) and SacI (S) restriction sites used for cloning steps are indicated. The diagram is not to scale. Oligonucleotides I=5'-GAG AGG TTG GAG CTC TTA TTA TGA GGA GAC-3' (SEQ ID NO. 20), II=5'-AAG TTT AAA GAG CTC TAG TAT TTG ATT TC-3' (SEQ ID NO. 21), III=5'-CTC AGT AAG CTT AGA GAG A-3' (SEQ ID NO. 22).

Both heavy and light chain variable domains were combined in a single plasmid to facilitate the selection of transfectants using the gpt selection system (Mulligan, R. C., Berg. P., Proc. Natl. Acad. Sci. USA 78, 2072, 2076). Pools of transfected cell clones were analysed on SDS-acrylamide gels after $^{35}S$ methionine incorporation and affinity purification of culture supernatants with lysozyme Sepharose. The cloned cell line used for the preparation of Fv-fragments secreted about 8 mg/L when grown in roller bottles. Thus it is possible to produce Fv fragments in myeloma cells with yields similar to recombinant versions of intact antibodies (Neuberger, M. S., Wiliams, G. T., Fox, R. O., Nature 312, 604 (1984), Riechmann, I. et al, Nature, loc. cit).

Figure 19:
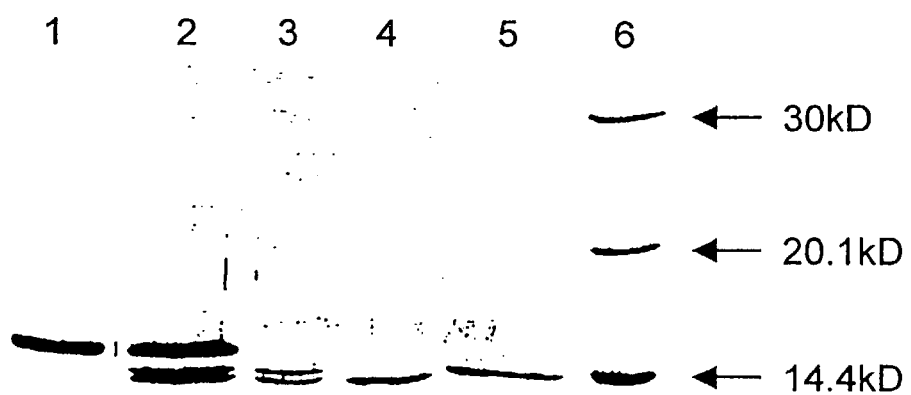
FIG. 19 illustrates the results of SDS acrylamide (16%) gel analysis of the Fv fragments and other units.
Figure 20:
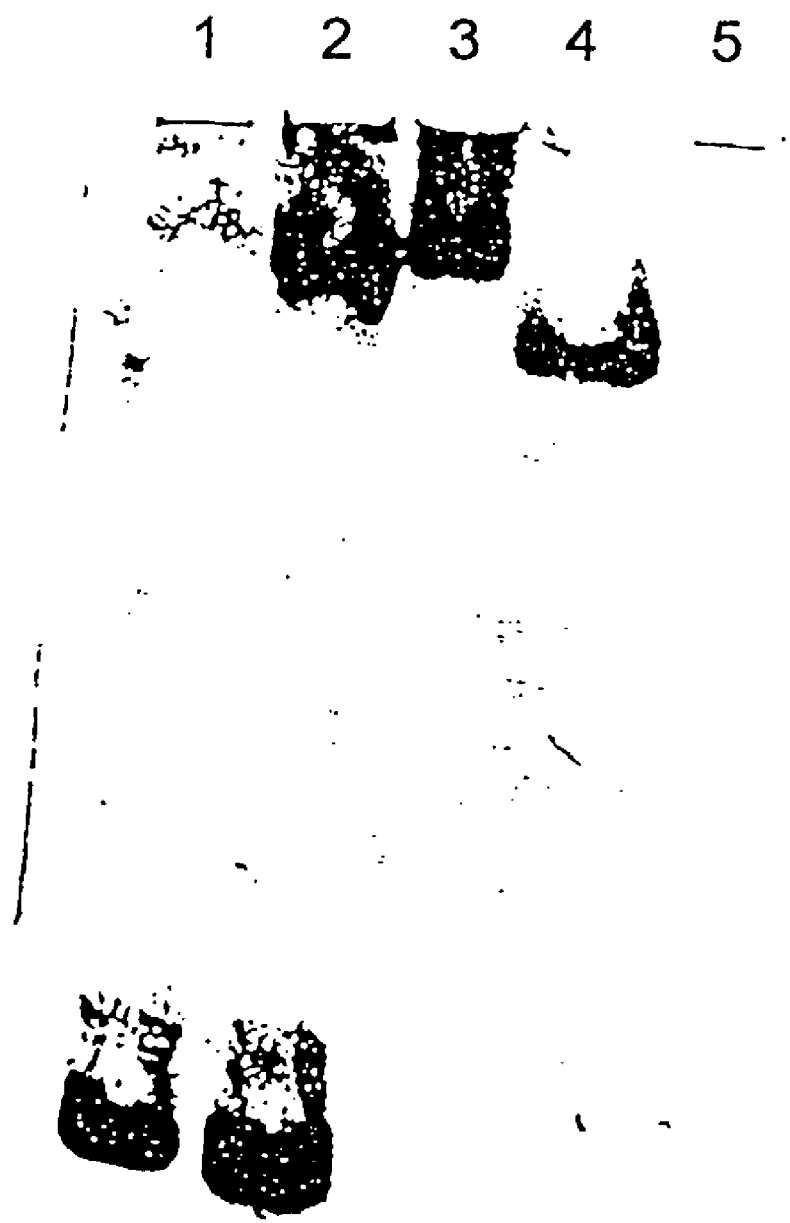
FIG. 20 illustrates the results of native acrylamide (8%) gel analysis at pH 7.5 of the Fv fragments and other units.

The Fv fragment contains two chains of about 12 KD (calculated values 12, 749 for VH and 11, 875 for VL) when analysed on SDS gels. See results in FIG. 19, in which lysozyme was run in lane 1, Fv-fragment plus lysozyme in lane 2, affinity purified Fv-fragment in lane 3, isolated VL-domain in lane 4, isolated VH-domain in lane 5) and size markers in lanes 6). The Fv-fragment and the lysozyme/Fv-fragment complex were eluted from the bands in the native gel in FIG. 20 (lanes 2, 3). All samples were applied in buffer containing beta mercaptoethanol. The Fv-fragment is secreted in a functional form, as it can readily be purified from the culture supernatant with lysozyme Sepharose (Fv-fragments from cell culture supernatants were prepared by filtering through two layers of Whatmann 3MM paper, adsorption to lysozyme coupled to CnBr-Sepharose (Pharmacia), extensive washing with phosphate buffered saline and elution with 50 mM diethylamine. Eluates were immediately adjusted to pH 7.5)

When the purified Fv-fragment was investigated on an HPLC sizing column (Biozorbax GF250) in phosphate buffered saline, only a single peak was observed and its retention time did not change between concentrations of 70 and 0.3 mg/L.

The Fv-fragment was also analysed on native acrylamide (8%) gels. See results in FIG. 20, in which lysozyme was run in lane 1, lysozyme/Fv fragment complex plus free lysozyme in lane 2, affinity purified Fv-fragment in lane 3, isolated VL-domain in lane 4 and isolated VH-domain in lane 5. Gel and running buffer contained 40 mM Tris, 8.3 mM sodium acetate, 0.4 mM $Na_2EDTA$ and was adjusted to pH 7.6 with acetic acid. No stacking gel was used, the gel was run with reversed polarity. Here the Fv-fragment runs as a single band, that contains both the VH and the VL domain when analysed on SDS gels (compare lane 3 in FIGS. 19 and 20). This band can be shifted on the native gel, when the antigen lysozyme is added. The shifted band contains lysozyme, VH and VL domain in similar amounts when analysed on SDS-gels (compare lane 2 in FIGS. 19 and 20). Further, the isolated VL domain runs as a diffused band with a mobility different to the Fv-fragment on the native gel (lane 4, FIG. 20). The isolated VH does not run into the gel because of its net charge at pH 7.5.

(The VL and VH-domains were separated on a Mono-S column (Pharmacia) in 50 mM acetic acid, 6 M urea (adjusted to pH 4.8 with NaOH) using 0 to 0.3 M NaCl gradient over 6 minutes. The VH was sufficiently pure according to SDS gel analysis. The VL was further purified after desalting into phosphate buffered saline on a Biozorbax GF250 (DuPont) sizing column to get rid of residual VH-VL heterodimer) These results strongly suggest that the predominant form of the Fv-fragment at pH 7.5 is an associated VH-VL heterodimer. Also its apparent molecular weight in ultracentrifuge sedimentation analysis was about 23.5 kD.

The same was observed with Fv-fragments obtained by proteolytic digestion (Inbar, D., Hochmann, J., Givol, D., Proc. Natl. Acad. Sci USA 69, 2659 (1972), Kakimoto, K., Onoue, K., J.Immunol 112, 1373 (1974), Sharon, J., Givol, D., Biochemistry 15, 1591 (1976)).

The formation of VH-VL heterodimers was further established, when Fv fragments were incubated at a concentration of 0.5 mg/ml in phosphate buffered saline with 3.7% formaldehyde overnight. Crosslinked VH-VL heterodimers of about 25 kD were formed (Purified, biosynthetically $^{35}S$-methionine labelled VH domain was incubated in 3.7% formaldehyde/PBS overnight in the absence or presence of excessive unlabelled VH-VL heterodimer. When analysed on SDS gels crosslinked, labelled VH VL heterodimers (molecular weight of about 25 kD) are formed from isolated labelled VH only in the prescence of unlabelled Fv-fragment. No formation of dimers could be detected in the absence of unlabelled Fv-fragment). Lysozyme-Sepharose purification of the crosslinked material showed that the crosslinked VH-VL heterodimer is still active. Overloading of SDS gels with crosslinked material also made visible a small fraction (less than 5%) of slightly lower molecular weight material suggesting the formation of crosslinked VL homodimers. No higher molecular weight band for possible VH homodimers was observed.

Figure 21:
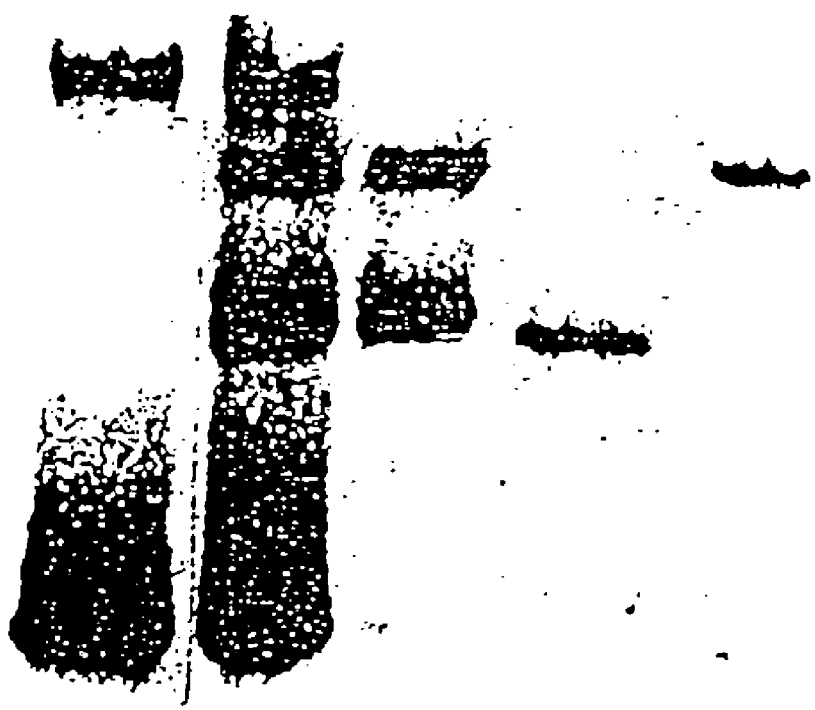
FIG. 21 illustrates the results of native acrylamide (8%) gel analysis at pH4 of the Fv fragments and other units.

Nevertheless dissociation was observed when the Fv-fragment was analysed on native acrylamide gels at pH4.5. Under these conditions the VH and the VL formed each a single band see results in FIG. 21, in which lysozyme was run in lane 1, lysozyme plus Fv-fragment in lane 2, affinity purified Fv-fragment in lane 3, isolated VL-domain in lane 4 and isolated VH-domain in lane 5. Incubation of antibodies at low pH has been used historically to facilitate their proteolytic digestion (Connell, G. E., Porter, R. R, Biochem. J. 124, 53P (1971)) probably reflecting the same underlying structural change.

Although the Fv-fragment is predominantly associated at neutral pH, it is in a dynamic equilibrimun; the purified biosynthetically labelled VH domain exchanges with the unlabelled VH domain when incubated with an excess of unlabelled VH-VL heterodimer, because labelled VH-VL heterodimers can be trapped by crosslinking with formaldehyde.

However, the dissociation of Fv-fragments should not cause problems in diagnostic or therapeutic applications. For structural studies, for which high protein concentrations are used Fv-fragments will certainly be of considerable advantage without further treatment. They should especially simplify the assignment of signals in NMR-spectra, if the same beta-sheet frameworks are used for Fv-fragments with different specificities.

It will of course be understood that the present invention has been described above purely by way of example, and modifications of detail can be made within the scope of the invention as defined in the appended claims.

What is claimed is:

1. An antibody comprising a human kappa light chain variable domain, wherein said light chain variable domain comprises a set of tour human Kabat framework regions (FRs), wherein each of said FRs in said set of four FRs comprises residues identical to the most common residue in each position in a Kabat alignment of a human kappa sub-group 1, and wherein said antibody binds an antigen.

2. An antibody comprising a human kappa light chain variable domain, said light chain variable domain comprising a set of four human Kabat framework regions (FRs), wherein said antibody incorporates FRs comprising residues identical to the most common residue in each position in a Kabat alignment of a human kappa sub-group 1, and wherein said antibody has three Kabat complementarity determining regions (CDRs) comprising sequences of amino acid residues, wherein said sequences are not human, and wherein said antibody binds the same antigen as a non-human antibody having a kappa light chain comprising said sequences.

3. An antibody comprising a human kappa light chain variable domain, said light chain variable domain comprising a set of four human Kabat framework regions (FRs), wherein said antibody incorporates FRs comprising residues identical to the most common residue in each position in a Kabat alignment of a human kappa sub-group 1, wherein said antibody has three Kabat complementarity determining regions (CDRs) comprising amino acid residues from a non-human antibody, and wherein said antibody binds the same antigen as the non-human antibody.

4. The antibody of claim 2 or 3, wherein said antibody incorporates a human framework region (FR1) comprising amino acids 20–42 of SEQ. ID NO:37.

5. The antibody of claim 2 or 3, wherein said antibody incorporates a human framework region (FR2) comprising amino acids 54–68 of SEQ. ID NO:37.

6. The antibody of claim 2 or 3, wherein said antibody incorporates a human framework region (FR4) comprising amino acids 117–127 of SEQ. ID NO:37.

7. The antibody of claim 2 or 3, wherein said non-human antibody is a rodent antibody.

8. The antibody of claim 7, wherein said rodent antibody is a mouse antibody.

9. The antibody of claim 2 or 3, wherein each of said FRs in said set of four FRs comprises residues identical to the most common residue in each position in the Kabat alignment of the human kappa sub-group 1.

10. The antibody of claim 2 or 3, wherein three said set of four human Kabat FRs comprise residues identical to the most common residue in each position in the Kabat alignment of the human kappa sub-group 1, and wherein one of said set of four FRs contains at least one replacement amino acid residues.

11. The antibody of claim 2 or 3, wherein three of said set of four human Kabat FRs comprise residues identical to the most common residue in each position in the Kabat alignment of the human kappa sub-group 1, and wherein one of said set of four FRs contains at least two replacement amino acid residues.

12. The antibody of claim 2 or 3, wherein said antibody further comprises a heavy chain variable domain, said heavy chain variable domain comprising a set of four heavy chain human Kabat framework regions (FRs) and three heavy chain Kabat CDRs comprising amino acid residues from a donor antibody.

13. The antibody of claim 12, wherein said set of four heavy chain human Kabat FRs comprises an alteration in an acceptor FR of at least one replacement of a first amino acid residue with a second amino acid residue from a corresponding position in a donor FR of the donor antibody, and wherein a 200% van der Waals surface thrown around said second amino acid residue identifies a packing interaction with one or more amino acid residues in a CDR in the donor antibody.

14. The antibody of claim 13, wherein the packing interaction enhances the antigen-binding activity of the antibody compared to a second antibody, wherein the second antibody lacks the alteration in the acceptor FR, but is otherwise identical to the antibody comprising said alteration.

15. The antibody according to claim 12, wherein said antibody is an IgG isotype.

16. The antibody according to claim 12, wherein said antibody is selected from the group consisting of an IgG1, IgG2 and IgG4 isotype.

17. The antibody according to claim 12, wherein said antibody is an IgG1 antibody, and wherein said IgG1 antibody is lytic.

18. The antibody according to claim 12, wherein said antibody is a therapeutic antibody.

19. The antibody according to claim 12, wherein said antibody has effector functions.

20. The antibody according to claim 19, wherein said effector function is complement activation.

21. The antibody according to claim 19, wherein said effector function is antibody-dependent cell-mediated cytotoxicity (ADCC).

22. An antibody comprising a human kappa light chain variable domain having a set of four framework regions (FRs) of a human antibody and three complementarity determining regions (CDRs) comprising residues from a non-human antibody, wherein said antibody binds the same antigen as the non-human antibody.

23. The antibody of claim 22, wherein said non-human antibody is a mouse antibody.

24. The antibody of claim 22, wherein said non-human antibody is a rodent antibody.

* * * * *

UNITED STATES PATENT AND TRADEMARK OFFICE
CERTIFICATE OF CORRECTION

PATENT NO.       : 6,982,321 B2
APPLICATION NO.  : 10/351748
DATED            : January 3, 2006
INVENTOR(S)      : Winter It is certified that error appears in the above-identified patent and that said Letters Patent is hereby corrected as shown below:

In the drawings, Sheet 15, Fig. 10, the phrase "Sequence of the synthetic gene HUVLLYSO" should read --Sequence of the synthetic gene HUVLLYS°--.
Column 1, line 5, "07/942,340" should read --07/942,140--.
Column 3, line 62, "to bid antigen" should read --to bind antigen--.
Column 6, line 38, "the signle strand" should read --the single strand--.
Column 7, line 11, "totally grated into" should read --totally grafted into--.
Column 8, line 25, "B1-0.8" should read --B1-8--.
Column 8, line 41, "MOVNP" should read --MoVNP--.
Column 10, line 5, "HuvNP-IgE" should read --HuVNP-IgE--.
Column 12, line 17, "HuNP" should read --HuVNP--.
Column 12, line 28, "1ug" should read --1 ug--.
Column 12, line 31, "E. Coli" should read --E. coli--.
Column 12, line 38, "hybrdidised" should read --hybridised--.
Column 14, line 52, "Friend, P.'& Calne, R. Transportation" should read --Friend, P. & Calne, R. Transplantation--.
Column 15, line 7, "Bruccoleri, R. '&" should read --Bruccoleri, R. & --.
Column 15, line 17, "Amzel, M. '& Poljak, R. J. J." should read --Amzel, M. & Poljak, R. J. J.--.
Column 15, line 21, "Schiffer, M. '& Huber, R." should read --Schiffer, M. & Huber, R.--.
Column 15, line 27, "J., Neuberger, M. S. '& Winter," should read --J., Neuberger, M. S. & Winter,--.
Column 15, line 35, "Maizel., J. V. Jr' & Leder, P." should read --Maizel., J. V. Jr. & Leder, P.--.
Column 15, line 43, "O. '& Milstein, C." should read -- O. & Milstein, C.--.
Column 15, line 48, "Gubler, U. '&" should read --Gubler, U. &--.
Column 15, line 49, "Nicklen, S.A. '&" should read --Nicklen, S.A. &--.
Column 15, line 50, "Proc. Natl. Acad." should read -- Proc. Natl. Acad.--.
Column 16, line 33, "Maizel., J '& Leder, P." should read -- Maizel., J. & Leder, P--.
Column 18, line 45, "Mulligan, R. C. '& Berg, P. Proc.natl.Acad." should read -- Mulligan, R. C. & Berg, P. Proc.Natl.Acad. --.
Column 18, line 47, "Southern, P.J. '& Berg. P.J." should read as -- Southern, P.J. & Berg, P.J.--.
Column 18, line 61, "Proc. natl. Acad." should read --Proc. Natl. Acad.--.
Column 18, line 65, "Proc. natl. Acad." should read --Proc. Natl. Acad.--.

UNITED STATES PATENT AND TRADEMARK OFFICE
CERTIFICATE OF CORRECTION

PATENT NO. : 6,982,321 B2
APPLICATION NO. : 10/351748
DATED : January 3, 2006
INVENTOR(S) : Winter It is certified that error appears in the above-identified patent and that said Letters Patent is hereby corrected as shown below:

Column 21, line 41, "Proc. natl. Acad." should read --Proc. Natl. Acad.--.
Column 22, line 57, "an the" should read --and the--.
Column 23, line 3, "concetrated" should read --concentrated--.
Column 23, line 10, "Et2NH" should read --Et2NH--.
Column 24, line 23, "3'end" should read --3' end--.
Column 24, line 50, "(col El on)" should read -- (col El ori)--.
Column 26, line 27, "pH4.5" should read --pH 4.5--.
Column 26, line 38, "equilibrimun" should be --equilibrium--.
Col. 55, line 39, "a set of tour" should read --a set of four--.
Col. 56, line 55, "wherein three said set" should read --wherein three of said set--.
Col. 56, line 60, "acid residues" should read --acid residue--.

Signed and Sealed this

Eighth Day of August, 2006

JON W. DUDAS
*Director of the United States Patent and Trademark Office*

SEQUENCE LISTING

<160> NUMBER OF SEQ ID NOS: 59

<210> SEQ ID NO 1
<211> LENGTH: 48
<212> TYPE: DNA

<213> ORGANISM: Artificial Sequence
<220> FEATURE:
<223> OTHER INFORMATION: Oligonucleotide used for gene synthesis and
      mutagenesis-PK1

<400> SEQUENCE: 1
gacatccaga tgacccagag cccaagcagc ctgagcgcca gcgtgggt        48

<210> SEQ ID NO 2
<211> LENGTH: 60
<212> TYPE: DNA
<213> ORGANISM: Artificial Sequence
<220> FEATURE:
<223> OTHER INFORMATION: Oligonucleotide used for gene synthesis and
      mutagenesis-PK2

<400> SEQUENCE: 2
gacagagtga ccatcacctg tagagccagc ggtaacatcc acaactacct ggcttggtac        60

<210> SEQ ID NO 3
<211> LENGTH: 44
<212> TYPE: DNA
<213> ORGANISM: Artificial Sequence
<220> FEATURE:
<223> OTHER INFORMATION: Oligonucleotide used for gene synthesis and
      mutagenesis-PK3

<400> SEQUENCE: 3
caagccaggt agttgtggat gttaccgctg gctctacagg tgat        44

<210> SEQ ID NO 4
<211> LENGTH: 33
<212> TYPE: DNA
<213> ORGANISM: Artificial Sequence
<220> FEATURE:
<223> OTHER INFORMATION: Oligonucleotide used for gene synthesis and
      mutagenesis-PK4

<400> SEQUENCE: 4
ggtcactctg tcacccacgc tggcgctcag gct        33

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide used for gene synthesis and
      mutagenesis-PK5

<400> SEQUENCE: 5
gcttgggctc tgggtcatct ggatgtctgc a        31

<210> SEQ ID NO 6
<211> LENGTH: 49
<212> TYPE: DNA
<213> ORGANISM: Artificial Sequence
<220> FEATURE:
<223> OTHER INFORMATION: Oligonucleotide used for gene synthesis and
      mutagenesis-KK1

<400> SEQUENCE: 6
cagcagaagc caggtaaggc tccaaagctg ctgatctact acaccacca        49

<210> SEQ ID NO 7
<211> LENGTH: 49
<212> TYPE: DNA
<213> ORGANISM: Artificial Sequence

```
<220> FEATURE:
<223> OTHER INFORMATION: Oligonucleotide used for gene synthesis and
      mutagenesis-KK2

<400> SEQUENCE: 7
ccctggctga cggtgtgcca agcagattca gcggtagcgg tagcggtac                      49

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide used for gene synthesis and
      mutagenesis-KK3

<400> SEQUENCE: 8
cgctaccgct accgctgaat ctgct                                                25

<210> SEQ ID NO 9
<211> LENGTH: 40
<212> TYPE: DNA
<213> ORGANISM: Artificial Sequence
<220> FEATURE:
<223> OTHER INFORMATION: Oligonucleotide used for gene synthesis and
      mutagenesis-KK4

<400> SEQUENCE: 9
tggcacaccg tcagccaggg tggtggtgta gtagatcagc                                40

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide used for gene synthesis and
      mutagenesis-KK5

<400> SEQUENCE: 10
agctttggag ccttacctgg cttctgctgg tac                                       33

<210> SEQ ID NO 11
<211> LENGTH: 59
<212> TYPE: DNA
<213> ORGANISM: Artificial Sequence
<220> FEATURE:
<223> OTHER INFORMATION: Oligonucleotide used for gene synthesis and
      mutagenesis-KE1

<400> SEQUENCE: 11
cgacttcacc ttcaccatca gcagcctcca gccagaggac atcgccacct actactgcc           59

<210> SEQ ID NO 12
<211> LENGTH: 49
<212> TYPE: DNA
<213> ORGANISM: Artificial Sequence
<220> FEATURE:
<223> OTHER INFORMATION: Oligonucleotide used for gene synthesis and
      mutagenesis-KE2

<400> SEQUENCE: 12
agcacttctg gagcacccca aggacgttcg gccaagggac caaggtgga                      49

<210> SEQ ID NO 13
<211> LENGTH: 49
<212> TYPE: DNA
<213> ORGANISM: Artificial Sequence
<220> FEATURE:
```

<223> OTHER INFORMATION: Oligonucleotide used for gene synthesis and
       mutagenesis-KE3

<400> SEQUENCE: 13
aatcaaacgt gagtagaatt taaactttgc ttcctcagtt ggatcctag          49

<210> SEQ ID NO 14
<211> LENGTH: 35
<212> TYPE: DNA
<213> ORGANISM: Artificial Sequence
<220> FEATURE:
<223> OTHER INFORMATION: Oligonucleotide used for gene synthesis and
       mutagenesis-KE4

<400> SEQUENCE: 14
aattctagga tccaactgag gaagcaaagt ttaaa                        35

<210> SEQ ID NO 15
<211> LENGTH: 34
<212> TYPE: DNA
<213> ORGANISM: Artificial Sequence
<220> FEATURE:
<223> OTHER INFORMATION: Oligonucleotide used for gene synthesis and
       mutagenesis-KE5

<400> SEQUENCE: 15
ttctactcac gtttgatttc caccttggtc cctt                         34

<210> SEQ ID NO 16
<211> LENGTH: 44
<212> TYPE: DNA
<213> ORGANISM: Artificial Sequence
<220> FEATURE:
<223> OTHER INFORMATION: Oligonucleotide used for gene synthesis and
       mutagenesis-KE6

<400> SEQUENCE: 16
ggccgaacgt ccttggggtg ctccagaagt gctggcagta gtag              44

<210> SEQ ID NO 17
<211> LENGTH: 26
<212> TYPE: DNA
<213> ORGANISM: Artificial Sequence
<220> FEATURE:
<223> OTHER INFORMATION: Oligonucleotide used for gene synthesis and
       mutagenesis-KE7

<400> SEQUENCE: 17
gtggcgatgt cctctggctg gaggct                                  26

<210> SEQ ID NO 18
<211> LENGTH: 26
<212> TYPE: DNA
<213> ORGANISM: Artificial Sequence
<220> FEATURE:
<223> OTHER INFORMATION: Oligonucleotide used for gene synthesis and
       mutagenesis-KE8

<400> SEQUENCE: 18
gctgatggtg aaggtgaagt cggtac                                  26

<210> SEQ ID NO 19
<211> LENGTH: 26
<212> TYPE: DNA
<213> ORGANISM: Artificial Sequence
<220> FEATURE:
<223> OTHER INFORMATION: Oligonucleotide used for gene synthesis and -continued mutagenesis-PK0

<400> SEQUENCE: 19
tcatctggat gtcggagtgg acacct                     26

<210> SEQ ID NO 20
<211> LENGTH: 30
<212> TYPE: DNA
<213> ORGANISM: Artificial Sequence
<220> FEATURE:
<223> OTHER INFORMATION: Oligonucleotide I for construction of Fv
      fragment of a reshaped anti-lysozyme antibody in plasmid pLRI

<400> SEQUENCE: 20
gagaggttgg agctcttatt atgaggagac                 30

<210> SEQ ID NO 21
<211> LENGTH: 29
<212> TYPE: DNA
<213> ORGANISM: Artificial Sequence
<220> FEATURE:
<223> OTHER INFORMATION: Oligonucleotide II for construction of Fv
      fragment of a reshaped anti-lysozyme antibody in plasmid pLRI

<400> SEQUENCE: 21
aagtttaaag agctctacta tttgatttc                  29

<210> SEQ ID NO 22
<211> LENGTH: 19
<212> TYPE: DNA
<213> ORGANISM: Artificial Sequence
<220> FEATURE:
<223> OTHER INFORMATION: Oligonucleotide III for construction of Fv
      fragment of a reshaped anti-lysozyme antibody in plasmid pLRI

<400> SEQUENCE: 22
ctcagtaagc ttagagaga                             19

<210> SEQ ID NO 23
<211> LENGTH: 117
<212> TYPE: PRT
<213> ORGANISM: Homo Sapiens
<220> FEATURE:
<221> NAME/KEY: VARIANT
<222> LOCATION: 1
<223> OTHER INFORMATION: Xaa = Any Amino Acid
<220> FEATURE:
<223> OTHER INFORMATION: Amino acid sequence of VH domain of NEWM
      (Fig 2)

<400> SEQUENCE: 23

Xaa Val Gln Leu Gln Glu Ser Gly Pro Gly Leu Val Arg Pro Ser Gln
 1               5                  10                  15

Thr Leu Ser Leu Thr Cys Thr Val Ser Gly Ser Thr Phe Ser Asn Asp
             20                  25                  30

Tyr Tyr Thr Trp Val Arg Gln Pro Pro Gly Arg Gly Leu Glu Trp Ile
         35                  40                  45

Gly Tyr Val Phe Tyr His Gly Thr Ser Asp Asp Thr Pro Leu Arg
     50                  55                  60

Ser Arg Val Thr Met Leu Val Asp Thr Ser Lys Asn Gln Phe Ser Leu
65                   70                  75                  80

Arg Leu Ser Ser Val Thr Ala Ala Asp Thr Ala Val Tyr Tyr Cys Ala
                 85                  90                  95

Arg Asn Leu Ile Ala Gly Cys Ile Asp Val Trp Gly Gln Gly Ser Leu

```
                   100               105             110
Val Thr Val Ser Ser
            115

<210> SEQ ID NO 24
<211> LENGTH: 120
<212> TYPE: PRT
<213> ORGANISM: mouse
<220> FEATURE:
<223> OTHER INFORMATION: Amino acid sequence of VH domain of BI-8
      antibody (Fig 2)

<400> SEQUENCE: 24

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Arg Gly Leu Glu Trp Ile
         35                  40                  45

Gly Arg Ile Asp Pro Asn Ser Gly Gly Thr Lys Tyr Asn Glu Lys Phe
     50                  55                  60

Lys Ser Lys Ala Thr Leu Thr Val Asp Lys Pro Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Asp Tyr Tyr Gly Ser Ser Tyr Phe Asp Tyr Trp Gly Gln
            100                 105                 110

Gly Thr Thr Leu Thr Val Ser Ser
        115                 120

<210> SEQ ID NO 25
<211> LENGTH: 611
<212> TYPE: DNA
<213> ORGANISM: Homo Sapiens
<220> FEATURE:
<223> OTHER INFORMATION: Nucleotide sequence of HUVNP gene (Fig 3)

<400> SEQUENCE: 25
atgcaaatcc tctgaatcta catggtaaat ataggtttgt ctataccaca aacagaaaaa      60
catgagatca cagttctctc tacagttact gagcacacag gacctcacca tgggatggag     120
ctgtatcatc ctcttcttgg tagcaacagc tacaggtaag gggctcacag tagcaggctt     180
gaggtctgga catatatatg ggtgacaatg acatccactt tgcctttctc tccacaggtg     240
tccactccca ggtccaactg caggagagcg gtccaggtct tgtgagacct agccagaccc     300
tgagcctgac ctgcaccgtg tctggcagca ccttcagcag ctactggatg cactgggtga     360
gacagccacc tggacgaggt cttgagtgga ttggaaggat tgatcctaat agtggtggta     420
ctaagtacaa tgagaagttc aagagcagag tgacaatgct ggtagacacc agcaagaacc     480
agttcagcct gagactcagc agcgtgacag ccgccgacac cgcggtctat tattgtgcaa     540
gatacgatta ctacggtagt agctactttg actactgggg tcaaggcagc ctcgtcacag     600
tctcctcagg t                                                          611

<210> SEQ ID NO 26
<211> LENGTH: 140
<212> TYPE: PRT
<213> ORGANISM: Homo Sapiens
<220> FEATURE:
<223> OTHER INFORMATION: Amino acid sequence of HUVNP gene (Fig 3)
```

```
<400> SEQUENCE: 26

Met Gly Trp Ser Cys Ile Ile Leu Phe Leu Val Ala Thr Ala Thr Ile
 1               5                  10                  15

Gly Val His Ser Gln Val Gln Leu Gln Glu Ser Gly Pro Gly Leu Val
             20                  25                  30

Arg Pro Ser Gln Thr Leu Ser Leu Thr Cys Thr Val Ser Gly Ser Thr
         35                  40                  45

Phe Ser Ser Tyr Trp Met His Trp Val Arg Gln Pro Pro Gly Arg Gly
     50                  55                  60

Leu Glu Trp Ile Gly Arg Ile Asp Pro Asn Ser Gly Gly Thr Lys Tyr
 65                  70                  75                  80

Asn Glu Lys Phe Lys Ser Arg Val Thr Met Leu Val Asp Thr Ser Lys
                 85                  90                  95

Asn Gln Phe Ser Leu Arg Leu Ser Ser Val Thr Ala Ala Asp Thr Ala
            100                 105                 110

Val Tyr Tyr Cys Ala Arg Tyr Asp Tyr Tyr Gly Ser Ser Tyr Phe Asp
        115                 120                 125

Tyr Trp Gly Gln Gly Ser Leu Val Thr Val Ser Ser
130                 135                 140

<210> SEQ ID NO 27
<211> LENGTH: 39
<212> TYPE: DNA
<213> ORGANISM: Artificial Sequence
<220> FEATURE:
<223> OTHER INFORMATION: D1.3 CDR 1 oligonucleotide for cloning of HUVNP
      gene (Fig 5)

<400> SEQUENCE: 27
ctgtctcacc cagtttacac catagccgct gaaggtgct                       39

<210> SEQ ID NO 28
<211> LENGTH: 72
<212> TYPE: DNA
<213> ORGANISM: Artificial Sequence
<220> FEATURE:
<223> OTHER INFORMATION: D1.3 CDR 2 oligonucleotide for cloning of HUVNP
      gene (Fig 5)

<400> SEQUENCE: 28
cattgtcact ctggatttga gagctgaatt atagtctgtg tttccatcac cccaaatcat    60
tccaatccac tc                                                       72

<210> SEQ ID NO 29
<211> LENGTH: 48
<212> TYPE: DNA
<213> ORGANISM: Artificial Sequence
<220> FEATURE:
<223> OTHER INFORMATION: D1.3 CDR 3 oligonucleotide for cloning of HUVNP
      gene (Fig 5)

<400> SEQUENCE: 29
gccttgaccc cagtagtcaa gcctataatc tctctctctt gcacaata             48

<210> SEQ ID NO 30
<211> LENGTH: 412
<212> TYPE: DNA
<213> ORGANISM: Artificial Sequence
<220> FEATURE:
<223> OTHER INFORMATION: Nucleotide sequence of the variable domain of
      antibody D1.3 gene(Fig 7)
```

<400> SEQUENCE: 30

```
tcagagcatg gctgtcctgg cattactctt ctgcctggta acattcccaa gctgtatcct      60
ttcccaggtg cagctgaagg agtcaggacc tggcctggtg gcgccctcac agagcctgtc     120
catcacatgc accgtctcag ggttctcatt aaccggctat ggtgtaaact gggttcgcca     180
gcctccagga aagggtctgg agtggctggg aatgatttgg ggtgatggaa acacagacta     240
taattcagct ctcaaatcca gactgagcat cagcaaggac aactccaaga gccaagtttt     300
cttaaaaatg aacagtctgc acactgatga cacagccagg tactactgtg ccagagagag     360
agattatagg cttgactact ggggccaagg caccactctc acagtctcct ca             412
```

<210> SEQ ID NO 31
<211> LENGTH: 135
<212> TYPE: PRT
<213> ORGANISM: Artificial Sequence
<220> FEATURE:
<223> OTHER INFORMATION: Amino acid sequence of the variable domain gene of antibody D1.3 (Fig 7)

<400> SEQUENCE: 31

```
Met Ala Val Leu Ala Leu Leu Phe Cys Leu Val Thr Phe Pro Ser Cys
 1               5                  10                  15

Ile Leu Ser Gln Val Gln Leu Lys Glu Ser Gly Pro Gly Leu Val Ala
             20                  25                  30

Pro Ser Gln Ser Leu Ser Ile Thr Cys Thr Val Ser Gly Phe Ser Leu
         35                  40                  45

Thr Gly Tyr Gly Val Asn Trp Val Arg Gln Pro Pro Gly Lys Gly Leu
     50                  55                  60

Glu Trp Leu Gly Met Ile Trp Gly Asp Gly Asn Thr Asp Tyr Asn Ser
65                  70                  75                  80

Ala Leu Lys Ser Arg Leu Ser Ile Ser Lys Asp Asn Ser Lys Ser Gln
                 85                  90                  95

Val Phe Leu Lys Met Asn Ser Leu His Thr Asp Asp Thr Ala Arg Tyr
            100                 105                 110

Tyr Cys Ala Arg Glu Arg Asp Tyr Arg Leu Asp Tyr Trp Gly Gln Gly
        115                 120                 125

Thr Thr Leu Thr Val Ser Ser
    130                 135
```

<210> SEQ ID NO 32
<211> LENGTH: 614
<212> TYPE: DNA
<213> ORGANISM: Artificial Sequence
<220> FEATURE:
<223> OTHER INFORMATION: DNA sequence of the reshaped antibody heavy chain of rat IgG2a Campath-1 antidbody YTH34.5HL (Fig 9A)

<400> SEQUENCE: 32

```
atgcaaatcc tctgaatcta catggtaaat ataggtttgt ctataccaca aacagaaaaa      60
catgagatca cagttctctc tacagttact gagcacacag gacctcacca tgggatggag     120
ctgtatcatc ctcttcttgg tagcaacagc tacaggtaag ggctcacag tagcaggctt      180
gaggtctgga catatatatg ggtgacaatg acatccactt tgcctttctc tccacaggtg     240
tccactccca ggtccaactg caggagagcg gtccaggtct tgtgagacct agccagaccc     300
tgagcctgac ctgcaccgtg tctggcagca ccttcagcga tttctacatg aactgggtga     360
gacagccacc tggacgaggt cttgagtgga ttggatttat tagagacaaa gctaaaggtt     420
```

```
acacaacaga gtacaatcca tctgtgaagg ggagagtgac aatgctggta gacaccagca    480
agaaccagtt cagcctgaga ctcagcagcg tgacagccgc cgacaccgcg gtctattatt    540
gtgcaagaga gggccacact gctgctcctt tgattactg gggtcaaggc agcctcgtca    600
cagtctcctc aggt                                                      614
```

```
<210> SEQ ID NO 33
<211> LENGTH: 140
<212> TYPE: PRT
<213> ORGANISM: Artificial Sequence
<220> FEATURE:
<223> OTHER INFORMATION: Amino acid sequence of the reshaped antibody
      heavy chain of rat IgG2a Campath-1 antidbody YTH34.5HL (Fig 9A)

<400> SEQUENCE: 33

Met Gly Trp Ser Cys Ile Ile Leu Phe Leu Val Ala Thr Ala Thr Gly
 1               5                  10                  15

Val His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Ser Thr Phe
        35                  40                  45

Ser Asp Phe Tyr Met Asn Trp Val Arg Gln Pro Pro Gly Arg Gly Leu
    50                  55                  60

Glu Trp Ile Gly Phe Ile Arg Asp Lys Ala Lys Gly Tyr Thr Thr Glu
65                  70                  75                  80

Tyr Asn Pro Ser Val Lys Gly Arg Val Thr Met Leu Val Asp Thr Ser
                85                  90                  95

Lys Asn Gln Phe Ser Leu Arg Leu Ser Ser Val Thr Ala Ala Asp Thr
            100                 105                 110

Ala Val Tyr Tyr Cys Ala Arg Glu Gly His Thr Ala Ala Pro Phe Asp
        115                 120                 125

Tyr Trp Gly Gln Gly Ser Leu Val Thr Val Ser Ser
    130                 135                 140
```

```
<210> SEQ ID NO 34
<211> LENGTH: 420
<212> TYPE: DNA
<213> ORGANISM: Rattus
<220> FEATURE:
<223> OTHER INFORMATION: Nucleotide sequence of the heavy chain variable
      domain of rat IgG2a Campath-1 antidbody YTH34.5HL (Fig 9A)

<400> SEQUENCE: 34
atgaagttgt ggctgaactg gattttcctt ttaacacttt taaatggtat ccagtgtgag    60
gtgaaactgt tggaatctgg aggaggcttg gtacagccgg ggggttctat gagactctcc    120
tgtgcaggtt ctggattcac cttcactgat ttctacatga actggatccg ccagcctgca    180
gggaaggcac tgagtggct gggttttatt agagacaaag ctaaaggtta cacaacagag    240
tacaatccat ctgtgaaggg cggttcacc atctccagag ataatacccca aaacatgctc    300 tatcttcaaa tgaacacccct aagagctgag gacactgcca cttactactg tgcaagagag    360
ggccacactg ctgctccttt tgattactgg ggccaaggag tcatggtcac agtctcctca    420
```

```
<210> SEQ ID NO 35
<211> LENGTH: 140
<212> TYPE: PRT
<213> ORGANISM: Rattus
<220> FEATURE:
<223> OTHER INFORMATION: Amino acid sequence of the heavy chain variable
``` domain of rat IgG2a Campath-1 antidbody YTH34.5HL (Fig 9A)

<400> SEQUENCE: 35

Met Lys Leu Trp Leu Asn Trp Ile Phe Leu Leu Thr Leu Leu Asn Gly
1               5                   10                  15

Ile Gln Cys Glu Val Lys Leu Leu Glu Ser Gly Gly Gly Leu Val Gln
            20                  25                  30

Pro Gly Gly Ser Met Arg Leu Ser Cys Ala Gly Ser Gly Phe Thr Phe
        35                  40                  45

Thr Asp Phe Tyr Met Asn Trp Ile Arg Gln Pro Ala Gly Lys Ala Pro
    50                  55                  60

Glu Trp Leu Gly Phe Ile Arg Asp Lys Ala Lys Gly Tyr Thr Thr Glu
65                  70                  75                  80

Tyr Asn Pro Ser Val Lys Gly Arg Phe Thr Ile Ser Arg Asp Asn Thr
                85                  90                  95

Gln Asn Met Leu Tyr Leu Gln Met Asn Thr Leu Arg Ala Glu Asp Thr
            100                 105                 110

Ala Thr Tyr Tyr Cys Ala Arg Glu Gly His Thr Ala Ala Pro Phe Asp
        115                 120                 125

Tyr Trp Gly Gln Gly Val Met Val Thr Val Ser Ser
    130                 135                 140

<210> SEQ ID NO 36
<211> LENGTH: 608
<212> TYPE: DNA
<213> ORGANISM: Artificial Sequence
<220> FEATURE:
<223> OTHER INFORMATION: DNA sequence of the reshaped antibody light
      chain of rat IgG2a Campath-1 antidbody YTH34.5HL (Fig 9B)

<400> SEQUENCE: 36
atgcaaatcc tctgaatcta catggtaaat ataggtttgt ctataccaca aacagaaaaa      60
catgagatca cagttctctc tacagttact gagcacacag gacctcacca tgggatggag     120
ctgtatcatc ctcttcttgg tagcaacagc tacaggtaag gggctcacag tagcaggctt     180
gaggtctgga catatatatg ggtgacaatg acatccactt tgcctttctc tccacaggtg     240
tccactccga catccagatg acccagagcc caagcagcct gagcgccagc gtgggtgaca     300
gagtgaccat cacctgtaaa gcaagtcaga atattgacaa atacttaaac tggtaccagc     360
agaagccagg taaggctcca aagctgctga tctacaatac aaacaatttg caaacgggtg     420
tgccaagcag attcagaggt agcggtagcg gtaccgactt caccttcacc atcagcagcc     480
tccagccaga ggacatcgcc acctactact gcttgcagca tataagtagg ccgcgcacgt     540
tcggccaagg gaccaaggtg gaaatcaaac gtgagtagaa tttaaacttt gcttcctcag     600
ttggatcc                                                              608

<210> SEQ ID NO 37
<211> LENGTH: 127
<212> TYPE: PRT
<213> ORGANISM: Artificial Sequence
<220> FEATURE:
<223> OTHER INFORMATION: Amino acid sequence of the reshaped antibody
      light chain of rat IgG2a Campath-1 antidbody YTH34.5HL(Fig 9B)

<400> SEQUENCE: 37

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala

```
                    20                  25                  30
Ser Val Gly Asp Arg Val Thr Ile Thr Cys Lys Ala Ser Gln Asn Ile
            35                  40                  45

Asp Lys Tyr Leu Asn Trp Tyr Gln Gln Lys Pro Gly Lys Ala Pro Lys
        50                  55                  60

Leu Leu Ile Tyr Asn Thr Asn Asn Leu Gln Thr Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Leu Gln His Ile Ser
            100                 105                 110

Arg Pro Arg Thr Phe Gly Gln Gly Thr Lys Val Glu Ile Lys Arg
        115                 120                 125

<210> SEQ ID NO 38
<211> LENGTH: 387
<212> TYPE: DNA
<213> ORGANISM: Rattus
<220> FEATURE:
<223> OTHER INFORMATION: Nucleotide sequence of the light chain variable
      domain of rat IgG2a Campath-1 antidbody YTH34.5HL (Fig 9B)

<400> SEQUENCE: 38
atgatggctg cacttcaact cttaggggta gctgctagct ctggctccca ggccatgaga    60
tgtgacatca agatgaccca gtctcccctca ttcctgtctg catctgtggg agacagagtc   120
actctcaact gcaaagcaag tcagaatatt gacaaatact aaactggta tcagcaaaag    180 cttggagaat ctcccaactc ctgatatata atacaaaaca atttgcaaac gggcatccca    240
tcaaggttca gtggcagtgg atctggtact gatttcacac tcaccatcag cagcctgcag    300
cctgaagatg ttgccacata tttctgcttg cagcatataa gtaggccgcg cacgtttgga    360
actgggacca agctggagct gaaacgg                                        387

<210> SEQ ID NO 39
<211> LENGTH: 129
<212> TYPE: PRT
<213> ORGANISM: Rattus
<220> FEATURE:
<223> OTHER INFORMATION: Amino acid sequence of the light chain variable
      domain of rat IgG2a Campath-1 antidbody YTH34.5HL (Fig 9B)

<400> SEQUENCE: 39

Met Met Ala Ala Leu Gln Leu Leu Gly Val Ala Ala Ser Ser Gly Ser
1               5                   10                  15

Gln Ala Met Arg Cys Asp Ile Lys Met Thr Gln Ser Pro Ser Phe Leu
            20                  25                  30

Ser Ala Ser Val Gly Asp Arg Val Thr Leu Asn Cys Lys Ala Ser Gln
        35                  40                  45

Asn Ile Asp Lys Tyr Leu Asn Trp Tyr Gln Gln Lys Leu Gly Glu Ser
    50                  55                  60

Pro Lys Leu Leu Ile Tyr Asn Thr Asn Asn Leu Gln Thr Gly Ile Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Leu Gln His
            100                 105                 110

Ile Ser Arg Pro Arg Thr Phe Gly Thr Gly Thr Lys Leu Glu Leu Lys
        115                 120                 125
```

Arg

<210> SEQ ID NO 40
<211> LENGTH: 15
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide I

<400> SEQUENCE: 40
ggccagtgga tagac                                                    15

<210> SEQ ID NO 41
<211> LENGTH: 22
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide III

<400> SEQUENCE: 41
cagtttcatc tagaactgga ta                                            22

<210> SEQ ID NO 42
<211> LENGTH: 25
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide IV

<400> SEQUENCE: 42
gcagttgggt ctagaagtgg acacc                                         25

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide V

<400> SEQUENCE: 43
tcagctgagt cgactgtgac                                               20

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide VI

<400> SEQUENCE: 44
tcacctgagt cgactgtgac                                               20

<210> SEQ ID NO 45
<211> LENGTH: 24
<212> TYPE: DNA
<213> ORGANISM: Artificial Sequence
<220> FEATURE:

```
<223> OTHER INFORMATION: Oligonucleotide sequence used in cloning and
      expression of the reshaped rat heavy chain variable domain
      RaVHCAMP - Oligonucleotide VII

<400> SEQUENCE: 45
agtttcacct cggagtggac acct                                          24

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide VIII

<400> SEQUENCE: 46
tcacctgagg agactgtgac                                               20

<210> SEQ ID NO 47
<211> LENGTH: 17
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide IX

<400> SEQUENCE: 47
ggctggcgaa tccagtt                                                  17

<210> SEQ ID NO 48
<211> LENGTH: 39
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide X

<400> SEQUENCE: 48
ctgtctcacc cagttcatgt agaaatcgct gaaggtgct                          39

<210> SEQ ID NO 49
<211> LENGTH: 81
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide XI

<400> SEQUENCE: 49
cattgtcact ctccccttca cagatggatt gtactctgtt gtgtaacctt tagctttgtc   60
tctaataaat ccaatccact c                                             81

<210> SEQ ID NO 50
<211> LENGTH: 54
<212> TYPE: DNA
<213> ORGANISM: Artificial Sequence
<220> FEATURE:
<223> OTHER INFORMATION: Oligonucleotide sequence used in cloning and
      expression of the reshaped rat heavy chain variable domain
      RaVHCAMP - Oligonucleotide XII

<400> SEQUENCE: 50
gccttgaccc cagtaatcaa aaggagcagc agtgtggccc tctcttgaac aata         54
```

<210> SEQ ID NO 51
<211> LENGTH: 28
<212> TYPE: DNA
<213> ORGANISM: Artificial Sequence
<220> FEATURE:
<223> OTHER INFORMATION: Oligonucleotide sequence used in cloning and
expression of the reshaped rat heavy chain variable domain
RaVHCAMP - Oligonucleotide XIII

<400> SEQUENCE: 51
agaaatcgst gaaggtgaag ccagacaa                                    28

<210> SEQ ID NO 52
<211> LENGTH: 13
<212> TYPE: DNA
<213> ORGANISM: Artificial Sequence
<220> FEATURE:
<223> OTHER INFORMATION: Oligonucleotide sequence used in cloning and
expression of the reshaped rat light chain
variable domain RaVHCAMP - Oligonucleotide II

<400> SEQUENCE: 52
tgcagcatca gcc                                                    13

<210> SEQ ID NO 53
<211> LENGTH: 57
<212> TYPE: DNA
<213> ORGANISM: Artificial Sequence
<220> FEATURE:
<223> OTHER INFORMATION: Oligonucleotide sequence used in cloning and
expression of the reshaped rat light chain
variable domain RaVHCAMP - Oligonucleotide XIV

<400> SEQUENCE: 53
ctgctggtac cagtttaagt atttgtcaat attctgactt gctttacagg tgatggt     57

<210> SEQ ID NO 54
<211> LENGTH: 45
<212> TYPE: DNA
<213> ORGANISM: Artificial Sequence
<220> FEATURE:
<223> OTHER INFORMATION: Oligonucleotide sequence used in cloning and
expression of the reshaped rat light chain
variable domain RaVHCAMP - Oligonucleotide XV

<400> SEQUENCE: 54
gcttggcaca cccgtttgca aattgtttgt attgtagatc agcag                  45

<210> SEQ ID NO 55
<211> LENGTH: 51
<212> TYPE: DNA
<213> ORGANISM: Artificial Sequence
<220> FEATURE:
<223> OTHER INFORMATION: Oligonucleotide sequence used in cloning and
expression of the reshaped rat light chain
variable domain RaVHCAMP - Oligonucleotide XVI

<400> SEQUENCE: 55
cccttggccg aacgtgcgcg gcctacttat atgctgcaag cagtagtagg t           51

<210> SEQ ID NO 56
<211> LENGTH: 373
<212> TYPE: DNA
<213> ORGANISM: Artificial Sequence
<220> FEATURE:
<223> OTHER INFORMATION: DNA sequence of the synthetic gene HuVLLYSo
(Fig 10)

<400> SEQUENCE: 56

```
ctgcagacat ccagatgacc cagagcccaa gcagcctgag cgccagcgtg ggtgacagag      60
tgaccatcac ctgtagagcc agcggtaaca tccacaacta cctggcttgg taccagcaga     120
agccaggtaa ggctccaaag ctgctgatct actacaccac caccctggct gacggtgtgc     180
caagcagatt cagcggtagc ggtagcggta ccgacttcac cttcaccatc agcagcctcc     240
agccagagga catcgccacc tactactgcc agcacttctg gagcacccca aggacgttcg     300
gccaagggac caaggtggaa atcaaacgtg agtagaattt aaactttgct tcctcagttg     360
gatcctagaa ttc                                                        373
```

<210> SEQ ID NO 57
<211> LENGTH: 108
<212> TYPE: PRT
<213> ORGANISM: Artificial Sequence
<220> FEATURE:
<223> OTHER INFORMATION: Derived amino acid sequence of the synthetic gene HuVLLYSo (Fig 10)

<400> SEQUENCE: 57

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gly Asn Ile His Asn Tyr
             20                  25                  30

Leu Ala Trp Tyr Gln Gln Lys Pro Gly Lys Ala Pro Lys Leu Leu Ile
         35                  40                  45

Tyr Tyr Thr Thr Thr Leu Ala Asp Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln His Phe Trp Ser Thr Pro Arg
                 85                  90                  95

Thr Phe Gly Gln Gly Thr Lys Val Glu Ile Lys Arg
            100                 105
```

<210> SEQ ID NO 58
<211> LENGTH: 616
<212> TYPE: DNA
<213> ORGANISM: Artificial Sequence
<220> FEATURE:
<223> OTHER INFORMATION: DNA sequence of the synthetic gene HuVLLYS (Fig 11)

<400> SEQUENCE: 58

```
atgcaaatcc tctgaatcta catggtaaat ataggtttgt ctataccaca aacagaaaaa      60
catgagatca cagttctctc tacagttact gagcacacag ggacctcacc atgggatgga    120
gctgtatcat cctcttcttg gtagcaacag ctacaggtaa ggggctcaca gtagcaggct    180
tgaggtctgg acatatatat gggtgacaat gacatccact ttgcctttct ctccacaggt    240
gtccactccg acatccaatg acccagagcc aagcagcct gagcgccagc gtgggtgaca    300
gagtgaccat cacctgtaga gccagcggta acatccacaa ctacctggct tggtaccagc    360
agaagccagg taaggctcca aagctgctga tctactacac caccaccctg ctgacggtg    420 tgccaagcag attcagaggt agcggtagcg gtaccgactt caccttcacc atcagcagcc    480
tccagccaga ggacatcgcc acctactact gccagcactt ctggagcacc ccaaggacgt    540
tcggccaagg gaccaaggtg gaaatcaaac gtgagtagaa tttaaacttt gcttcctcag    600
```

-continued

```
ttggatccta gaattc                                                    616

<210> SEQ ID NO 59
<211> LENGTH: 127
<212> TYPE: PRT
<213> ORGANISM: Artificial Sequence
<220> FEATURE:
<223> OTHER INFORMATION: Derived amino acid sequence of the synthetic
      gene HuVLLYS (Fig 11)

<400> SEQUENCE: 59

Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gly Asn Ile
        35                  40                  45

His Asn Tyr Leu Ala Trp Tyr Gln Gln Lys Pro Gly Lys Ala Pro Lys
    50                  55                  60

Leu Leu Ile Tyr Tyr Thr Thr Thr Leu Ala Asp Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln His Phe Trp Ser
            100                 105                 110

Thr Pro Arg Thr Phe Gly Gln Gly Thr Lys Val Glu Ile Lys Arg
        115                 120                 125
```